US008180592B2

(12) United States Patent
Yuen et al.

(10) Patent No.: US 8,180,592 B2
(45) Date of Patent: May 15, 2012

(54) PORTABLE MONITORING DEVICES AND METHODS OF OPERATING SAME

(75) Inventors: Shelten Gee Jao Yuen, Berkeley, CA (US); James Park, Berkeley, CA (US); Eric Nathan Friedman, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 13/249,155

(22) Filed: Sep. 29, 2011

(65) Prior Publication Data

US 2012/0084054 A1    Apr. 5, 2012

Related U.S. Application Data

(62) Division of application No. 13/156,304, filed on Jun. 8, 2011.

(60) Provisional application No. 61/388,595, filed on Sep. 30, 2010, provisional application No. 61/390,811, filed on Oct. 7, 2010.

(51) Int. Cl.
*G06F 19/00* (2011.01)
(52) U.S. Cl. ........................................ 702/160
(58) Field of Classification Search .................. 702/150, 702/152, 160, 182–185, 188
See application file for complete search history.

(56) References Cited

U.S. PATENT DOCUMENTS

| 4,312,358 A | 1/1982 | Barney |
| 4,367,752 A | 1/1983 | Jimenez et al. |
| 4,578,769 A | 3/1986 | Frederick |
| 4,977,509 A | 12/1990 | Pitchford et al. |
| 5,058,427 A | 10/1991 | Brandt |
| 5,224,059 A | 6/1993 | Nitta et al. |
| 5,295,085 A | 3/1994 | Hoffacker |
| 5,323,650 A | 6/1994 | Fullen et al. |
| 5,583,776 A | 12/1996 | Levi et al. |
| 5,671,162 A | 9/1997 | Werbin |

(Continued)

FOREIGN PATENT DOCUMENTS

JP    11347021    12/1999

OTHER PUBLICATIONS

"Automatic classification of ambulatory movements and evaluation of energy consumptions utilizing accelerometers and a barometer", Ohtaki, et al, Microsystem Technologies, vol. 11, No. 8-10, Aug. 2005, pp. 1034-1040.

(Continued)

*Primary Examiner* — Edward Raymond
(74) *Attorney, Agent, or Firm* — Neil A. Steinberg

(57) ABSTRACT

The present inventions, in one aspect, are directed to a portable monitoring device comprises (i) a housing having a physical size and shape that is adapted to couple to the user, (ii) a motion sensor, disposed in the housing, to detect motion of a user and, in response thereto, to generate motion data, (iii) an altitude sensor, disposed in the housing, to detect a change in altitude of the user and, in response thereto, to generate change in altitude data, and (iv) processing circuitry, disposed in the housing, to: (a) calculate a change in elevation of the user using the motion data and the change in altitude data, and (b) a state of an avatar (which is a graphical representation of the user) using the motion data and/or the change in altitude data, and (vi) a display to output state of avatar data.

29 Claims, 50 Drawing Sheets

U.S. PATENT DOCUMENTS

| | | | |
|---|---|---|---|
| 5,724,265 | A | 3/1998 | Hutchings |
| 5,891,042 | A | 4/1999 | Sham et al. |
| 5,899,963 | A | 5/1999 | Hutchings |
| 5,947,868 | A | 9/1999 | Dugan |
| 5,955,667 | A | 9/1999 | Fyfe |
| 5,976,083 | A | 11/1999 | Richardson et al. |
| 6,018,705 | A | 1/2000 | Gaudet et al. |
| 6,145,389 | A | 11/2000 | Ebeling et al. |
| 6,183,425 | B1 | 2/2001 | Whalen et al. |
| 6,287,262 | B1 | 9/2001 | Amano et al. |
| 6,301,964 | B1 | 10/2001 | Fyfe et al. |
| 6,305,221 | B1 | 10/2001 | Hutchings |
| 6,309,360 | B1 | 10/2001 | Mault |
| 6,478,736 | B1 | 11/2002 | Mault |
| 6,513,381 | B2 | 2/2003 | Fyfe et al. |
| 6,513,532 | B2 | 2/2003 | Mault et al. |
| 6,529,827 | B1 | 3/2003 | Beason et al. |
| 6,571,200 | B1 | 5/2003 | Mault |
| 6,678,629 | B2 | 1/2004 | Tsuji |
| 6,761,064 | B2 | 7/2004 | Tsuji |
| 6,790,178 | B1 | 9/2004 | Mault et al. |
| 6,813,582 | B2 | 11/2004 | Levi et al. |
| 7,062,225 | B2 | 6/2006 | White |
| 7,162,368 | B2 | 1/2007 | Levi et al. |
| 7,171,331 | B2 * | 1/2007 | Vock et al. .................... 702/160 |
| 7,200,517 | B2 | 4/2007 | Darley et al. |
| 7,261,690 | B2 | 8/2007 | Teller et al. |
| 7,373,820 | B1 * | 5/2008 | James ............................ 73/488 |
| 7,457,724 | B2 | 11/2008 | Vock et al. |
| 7,505,865 | B2 | 3/2009 | Ohkubo et al. |
| 7,690,556 | B1 | 4/2010 | Kahn et al. |
| 7,774,156 | B2 | 8/2010 | Niva et al. |
| 7,789,802 | B2 | 9/2010 | Lee et al. |
| 7,927,253 | B2 | 4/2011 | Vincent et al. |
| 7,983,876 | B2 | 7/2011 | Vock et al. |
| 2005/0054938 | A1 | 3/2005 | Wehman et al. |
| 2005/0107723 | A1 | 5/2005 | Wehman et al. |
| 2006/0020177 | A1 * | 1/2006 | Seo et al. ...................... 600/300 |
| 2006/0047208 | A1 | 3/2006 | Yoon |
| 2006/0143645 | A1 * | 6/2006 | Vock et al. ........................ 725/9 |
| 2007/0050715 | A1 | 3/2007 | Behar |
| 2007/0051369 | A1 | 3/2007 | Choi et al. |
| 2008/0140338 | A1 | 6/2008 | No et al. |
| 2009/0018797 | A1 | 1/2009 | Kasama et al. |
| 2009/0043531 | A1 * | 2/2009 | Kahn et al. .................... 702/149 |
| 2009/0048044 | A1 | 2/2009 | Oleson et al. |
| 2011/0003665 | A1 * | 1/2011 | Burton et al. ..................... 482/9 |
| 2011/0022349 | A1 * | 1/2011 | Stirling et al. ................ 702/141 |
| 2011/0106449 | A1 * | 5/2011 | Chowdhary et al. .......... 701/214 |
| 2011/0131005 | A1 * | 6/2011 | Ueshima et al. .............. 702/141 |

OTHER PUBLICATIONS

"Classification of Human Moving Patterns Using Air Pressure and Acceleration", Sagawa, et al, Proceedings of the 24th Annual Conference of the IEEE Industrial Electronics Society, vol. 2, Aug.-Sep. 1998, pp. 1214-1219.

"Non-restricted measurement of walking distance", Sagawa, et al, IEEE Int'l Conf. on Systems, Man, and Cybernetics, vol. 3, Oct. 2000, pp. 1847-1852.

"Activity Classification Using Realistic Data From Wearable Sensors", Parkka, et al, IEEE Transactions on Information Technology in Biomedicine, vol. 10, No. 1, Jan. 2006, pp. 119-128.

"Indoor Navigation with MEMS sensors", Lammel, et al, Proceedings of the Eurosensors XXIII conference, vol. 1, No. 1, Sep. 2009, pp. 532-535.

"Design of a Wireless Assisted Pedestrian Dead Reckoning System—The NavMote Experience", Fang, et al, IEEE Transactions on Instrumentation and Measurement, vol. 54, No. 6, Dec. 2005, pp. 2342-2358.

"On Foot Navigation: When GPS alone is not enough", Ladetto, et al, Journal of Navigation, vol. 53, No. 2, Sep. 2000, pp. 279-285.

"A Hybrid Discriminative/Generative Approach for Modeling Human Activities", Lester, et al, Proc. of the Int'l Joint Conf. Artificial Intelligence, 2005, pp. 766-772.

"Using MS5534 for altimeters and barometers", Intersema App., Note AN501, Jan. 2006.

"Validated caloric expenditure estimation using a single body-worn sensor", Lester, et al, Proc. of the Int'l Conf. on Ubiquitous Computing, 2009, pp. 225-234.

"Drift-free dynamic height sensor using MEMS IMU aided by MEMS pressure sensor", Tanigawa, et al, Workshop on Positioning, Navigation and Communication, Mar. 2008, pp. 191-196.

"Improvement of walking speed prediction by accelerometry and altimetry, validated by satellite positioning", Perrin, et al, Medical & Biological Engineering & Computing, vol. 38, 2000, pp. 164-168.

"An Intelligent Multi-sensor System for Pedestrian Navigation", Retscher, Journal of Global Positioning Systems, vol. 5, No. 1, 2006, pp. 110-118.

"Evaluation of a New Method of Heading Estimation for Pedestrian Dead Reckoning Using Shoe Mounted Sensors", Stirling et al., Journal of Navigation, vol. 58, 2005, pp. 31-45.

"Direct measurement of human movement by accelerometry", Godfrey, et al, Medical Engineering & Physics, vol. 30, 2008, pp. 1364-1386.

"Foot mounted inertial system for pedestrian navigation", Godha et al., Measurement Science and Technology, vol. 19, No. 7, May 2008, pp. 1-9.

"Altimeter and Barometer System", Clifford, et al, Freescale Semiconductor Application Note AN1979, Rev 3, Nov. 2006.

"SCP1000-D01/D11 Pressure Sensor as Barometer and Altimeter", VTI Technologies Application, Jun. 2006, Note 33.

"Suunto LUMI User Guide", Jun. and Sep. 1997.

* cited by examiner

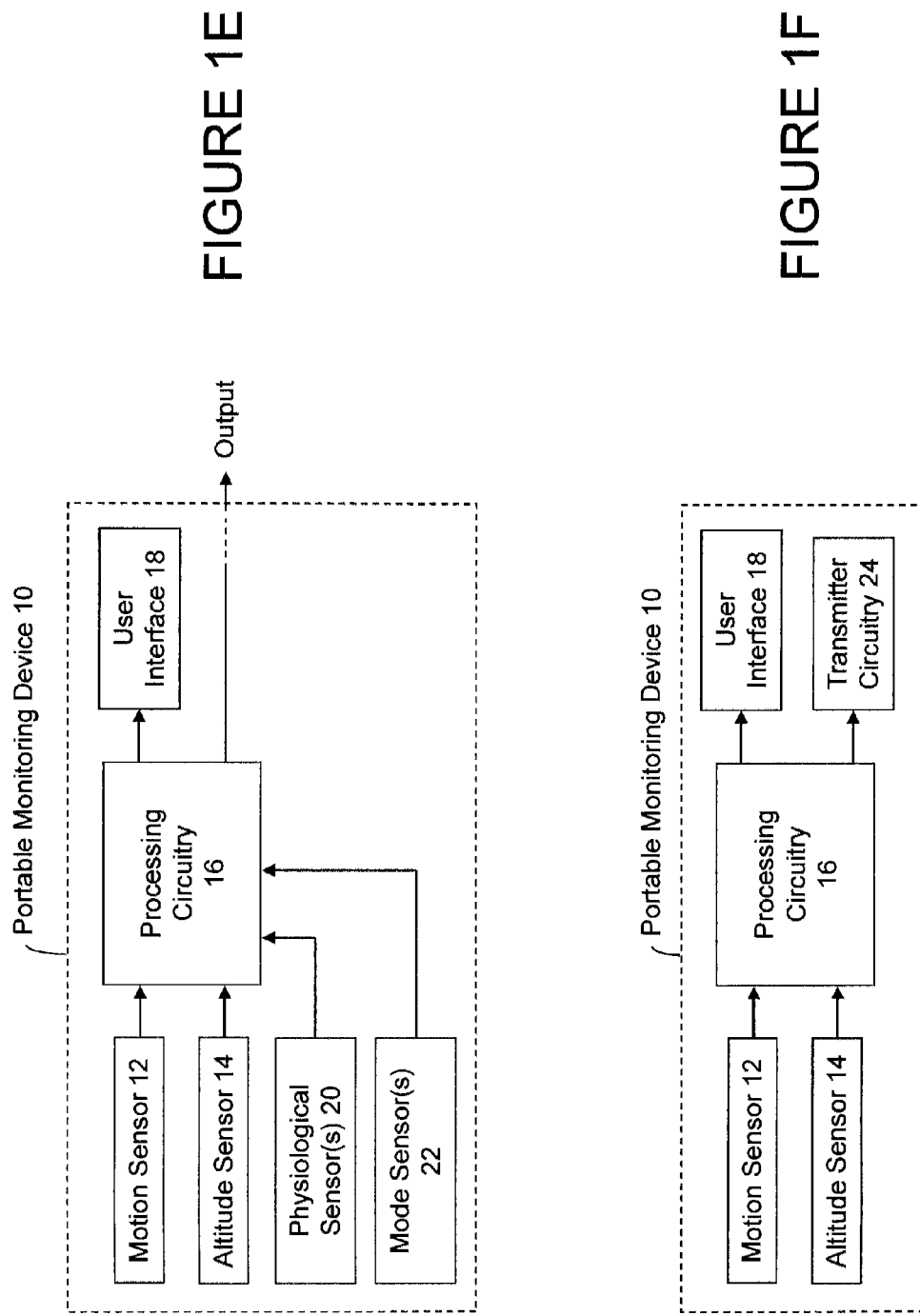

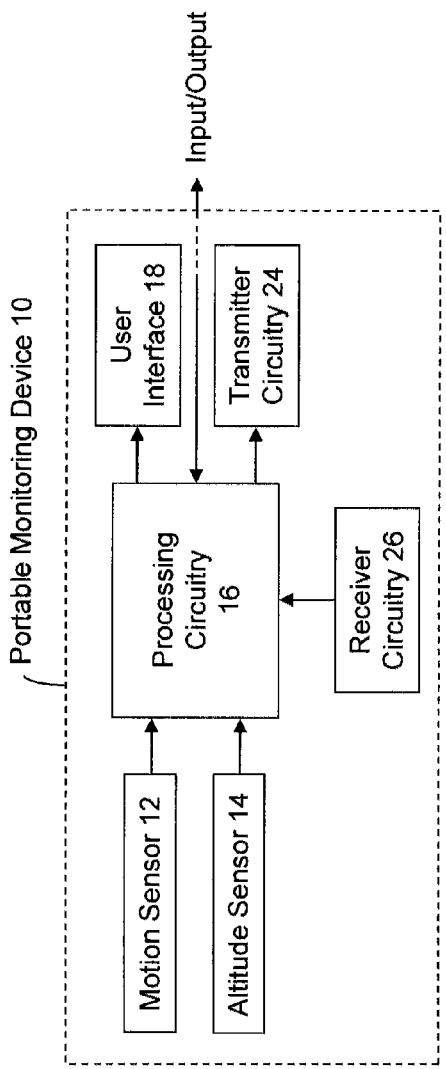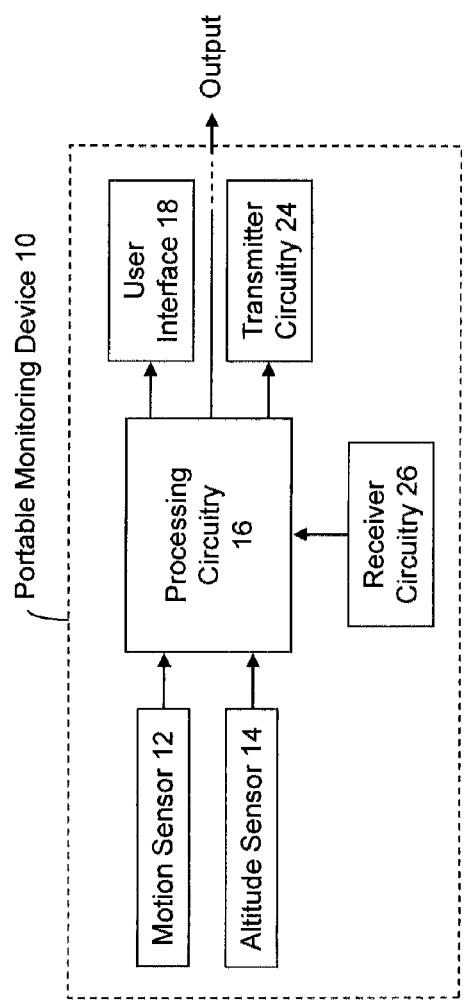
FIGURE 1K
FIGURE 1L

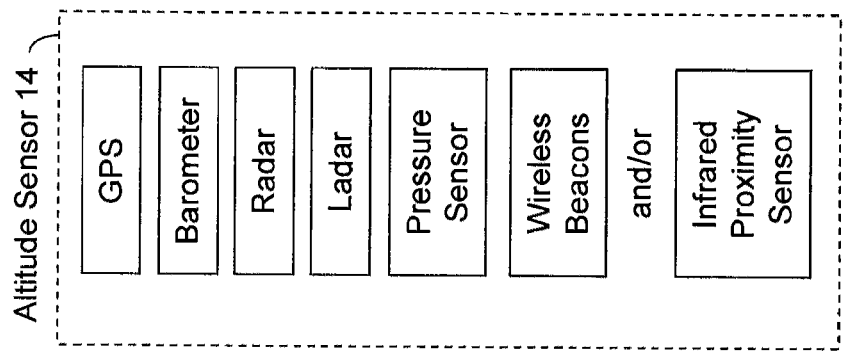
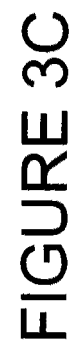
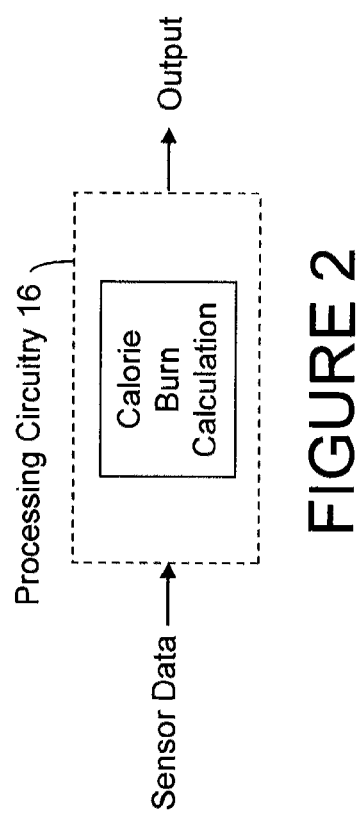
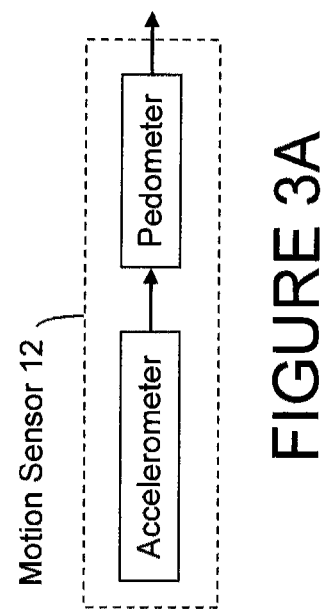

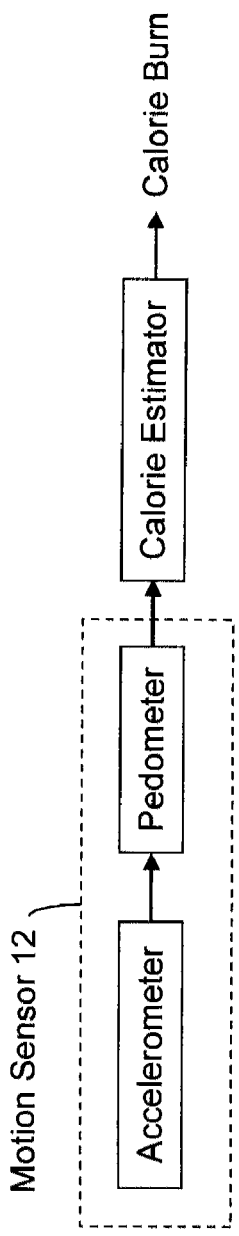
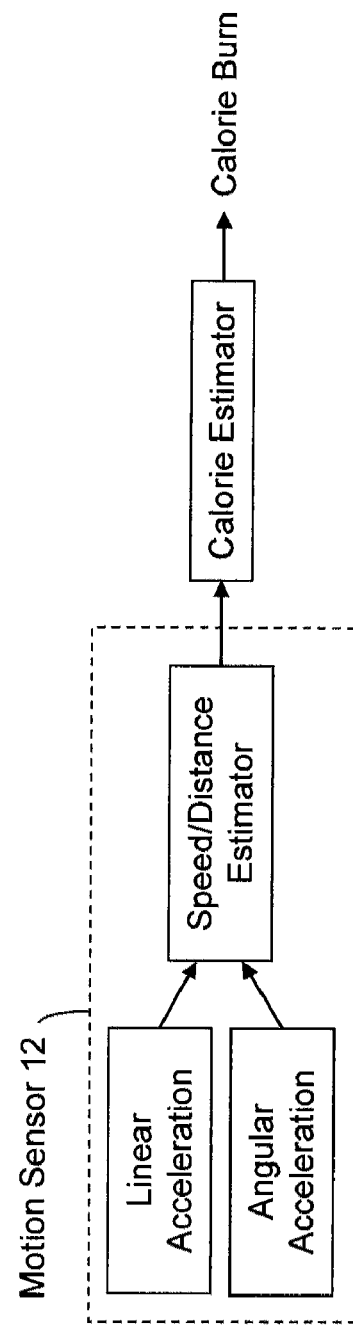

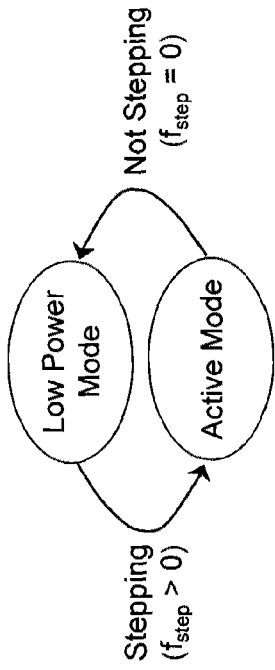
FIGURE 9B
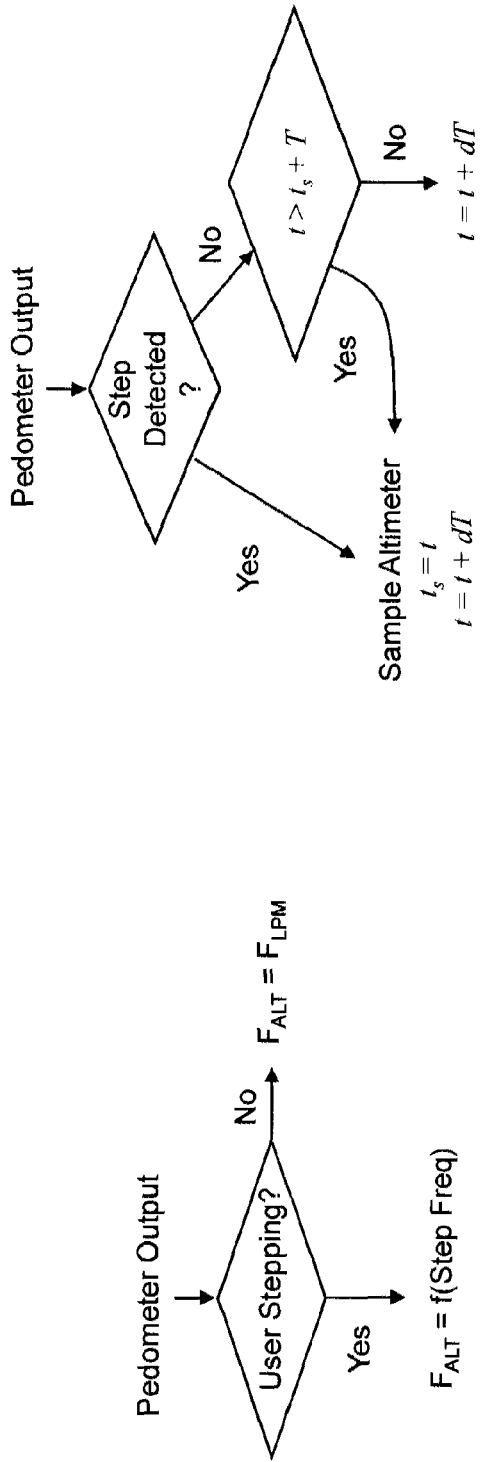
FIGURE 9D
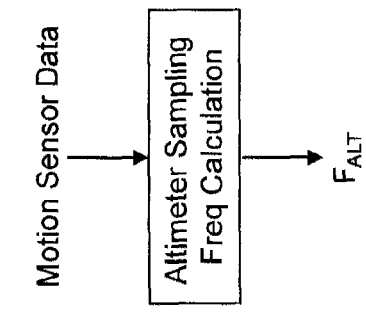
FIGURE 9A
FIGURE 9C

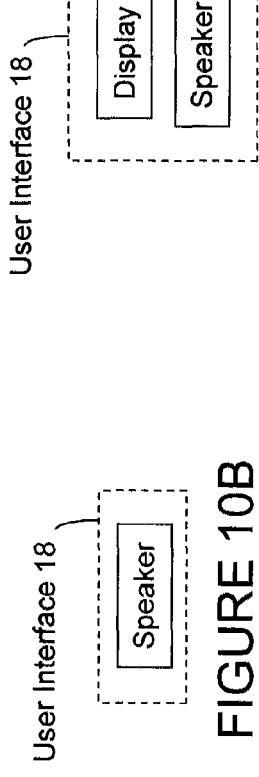
FIGURE 10A
FIGURE 10B
FIGURE 10C
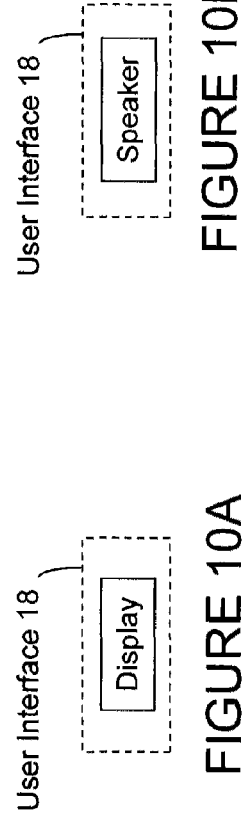
FIGURE 10D
FIGURE 10E
FIGURE 10F Flick

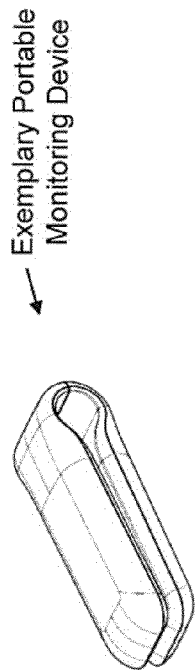
FIGURE 16A
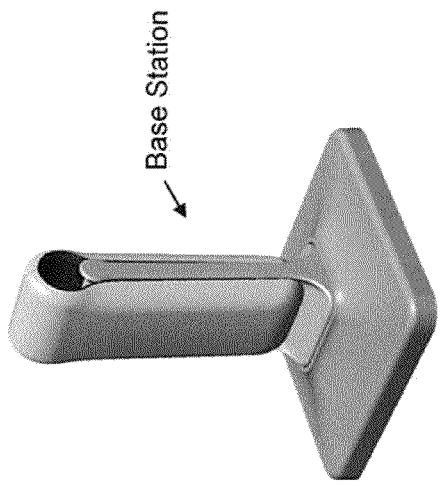
FIGURE 16C
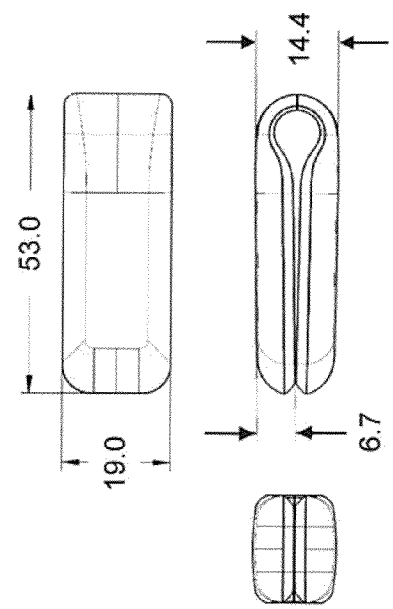
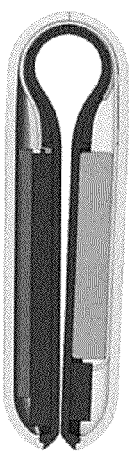
FIGURE 16B

US 8,180,592 B2

PORTABLE MONITORING DEVICES AND METHODS OF OPERATING SAME

RELATED APPLICATION

This application is a divisional of U.S. patent application Ser. No. 13/156,304, filed on Jun. 8, 2011, entitled "Portable Monitoring Devices and Methods of Operating Same" (still pending). This non-provisional application claims priority to U.S. Provisional Application No. 61/388,595, entitled "Portable Monitoring Devices and Methods of Operating Same", filed Sep. 30, 2010, and U.S. Provisional Application No. 61/390,811, entitled "Portable Monitoring Devices and Methods of Operating Same", filed Oct. 7, 2010; the contents of these U.S. Provisional Applications are incorporated by reference herein in their entirety.

INTRODUCTION

The present inventions relate to portable monitoring devices, and method of operating and controlling same, wherein the portable monitoring devices include an altitude sensor, motion sensor and processing circuitry to calculate, assess and/or determine calorie burn and/or other activity-related quantities of the user (for example, a human or non-human animal such as a dog, cat or horse). In these aspects, the present inventions employ the altitude sensor data and the motion sensor data to calculate, assess and/or determine the calorie burn and/or other activity-related quantities of the user (for example, number of steps and/or stairs, number of stair flights, elevation gain/loss from ambulatory and/or non-ambulatory locomotion, absolute elevation, elevation and/or activity points, activity intensity, distance traveled and/or pace, number of swim strokes and/or kicks, strokes per lap, lap time, pace and/or distance, number of pedal rotations of a bicycle, arm or wheel rotation of a wheelchair, heart rate, heart rate variability, respiration rate, stress levels, skin temperature, body temperature). In the following disclosure, use of the term "activity" includes sedentary and nonsedentary activities. As such, the present inventions also may be used to monitor activities related to sleeping, lying, sitting, and standing stationary and may provide corresponding metrics (for example, time asleep, the onset, duration, and number of awakenings while attempting to sleep, the time spent in various stages of sleep, sleep latency, sleep efficiency and other sleep quality parameters, the presence of sleep apnea and other diagnostic measures, time spent in a prone non-standing state, and resting heart rate).

In other aspects, the portable monitoring device of the present inventions may include a physiological sensor, in addition to the altitude sensor, motion sensor and processing circuitry. In these aspects, the present inventions employ the physiological sensor data, altitude sensor data and motion sensor data to calculate, assess and/or determine the calorie burn and/or such other activity-related quantities of the user.

In certain aspects the processing circuitry is partially or wholly disposed external to the portable monitoring device wherein the external processing circuitry receives partially processed or "raw" sensor data. Here, the external processing circuitry partially or wholly calculates, assesses and/or determines the calorie burn and/or other activity-related quantities of the user.

Notably, the present inventions also relate to techniques or methods of calculating, assessing and/or determining the calorie burn and/or other activity-related quantities of the user based on or using sensor data acquired by a portable monitoring device, for example, devices according to any of the of the present inventions.

SUMMARY

There are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Importantly, this Summary may not be reflective of or correlate to the inventions protected by the claims in this or continuation/divisional applications hereof. Even where this Summary is reflective of or correlates to the inventions protected by the claims hereof, this Summary may not be exhaustive of the scope of the present inventions.

In a first aspect, the present inventions are directed to a portable monitoring device to calculate calorie burn or expenditure of a user wherein the portable monitoring device includes a housing having a physical size and shape that is adapted to couple to the body of the user. In this first aspect, the portable monitoring device includes a motion sensor to detect motion of the user and, in response, to generate data which is representative of motion of the user, and an altitude sensor to detect a change in altitude of the user and, in response, to generate data which is representative of the change in altitude of the user. The portable monitoring device may also include processing circuitry, coupled to the motion sensor and the altitude sensor, to (a) calculate data which is representative of a change in elevation of the user using (i) the data which is representative of motion of the user and (ii) the data which is representative of a change in altitude of the user, (b) calculate first calorie burn using the data which is representative of motion of the user, and (c) calculate second calorie burn by adjusting the first calorie burn based on data which is representative of a change in elevation of the user.

The portable monitoring device may also include a display, coupled to the processing circuitry, to output the second calorie burn.

In one embodiment, the processing circuitry of the portable monitoring device determines a change in elevation of the user when (i) the data which is representative of motion of the user exceeds a first threshold and (ii) the data which is representative of a change in altitude of the user exceeds a second threshold.

The processing circuitry may also calculate data which is representative of an accumulation of changes in elevation of the user by summing data which is representative of changes in elevation of the user in response to detecting a predetermined motion of the user based on the data which is representative of motion of the user. Here, the processing circuitry may calculate an altitude metric (for example, a number of stairs and/or a number of flights of stairs) using the data which is representative of the accumulation of changes in elevation of the user. A display, may output the altitude metric.

In another embodiment, the processing circuitry may also calculate data which is representative of an increase and/or decrease in elevation for a given time period using the data which is representative of a change in elevation of the user, and a display may output the data which is representative of (i) an increase and/or decrease in elevation for a given time period, and (ii) the second calorie burn.

Notably, the motion sensor, in one embodiment, may be a pedometer and the altitude sensor may be sampled based on data which is representative of determining a step by the user.

In another aspect, the present inventions are directed to a portable monitoring device to calculate calorie burn of a user, wherein the portable monitoring device includes a housing having a physical size and shape that is adapted to couple to the body of the user. The portable monitoring device again includes a motion sensor to detect motion of the user and, in response, to generate data which is representative of motion of the user, and an altitude sensor to detect a change in altitude of the user and, in response, to generate data which is representative of the change in altitude of the user. In this aspect, the processing circuitry (a) calculates data which is representative of a change in elevation of the user using (i) the data which is representative of motion of the user and (ii) the data which is representative of a change in altitude of the user, (b) calculates a speed of the user using the data which is representative of motion of the user, (c) calculates calorie burn using (i) the data which is representative of motion of the user, (ii) the data which is representative of a change in elevation of the user, and (iii) the speed of the user.

In one embodiment, the portable monitoring device also calculates an activity state of the user using the data which is representative of an ambulatory speed of the user, and calorie burn using (i) the data which is representative of motion of the user, (ii) the data which is representative of a change in elevation of the user, (iii) the speed of the user, and (iv) the activity state of the user. The processing circuitry may determine the activity state of the user based on data from the motion and/or altitude sensors, and/or based on input data or an input instruction.

In one embodiment, the processing circuitry correlates the data which is representative of a change in elevation of the user to a number of stairs and/or a number of flights of stairs. Indeed, the processing circuitry may calculate an altitude metric using the data which is representative of a change in elevation of the user. The altitude metric may include a number of stairs and/or a number of flights of stairs. A display, coupled to the processing circuitry, may output the altitude metric. Moreover, circuitry, coupled to the processing circuitry, may be employed to output data which is representative of: (i) the altitude metric and (ii) the calorie burn.

In another embodiment, the processing circuitry determines a change in elevation of the user when (i) the data which is representative of motion of the user exceeds a first threshold and (ii) the data which is representative of a change in altitude of the user exceeds a second threshold. The processing circuitry may also calculate data which is representative of an accumulation of changes in elevation of the user by summing data which is representative of changes in elevation of the user in response to detecting a predetermined motion of the user based on the data which is representative of motion of the user.

Indeed, in another embodiment, the processing circuitry may calculate data which is representative of an increase and/or decrease in elevation for a given time period using the data which is representative of a change in elevation of the user; and a display may output the data which is representative of an increase and/or decrease in elevation.

In another aspect, the present inventions are again directed to a portable monitoring having a motion sensor to detect motion of the user and, in response, to generate data which is representative of motion of the user, and an altitude sensor to detect a change in altitude of the user and, in response, to generate data which is representative of the change in altitude of the user. In this aspect, the processing circuitry calculates (a) data which is representative of a change in elevation of the user using (i) the data which is representative of motion of the user and (ii) the data which is representative of a change in altitude of the user, (b) an activity state of the user using the data which is representative of motion of the user, and (c) calorie burn using (i) the data which is representative of motion of the user, (ii) the activity state, and (iii) data which is representative of a change in elevation of the user. The housing of the portable monitoring device includes a physical size and shape that is adapted to couple to the body of the user.

Notably, the processing circuitry may determine the activity state of the user based on data from the motion sensor, data from the altitude sensor, input data and/or input instruction.

In one embodiment, the processing circuitry correlates the data which is representative of a change in elevation of the user to a number of stairs and/or a number of flights of stairs. In another embodiment, the processing circuitry further calculates an altitude metric (for example, a number of stairs and/or flights of stairs traversed by the user) based on the data which is representative of a change in elevation of the user and the data which is representative of motion of the user. Circuitry, coupled to the processing circuitry, may output data which is representative of: (i) the altitude metric and (ii) the calorie burn. Indeed, a display, coupled to the processing circuitry, may output the altitude metric and the calorie burn.

In yet another embodiment, the processing circuitry determines a change in elevation of the user when (i) the data which is representative of motion of the user exceeds a first threshold and (ii) the data which is representative of a change in altitude of the user exceeds a second threshold. The processing circuitry may calculate data which is representative of an accumulation of changes in elevation of the user by summing data which is representative of changes in elevation of the user in response to detecting a predetermined motion of the user based on the data which is representative of motion of the user.

The portable monitoring device may include a display, coupled to the processing circuitry. Here, the processing circuitry may calculate data which is representative of an increase and/or decrease in elevation for a given time period using the data which is representative of a change in elevation of the user and the data which is representative of motion of the user. The display outputs the data which is representative of an increase and/or decrease in elevation.

As stated herein, there are many inventions, and aspects of the inventions, described and illustrated herein. This Summary is not exhaustive of the scope of the present inventions. Indeed, this Summary may not be reflective of or correlate to the inventions protected by the claims in this or continuation/divisional applications hereof.

Moreover, this Summary is not intended to be limiting of the inventions or the claims (whether the currently presented claims or claims of a divisional/continuation application) and should not be interpreted in that manner. While certain embodiments have been described and/or outlined in this Summary, it should be understood that the present inventions are not limited to such embodiments, description and/or outline, nor are the claims limited in such a manner (which should also not be interpreted as being limited by this Summary).

Indeed, many other aspects, inventions and embodiments, which may be different from and/or similar to, the aspects, inventions and embodiments presented in this Summary, will be apparent from the description, illustrations and claims, which follow. In addition, although various features, attributes and advantages have been described in this Summary and/or are apparent in light thereof, it should be understood that such features, attributes and advantages are not required whether in one, some or all of the embodiments of the present inventions and, indeed, need not be present in any of the embodiments of the present inventions.

BRIEF DESCRIPTION OF THE DRAWINGS

In the course of the detailed description to follow, reference will be made to the attached drawings. These drawings show different aspects of the present inventions and, where appropriate, reference numerals illustrating like structures, components, materials and/or elements in different figures are labeled similarly. It is understood that various combinations of the structures, components, and/or elements, other than those specifically shown, are contemplated and are within the scope of the present inventions.

Moreover, there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, certain permutations and combinations are not discussed and/or illustrated separately herein.

FIGS. 1A-1L are block diagram representations of exemplary portable monitoring devices, according to at least certain aspects of certain embodiments of the present inventions, wherein the portable monitoring devices, according to at least certain aspects of certain embodiments of the present inventions, include processing circuitry, one or more altitude sensors, one or more motion sensors and, in certain embodiments, one or more physiological sensors, one or more mode sensors, transmitter circuitry and/or receiver circuitry;

FIG. 2 is a block diagram representation of processing circuitry to calculate, assess and/or determine the calorie burn of the user based on sensor data; the processing circuitry may include memory (for example, Flash memory, DRAM and/or SRAM) to store, for example, (i) sensor data and (ii) information which is representative of calorie burn—for example, cumulative and/or over time; notably, the processing circuitry may be discrete or integrated logic, and/or one or more state machines, processors (suitably programmed) and/or field programmable gate arrays (or combinations of the aforementioned); indeed, any circuitry (for example, discrete or integrated logic, state machine(s), processor(s) (suitably programmed) and/or field programmable gate array(s) (or combinations of the aforementioned)) now known or later developed may be employed to calculate, determine, assess and/or determine the calorie burn of the user based on sensor data;

FIGS. 3A and 3B are block diagram representations of exemplary motion sensors which include, for example, one or more accelerometers, gyroscopes, compasses, switches (for example, mechanical), piezoelectric film and/or pedometers to determine, calculate and/or detect one or more steps of the user; notably, the exemplary motion sensor may be incorporated in any of the exemplary portable monitoring devices;

FIG. 3C is a block diagram representation of one or more altitude sensor(s) that may be incorporated in the exemplary portable monitoring devices according to any of the exemplary embodiments of the present inventions;

FIGS. 4A-4D, 4F, 4H-4J, and 4M-4R are flowcharts of exemplary processes of calculating, obtaining, assessing and/or determining calorie burn of the user based on certain sensor data, according to certain aspects of the present inventions;

FIGS. 5A and 5B are block diagram representations of the motion sensor in combination with flowcharts of exemplary processes of calculating, obtaining, assessing and/or determining calorie burn of the user based on speed data, according to certain aspects of the present inventions;

FIGS. 9A-9D are flowcharts of exemplary processes of controlling, adjusting and/or determining a sampling frequency of the altitude sensor ($F_{ALT}$) based on or using data which is representative of motion of the user (for example, from a motion sensor of the portable monitoring device), according to certain aspects of the present inventions; notably FIG. 9D illustrates an embodiment of the portable monitoring device where sampling of the altitude sensor is determined or triggered based on or using step events detected by a motion sensor (for example, a pedometer), or a maximum time T between samples (whichever occurs first);

FIGS. 10A-10F are block diagram representations of exemplary user interfaces of the exemplary portable monitoring devices according to at least certain embodiments of the present inventions; in these exemplary illustrative embodiments, the user interface includes output mechanisms (for example, a display and/or speaker) and input mechanism (for example, switches, a microphone, and vibration and gesture recognition sensor(s), wherein the user may input data and/or commands); notably, any manner of and/or mechanism for outputting and/or inputting of data and/or commands (for example, responses to, for example, queries) are intended to fall within the scope of the present inventions;

FIGS. 16A and 16B illustrates different views of an exemplary embodiment of the portable monitoring device according to certain aspects of the present inventions; notably, exemplary physical specifications or dimensions (in millimeters) are outlined in connection with the top down and side views of FIG. 16A;

FIG. 16C illustrates an exemplary embodiment of the portable monitoring device of FIGS. 16A and 16B disposed on a base station.

Again, there are many inventions described and illustrated herein. The present inventions are neither limited to any single aspect nor embodiment thereof, nor to any combinations and/or permutations of such aspects and/or embodiments. Each of the aspects of the present inventions, and/or embodiments thereof, may be employed alone or in combination with one or more of the other aspects of the present inventions and/or embodiments thereof. For the sake of brevity, many of those combinations and permutations are not discussed separately herein.

DETAILED DESCRIPTION

Figure 1A:
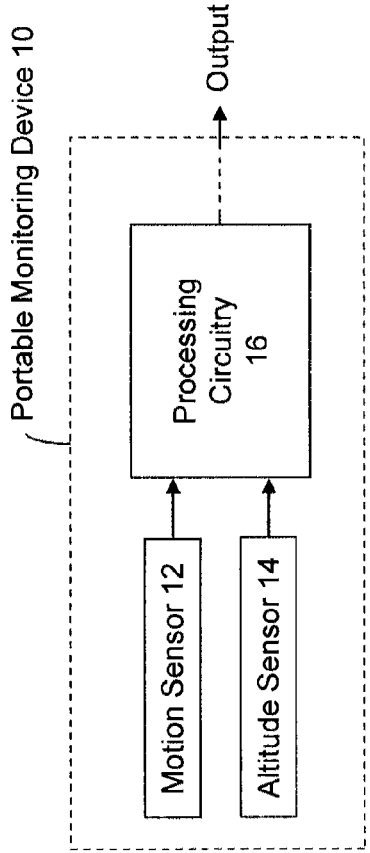

There are many inventions described and illustrated herein. In one aspect, the present inventions are directed to portable monitoring devices, and method of operating and controlling same, which monitor, calculate, determine and/or detect energy and/or calorie "burn" due to physical activity of the user (for example, a human or non-human animal) and/or other activity-related metrics. The portable monitoring devices of the present inventions include an altitude sensor, motion sensor and processing circuitry to calculate, assess and/or determine the calorie burn of the user and/or other activity-related metrics. (See, for example, FIG. 1A). In one embodiment, at least a portion of the portable monitoring device (including the one or more altitude sensors and/or motion sensors) is affixed to the user during operation wherein the housing of the device includes a physical size and shape that facilitates coupling to the user, for example, the body of the user (such as, for example, arm, wrist, angle, waist and/or foot) and allows the user to perform normal or typical user activities (including, for example, exercise of all kinds and type) without hindering the user from performing such activities. The portable monitoring device may include a mechanism (for example, a clip, strap and/or tie) that facilitates coupling or affixing the device to the user during such normal or typical user activities.

Briefly, during operation, the altitude sensor generates data which is representative of the altitude and/or changes in altitude of the user. The motion sensor generates data which is representative of motion of the user. The processing circuitry, using (i) data which is representative of the altitude and/or changes in altitude and (ii) data which is representative of the motion of the user, determines, calculates, assesses, estimates and/or detects energy and/or calorie "burn" of the user. (See, FIG. 2).

Notably, the processing circuitry may also calculate, assess, estimate and/or determine other activity-related metrics including, for example, (i) in the context of running/walking on level, substantially level, or relatively level ground, (a) number of steps, which may be categorized according to the number of steps associated with a user state, for example, walking, jogging and/or running, (b) distance traveled and/or (c) pace, (ii) in the context of running/jogging/walking/jumping on stairs, hills or ground having a grade of greater than, for example, about 3%, (a) number of stair and/or hill steps, which may be categorized, correlated or organized/arranged according to the number of stair and/or hill steps pertaining to, for example, the speed, pace and/or user state of the user (for example, walking, jogging and/or running), (b) number of flights of stairs, (c) ascent/descent distance on stairs and/or hills, (d) pace, (e) ascent/descent on elevators and/or escalators, (f) number of calories burned or expended by walking/running on stairs and/or hills and/or (g) quantify/compare the additional calories expended or burnt from stairs/hills relative to, versus or over level ground, (iii) in the context of swimming, number of strokes, time between strokes, leg kicks and similar metrics (variance of stroke time, mean stroke time, etc.), depth underwater, strokes per lap, lap time, pace and/or distance, (iv) in the context of using a bicycle, wheelchair, skateboard, skis, snowboard, ladder, etc., (a) ascent/descent distance traversed, (b) number of additional calories expended, (c) time of a downward "run" or upward "climb", (d) number of calories expended, (e) number of pedal rotations, (f) arm or wheel rotation, (g) the grade of the surface, (h) pushes, kicks and/or steps. This list of activities (if applicable to the particular embodiment) is merely exemplary and is not intended to be exhaustive or limiting of the inventions to, for example, the precise forms, techniques, flow, and/or configurations disclosed.

The processing circuitry may be discrete or integrated logic, and/or one or more state machines, processors (suitably programmed) and/or field programmable gate arrays (or combinations thereof); indeed, any circuitry (for example, discrete or integrated logic, state machine(s), special or general purpose processor(s) (suitably programmed) and/or field programmable gate array(s) (or combinations thereof)) now known or later developed may be employed to calculate, determine, assess, estimate and/or determine the calorie burn of the user based on sensor data. In operation, the processing circuitry may perform or execute one or more applications, routines, programs and/or data structures that implement particular methods, techniques, tasks or operations described and illustrated herein. The functionality of the applications, routines or programs may be combined or distributed. Further, the applications, routines or programs may be implemented by the processing circuitry using any programming language whether now known or later developed, including, for example, assembly, FORTRAN, C, C++, and BASIC, whether compiled or uncompelled code; all of which are intended to fall within the scope of the present invention.

With reference to FIG. 3A, in one embodiment, the motion sensor may include an accelerometer and pedometer to assess the character of the motion/step and determine the number of user steps. In this embodiment, the output of the accelerometer is analyzed by the pedometer to assess the character of the motion/step and determine the number of user steps. With reference to FIG. 3B, in addition to the accelerometer(s), or in lieu thereof, the motion sensor may include one or more gyroscopes, piezofilms, contact switches, and all combinations thereof, with or without the pedometer. Moreover, motion as inferred through GPS, compasses, wireless methods such as proximity sensing to a reference position/device, and other non-inertial sensing approaches (and their combinations with the aforementioned inertial sensors) may also be employed alone or in conjunction with any of the other configurations and/or techniques. Indeed, all types of sensors and sensing techniques, whether now known or later developed, that generate data which is representative of motion of the user are intended to fall within the scope of the present inventions.

With reference to FIG. 3C, in one embodiment, the altitude sensor may include a pressure sensor (relative/differential or absolute), GPS, barometer, radar, ladder (i.e., laser detection and ranging), and/or infrared proximity sensor. The portable device may also employ wireless signal strength, visual landmark identification, or optical proximity sensing to a known reference position/device to provide data which is representative of elevation. In this regard, the altitude sensor provides data which is representative of the altitude and/or changes in altitude of the user. Indeed, all types of sensors and sensing techniques, whether now known or later developed, that generate data which is representative of the altitude and/or changes in altitude of the user are intended to fall within the scope of the present inventions.

As mentioned above, the processing circuitry employs (i) data which is representative of the altitude and/or changes in altitude and (ii) data which is representative of the motion of the user, to determine, calculate and/or detect energy and/or calorie "burn" of the user. (See, FIG. 2). In one embodiment, the processing circuitry implements algorithms and/or processes data based on the flowchart of FIG. 4A. For example, with reference to FIGS. 4A and 4B, the processing circuitry receives the motion sensor data and determines or calculates the calorie burn based on, for example, the character of the motion/step and the number of user steps. The processing circuitry, using the altitude sensor data, may adjust the calorie burn based on consideration or analysis of the data from the altitude sensor. In this regard, the processing circuitry may assess or determine the type of motion that produces/causes the altitude or change in altitude and, in response thereto, determine or calculate the user state—that is, activity state of the user which temporally coincides with the motion sensor data—for example, walking or running on relatively flat or level ground, traversing stairs, on an escalator or in an elevator, traversing a hill or the like. In response to the user state, the processing circuitry may generate an adjusted calorie burn. Here, the processing circuitry adjusts the calculated calorie burn with a factor that is based on the activity state of the user as determined by the altitude sensor data. Thus, the processing circuitry correlates the (i) data which is representative of the altitude and/or changes in altitude and (ii) data which is representative of the motion of the user, to determine or calculate energy and/or calorie "burn" of the user.

Figure 4A:
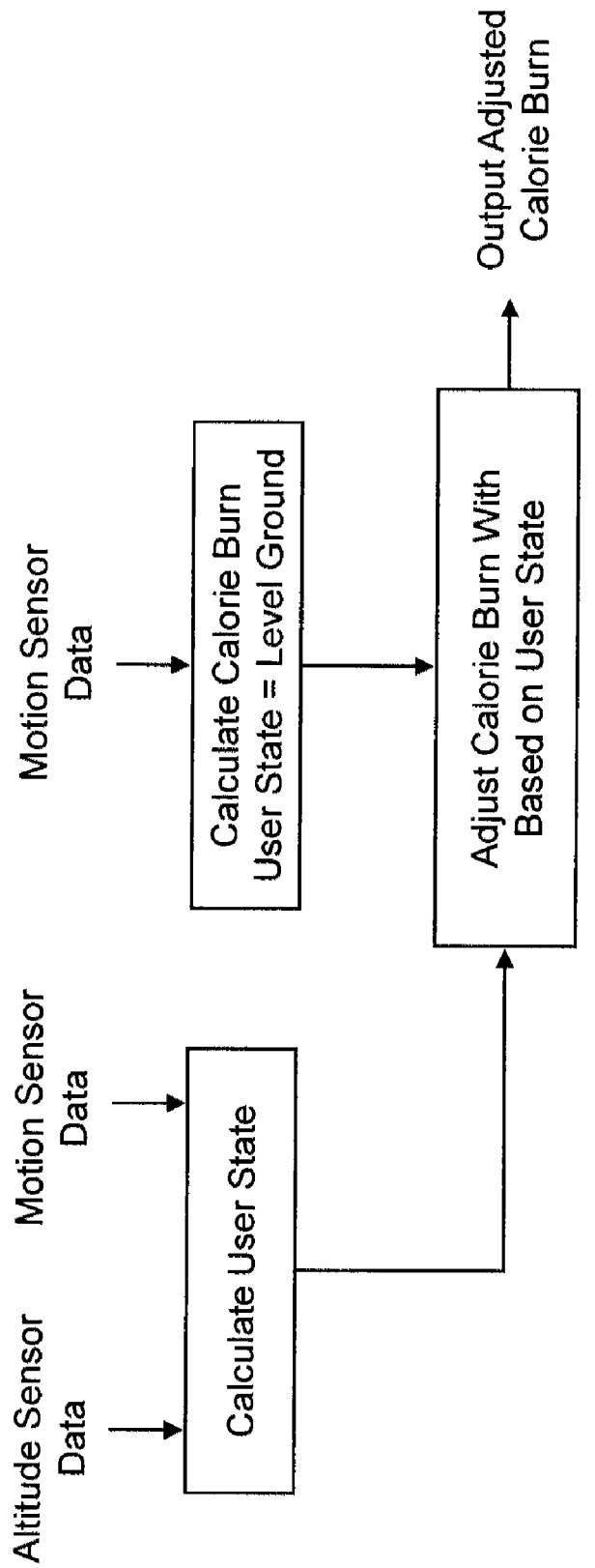
Figure 4B:
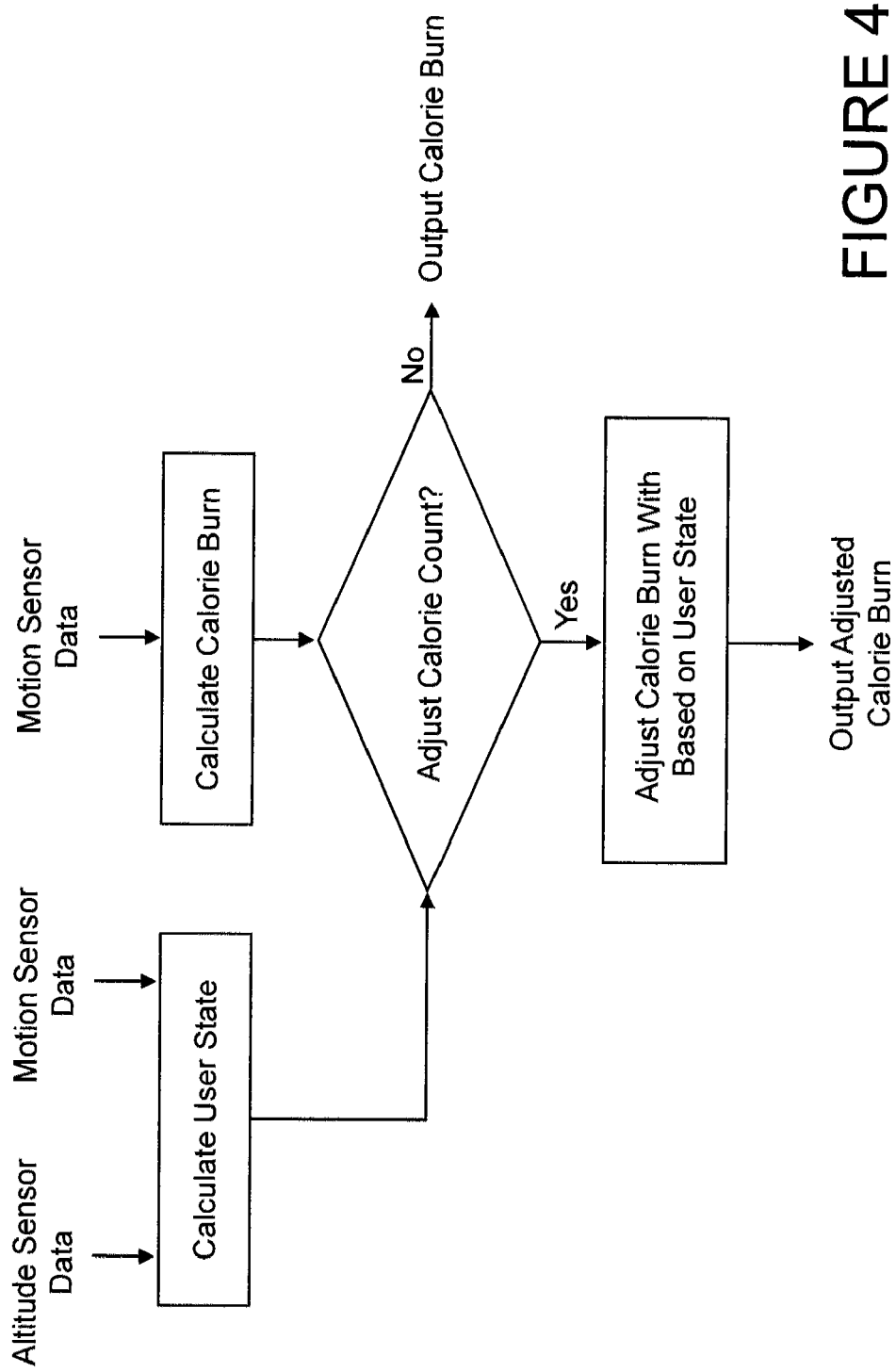
Figure 4C:
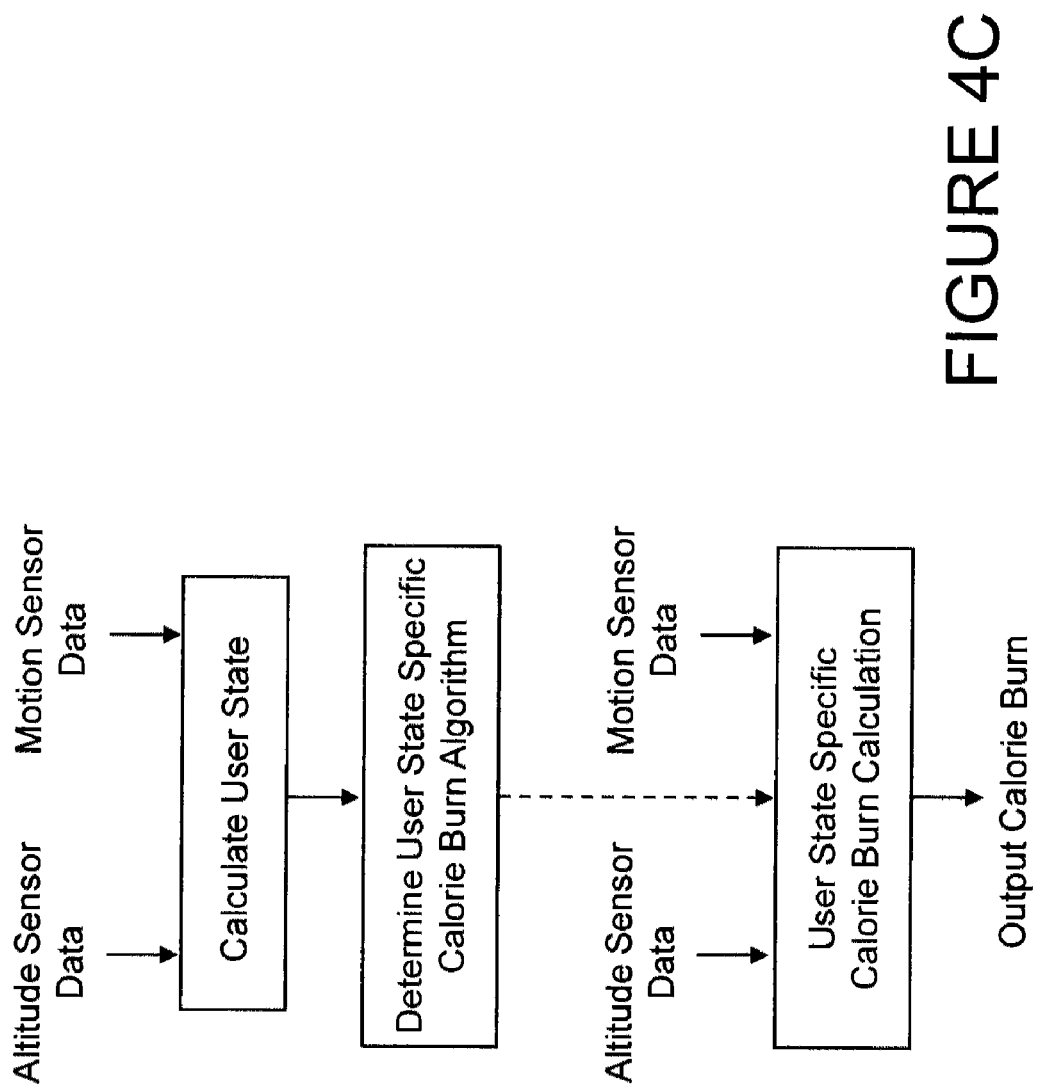
Figure 4D:
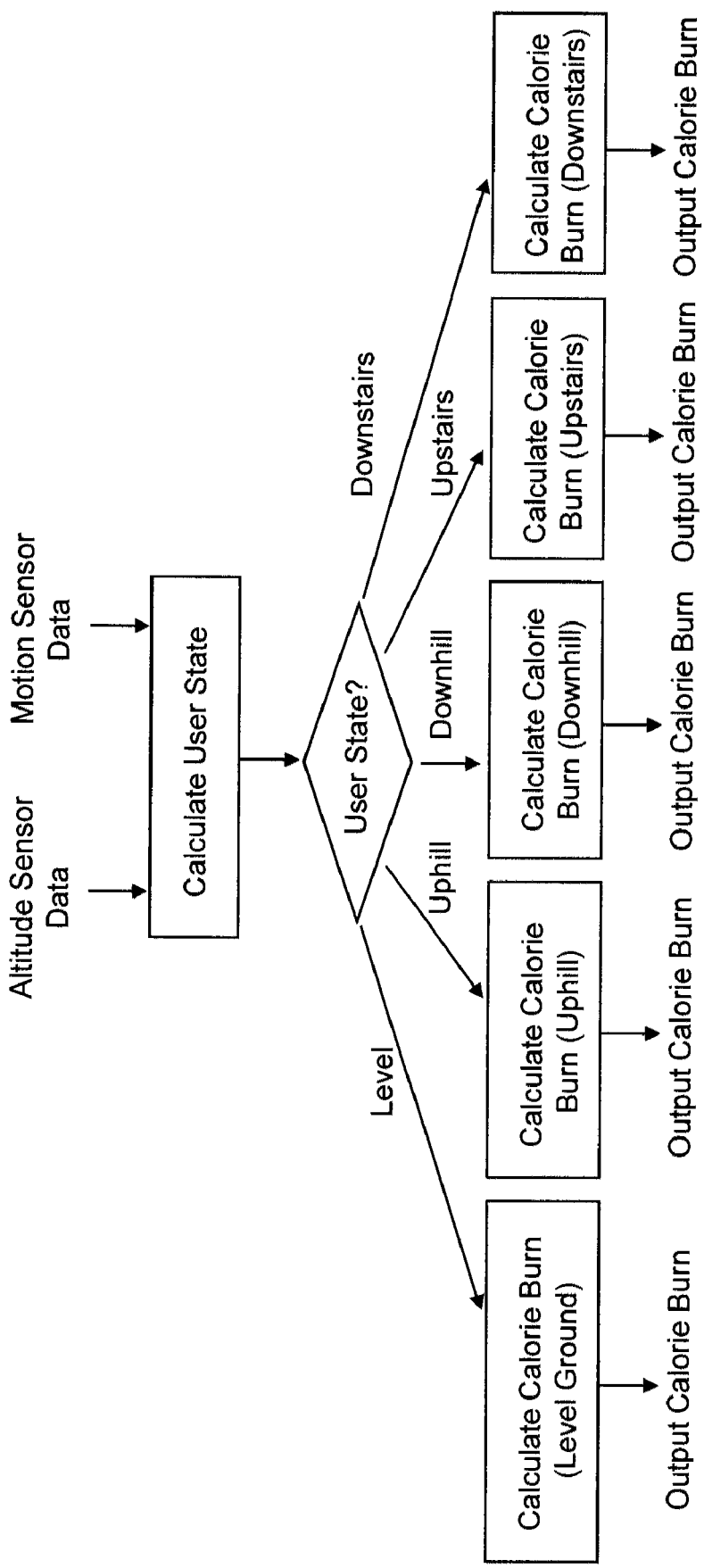

With reference to FIGS. 4C and 4D, in one embodiment, the processing circuitry evaluates (i) data which is representative of the altitude and/or changes in altitude and (ii) data which is representative of the motion of the user, to identify, determine or calculate the user state and, in response thereto, implement a user state specific algorithm or methodology to determine or calculate energy and/or calorie "burn" of the user. For example, where the processing circuitry evaluates such data to determine that the user is traversing a hill, the processing circuitry employs a "hill" specific algorithm to determine or calculate the energy and/or calorie "burn" using the (i) data which is representative of the altitude and/or changes in altitude and (ii) data which is representative of the motion of the user. In this way, the determination or calculation of the energy and/or calorie "burn" may be more accurate in that the specific or dedicated algorithm may employ considerations or features that are "unique" and/or specific to the associated activity; and, as such, the specific or dedicated algorithm may be tailored to the considerations or features that are "unique" and/or specific to the associated activity.

The processing circuitry may calculate, determine and/or estimate calorie consumption, burn and/or expenditure using any technique now known, described herein, and/or later developed. In one exemplary embodiment, the processing circuitry employs a calorie consumption technique that estimates consumption, burn and/or expenditure for walking, running, and lifestyle activities as follows.

Speed-Based Estimation, Calculation and/or Determination

In one embodiment, the processing circuitry may estimate calorie expenditure and activity level based on or using, partially or entirely, the ambulatory speed of the user. For example, with reference to FIG. 5A, in one embodiment, the calorie consumption, burn and/or expenditure is calculated, determined and/or estimated as a function of the speed of the user. Representative energy expenditure rates expressed as metabolic equivalents per minute (MET/min) at different speeds are provided in TABLE 1.

TABLE 1

Exemplary running and walking energy expenditure (MET/min) by speed

| Speed (mph) | Metabolic Equivalents (MET/min) |
| --- | --- |
| Running, 5.0 | 8.0 |
| Running, 5.2 | 9.0 |
| Running, 6.0 | 10.0 |
| Running, 6.7 | 11.0 |
| Running, 7.0 | 11.5 |
| Running, 7.5 | 12.5 |
| Running, 8.0 | 13.5 |
| Running, 8.6 | 14.0 |
| Running, 9 | 15.0 |
| Running, 10.0 | 16.0 |
| Running, 10.9 | 18.0 |
| Walking, 1.86 | 1.5 |
| Walking, 2.24 | 1.9 |
| Walking, 2.61 | 2.4 |
| Walking, 2.98 | 3.2 |
| Walking, 3.36 | 4.0 |
| Walking, 3.73 | 5.0 |
| Walking, 4.10 | 6.4 |

In one embodiment, the speed of the user may be calculated, determined and/or estimated as the user's step count over a time epoch multiplied by one or more step lengths of the user (which may be programmed, predetermined and/or estimated (for example, based on attributes of the user (for example, height, weight, age, leg length, and/or gender))), which may be estimated, obtained (for example, from a look-up table or database) and/or interpolated from the MET table to obtain the user's energy expenditure. In one embodiment, step length may take one of two values that are indicative of a walking and a running step length dependent on the step frequency and/or acceleration characteristics of the user. In a preferred embodiment, step length may be described as a linear function of step frequency:

$$\text{step length} = A + B * \text{step frequency},$$

where A and B are parameters that may be associated with or calibrated to the user; notably, such parameters may be stored in memory in the portable monitoring device.

In another embodiment, step length may be described as a function of step frequency and characteristics of the user acceleration:

$$\text{step length} = A + B * \text{step frequency} + C * \text{variance of acceleration},$$

where A, B, and C are parameters that may be calibrated to the user; notably, such parameters may be stored in memory in the portable monitoring device.

In yet another embodiment, step length may be obtained, acquired and/or determined via a look-up table or database, or interpolated (e.g., spline interpolation, neural network) between known (step frequency, step length) pairs or (step frequency, acceleration variance, step length) triplets that have been predetermined or specified by the user and/or pre-programmed or calibrated using the device. For example, the user may start an annotated walking or running sequence on the portable monitoring device, then specify the distance traveled either on the device or through another service (e.g., www.fitbit.com), which may be employed to calibrate or reference for the device by one or more of the following:

estimating the regression coefficients (A, B) or (A, B, C),
calculating a walking and/or running step length, and
building a lookup table for (step frequency, step length) or (step frequency, acceleration variance, step length).

In addition thereto, or in lieu thereof, the user may calibrate the portable monitoring device by attaching the device to the foot of the user and placing the device into an annotated foot-mounted mode in which speed and distance are tracked and need not be entered by the user. In this mode, the portable monitoring device also acquires data which is representative of, for example, the user's step frequency, acceleration variance, step length. Likewise, distance may be derived from other sources such as a GPS-enabled mobile device, a software mapping utility, or other distance tracking device (e.g., Nike+) and employed to determine the step frequency, acceleration variance, and step length of the user. Under certain conditions, in the absence or interruption of GPS signal, the combination of user altitude over time, two or more geophysical positions on a map and the times at which the user was there, a corresponding altitude map, and the distance over time of the user may be used to estimate the complete route traveled by the user.

Although, in the preceding examples, the step length has been characterized, expressed and/or estimated as a linear function of one or more parameters such as step frequency and variance of acceleration, the step length and other parameter may be characterized, expressed and/or estimated to a higher order or different functional form. Accordingly such parameters may be expressed as polynomial functions, transcendental functions, etc. as well and may include other input variables such as elevation change (as discussed in detail herein). Indeed, the function need not be monotonically increasing or monotonically decreasing, as implied by the preceding illustrative linear functions. Additionally, different equations may be employed for specific activity states or operating modes (e.g., walking, running, jumping, speed walking).

The speed value may be converted to calorie expenditure by multiplying the corresponding MET value by the user's BMR. BMR may be obtained through any of a number of well-known equations based on height, weight, gender, age, and/or athletic ability or through designated BMR measurement devices. For example, a user may have a running step length of 57 inches and take 180 running steps during 1 min. Using the method described above, the user's speed estimate is 9.8 miles per hour, which may be linearly interpolated to provide a BMR value of 15.8 MET from the MET table above. Assuming the user's BMR to be 1.10 kcal/MET, the calorie burn of the user in the preceding minute is 17.4 kcal. For the avoidance of doubt, this description is intended to be exemplary.

Speed estimation may be determined using a different time epoch or a plurality of time epochs. Multiple step lengths may be used. The MET table may be calibrated to the specific user and/or may be expressed as a function of speed in some method, such as an analytical function, discontinuous function, or otherwise. For example, in one embodiment, the relationship between speed and calories may be expressed as:

$$\text{cal\_speed}=(A+B*\text{speed})*\text{time}*\text{BMR},$$

where speed is the speed of the user, time is the length of time under consideration, and (A,B) are parameters that may be calibrated to the user; notably, such parameters may be stored in memory in the portable monitoring device.

Likewise, it is noted that an intermediate MET calculation step is not required in this and similar methods. Calorie expenditure may be calculated directly based on speed and one or more physiological parameters of the user such as age, gender, height, weight, and/or athletic ability. Speed may also be filtered over time rather than accepted as a "raw" measurement for a given time epoch.

FIG. 5B illustrates another embodiment in which the portable monitoring device may calculate, estimate and/or determine the speed of the user based on linear and angular acceleration measurements from, for instance, the foot. Linear acceleration may be obtained from one or more accelerometers. Angular acceleration may be obtained by one or more accelerometers, one or more gyroscopes, and/or one or more orientation sensors (e.g., compass).

Notably, the portable monitoring device may employ such techniques as those set forth in U.S. Pat. Nos. 6,513,381 and/or 5,724,265. Alternatively, the portable monitoring device may employ the techniques set forth in U.S. Pat. Nos. 4,578,769 and 6,018,705 wherein the device is mounted to the foot of the user and the speed of the user may be estimated by the time of contact of the foot on the ground.

In one embodiment, the speed of the user may be determined, calculated and/or estimated from the signal energy from a motion sensor in the following form:

$$\text{speed}=A*\log(\text{energy})+B$$

where (A,B) are parameters that may be estimated or associated with and/or calibrated or tuned to an individual (for example, based on the physical or motion attributes of the user); notably, such parameters may be stored in memory in the portable monitoring device.

In yet another embodiment, the portable monitoring device (or associated device) may be location aware and the travel that coincides with motion detected by the motion sensor may be used to estimate speed. For example, the portable monitoring device may include or incorporate GPS to determine its location, or communicate with a GPS-enabled device to receive data which is representative of location or change in location (absolute or relative location data). In addition thereto, or in lieu thereof, the portable monitoring device may communicate wirelessly with RF location beacons to determine position and/or change in position. Indeed, the portable monitoring device may also use signal strength to the beacons to determine or estimate position and/or change therein.

In one embodiment, the portable monitoring device includes a camera (or communicates with a device that includes a camera). In this embodiment, the portable monitoring device may determine location visually by recognizing location landmarks and/or features.

Notably, the aforementioned location sensors and methods may also be used to infer user altitude. For example, the user's location as determined by GPS may enable altitude estimates when combined with an altitude map. GPS itself may also provide altitude measurements. Wireless communications may also be used to determine altitude. For example, a RF location beacon may be programmed with its altitude and the portable monitoring device may use any of a number of well known methods for three-dimensional point locating such as multilateration and trilateration.

Notably, the present inventions not intended to limit the method or means by which speed may be calculated, estimated and/or determined. Indeed, all forms of speed estimation, and mechanisms to implement such techniques, whether now known, described herein, a combination and/or fusion of the methods described herein, and/or later developed may be employed or implemented and, as such, are intended to fall within the scope of the present inventions.

Accelerometry for Calorie Estimation, Calculation and/or Determination

In addition to speed based techniques, or in lieu thereof, the portable monitoring device may estimate, calculate and/or determine, calorie consumption, burn and/or expenditure using data which is representative of the intensity of user motion—for example, as provided or determined by one or more single axis or multi-axis accelerometers. In one embodiment, the signals from the one or more accelerometers may be filtered using time domain or frequency domain filtering techniques to produce a parameter indicative of the intensity of user motion, often referred to as a "count". A count may be computed as the sum of the rectified filtered accelerometer output taken over a suitable time epoch, for example, 10 sec, with or without additional processing such as thresholding and/or saturation. The portable monitoring device may calculate, determine and/or estimate calorie consumption, burn and/or expenditure as a function of the current count value or a sequence of count values. For example, the portable monitoring device may calculate, determine and/or estimate calorie consumption, burn and/or expenditure using one or more of the following techniques:

$$\text{MET}=(A+B*\text{count})*\text{time},$$

$$\text{MET}=(A+B*\text{count}+C*\text{count}^2+D*\text{count}^3+\ldots)*\text{time},$$
and $$\text{MET}=(A*\exp(B*\text{count}))*\text{time},$$

which are, respectively, linear, polynomial, and exponential relationships between counts and calorie expenditure expressed in METs.

Notably, the preceding equations may likewise be expressed directly in terms of kilocalories through the inclusion of one or more physiological parameters such as the user's age, gender, height, weight, and/or athletic ability (wherein such parameters may also be set to default values). A representative example is the following:

$$cal=((A+B*age+C*gender+D*weight+E*height+F*athleticism)*count)*time.$$

Indeed, all accelerometry methods, whether now known or later developed, that generate data which is representative of the calorie burn of the user are intended to fall within the scope of the present inventions.

Heart Rate for Calorie Estimation, Calculation and/or Determination

In addition to speed based techniques and/or acceleration based techniques, or in lieu thereof, the portable monitoring device may estimate, calculate and/or determine calorie consumption, burn and/or expenditure using or based on a heart rate of the user. For example, in one embodiment, the portable monitoring device may estimate, calculate and/or determine calorie consumption, burn and/or expenditure as follows:

$$cal=(A*HR+B)*time,$$

where HR is heart rate, time is the length of time under consideration, and
 A and B are parameters that may be adjusted or calibrated to the user based on, for example, the user's height, weight, age, gender, and/or athletic ability; notably, such parameters may be stored in memory in the portable monitoring device.

In one embodiment, the portable monitoring device may estimate, calculate and/or determine calorie consumption, burn and/or expenditure using a plurality of equations. For instance, at low or normal heart rates, it may be desirable to use one form of the above equation with parameters (A1, B1) and at higher heart rates, it may be desirable to use the above equation with parameters (A2, B2).

"Combined" Calorie Consumption Estimation, Calculation and/or Determination

As indicated above, the portable monitoring device may estimate, calculate and/or determine calorie consumption, burn and/or expenditure using a combination of the techniques described herein. For example, with reference to FIG. 4P, the portable monitoring device may employ motion data and heart rate data to estimate, calculate and/or determine calorie consumption, burn and/or expenditure. In this exemplary embodiment, under certain criteria such as low or normal heart rate in the absence of user steps, calorie burn is calculated, determined or estimated (for example, solely) using data which is representative of accelerometry while under other criteria such as elevated heart rate in the absence of user steps, calorie burn is calculated, determined or estimated (for example, solely) using data which is representative of the heart rate, otherwise calorie burn is calculated, determined or estimated using data which is representative heart rate, speed, and accelerometry. An example would be the following equation:

$$cal\_total=(p1*cal\_HR+p2*cal\_speed+p3*cal\_accelerometry)*time,$$

where cal_HR is the calorie estimate derived solely from heart rate, cal_speed is the calorie estimate derived solely from speed, and cal_accelerometry is the calorie estimate derived solely from accelerometry, time is the length of time under consideration, and pi (1, 2, 3) are either fixed parameters or dynamically adjusted parameters indicative of the certainty and/or quality of the preceding calorie estimates.

As such, the portable monitoring device may estimate, calculate and/or determine calorie consumption, burn and/or expenditure based on:

$$cal\_total=f(heart\ rate\ data, motion\ data, mode\ data, time\ data),$$

where f(•) is an arbitrary function that employs, fuses and/or implements information from the heart rate, motion, mode, and/or time, when such data is present and desirable or required.

In this context, information includes heart rate, heart rate variability, respiration as obtained as a modulated signal in an optical heart rate sensor, acceleration (raw, filtered, rectified, etc.), steps, speed, type of activity (e.g., bicycle, swimming, running, sleeping, sitting), surface slope, stairs, etc.

Notably, the aforementioned expression is intended to describe the case in which a plurality of equations are maintained and the portable monitoring device employs or selects a suitable, correct or predetermined equation is depending on, for example, the heart rate and/or motion as measured by the motion sensor and/or mode sensor.

The portable monitoring device may be mounted on or to different locations on the body of the user and/or exercise equipment and provides different capabilities based on its body location. In one embodiment, the portable monitoring device may obtain or determine its body location through a user input, a mode sensor that senses its body location and/or the presence of or coupling to a mounting or attachment mechanism or system (for example, which provides information to the device which indicates a mode).

In addition thereto, or in lieu thereof, the portable monitoring device may determine its body location automatically based on the signals derived from its other sensors. For example, the motion as observed by the accelerometer and/or gyroscope and/or compass and/or altimeter may be indicative of the device being mounted or affixed to the user's foot, hip, chest, back, or on the user's bicycle hub or wheelchair wheel. Moreover, an optical heart rate sensor may provide information (for example, supplementary information) to determine if the portable monitoring device is in contact with the user's skin and able to observe cardiac signal or otherwise in contact with a housing and/or mounting device. FIG. 4Q illustrates an exemplary flow to calculate, estimate and/or determine calorie burn in such a system/technique. Notably, the portable monitoring device may calculate other parameters (in addition to or in lieu of calorie burn) which are not depicted in FIG. 4Q and that are specific to the activity/mode that the device is currently in (for example, number of steps and/or stairs, number of stair flights, elevation gain/loss from ambulatory and/or non-ambulatory locomotion, absolute elevation, activity intensity, distance traveled and/or pace, number of swim strokes and/or kicks, strokes per lap, lap time, pace and/or distance, number of pedal rotations of a bicycle, arm or wheel rotation of a wheelchair, heart rate, heart rate variability, respiration rate, stress levels, skin temperature, body temperature). Calorie burn may be determined in a multitude of ways not depicted here. For example, the calories burned during swimming may be expressed as:

$$cal\_swim=(A+B*speed)*time,$$

where speed is the swimming speed of the user, time is the length of time under consideration, and (A,B) are parameters that may be associated with and/or calibrated or tuned to the user; notably, such parameters may be stored in memory in the portable monitoring device.

Where the portable monitoring device determines or is instructed that the user is swimming, speed may be calculated as the length of the pool divided by the time taken to cover that distance; from which an average distance traveled per stroke (as observed by the motion sensor) may be calculated, estimated and/or determined and subsequent calculations or estimates of speed may be determined by the observance of swim strokes in real-time:

$$cal\_swim = A + B*stroke,$$

where stroke is the stroke count of the user and (A,B) are that may be associated with and/or calibrated or tuned to the user; notably, such parameters may be stored in memory in the portable monitoring device. Different or multiple equations may be employed to account for different swimming stroke types.

Calorie burn may also be calculated roughly as a function of one or more of the following variables: stroke type, lap count, and swimming duration.

Where the portable monitoring device determines or is instructed that the user is bicycling, calorie burn may be calculated, estimated and/or determined by:

$$cal\_bike = (A + B*cadence)*time,$$

where cadence is the number of foot pedal rotations of the user over a time epoch, time is the length of time under consideration, and (A,B) are that may be associated with and/or calibrated or tuned to the user; notably, such parameters may be stored in memory in the portable monitoring device.

Augmentation Using Altitude Data

In other embodiments, the portable monitoring device augments and/or adjusts the estimation, calculation and/or determination of calorie consumption, burn and/or expenditure, using or based on altitude related information (for example, from an altimeter disposed on the portable monitoring device). In these embodiments, the portable monitoring device may employ the speed-based calorie consumption, burn and/or expenditure techniques described herein in conjunction with altimeter or altitude (or change in altitude) related information. For example, in the MET-table based approach disclosed herein, the resulting calorie output may be expressed, characterized, determined, calculated and/or estimated as:

$$cal = (MET(speed)*k1(\Delta H-S))*time*BMR,$$

or $$cal = (MET(speed) + k2(speed, \Delta H-S))*time*BMR,$$

or $$cal = (MET(speed)*k1(\Delta H-S) + k2(speed, \Delta H-S))*time*BMR,$$

where MET(speed) is the nominal calorie output over flat land as a function of speed, k1(–H–S) and k2(speed, ΔH–S) are a scaling and offset term that are functions of ΔH–S (i.e., the change in elevation per step) and/or speed, and time is the length of time under consideration. k1(ΔH–S) and k2(speed, ΔH–S) are parameters or functions that may be tuned to the user.

In another embodiment, calorie burn may be expressed or characterized as (and determined, calculated and/or estimated using) a linear function of speed and as a function of ΔH–S:

$$cal = ((A + B*speed)*k1(\Delta H-S) + k2(speed, \Delta H-S))*time*BMR,$$

where (A,B) are parameters are that may be associated with and/or calibrated or tuned to the user, and time is the length of time under consideration; notably, such parameters may be stored in memory in the portable monitoring device.

In the preceding equations, the terms dependent on ΔH–S may equivalently be written as functions of the surface slope or grade by substituting the distance traveled per step. Notably, this may be a more natural expression when speed is calculated by means other than step counting as in, for instance, foot-mounted speed and distance tracking or GPS:

$$cal = (MET(speed)*k1(slope) + k2(speed, slope))*time*BMR,$$

or $$cal = ((A + B*speed)*k1(slope) + k2(speed, slope))*time*BMR.$$

The preceding two equations are equivalent to adjusting the calorie burn estimate obtained on a level surface, adjusted with an additive and/or multiplicative factor that is dependent on user slope and/or speed.

Furthermore, step length may be written as a function of step frequency, ΔH–S, or characteristics of the user acceleration (or combinations therein). For instance, $$step\ length = A + B*step\ frequency + C*variance\ of\ acceleration + D*\Delta H-S,$$

where (A,B,C,D) are parameters. These parameters may be tailored to an individual based on the calibration methods described above or equivalent techniques.

In one embodiment, the altitude correction to energy expenditure may be an additive term calculated as:

$$dcal = k*speed*grade*BMR.$$

This equation naturally accounts for reduced energy expenditure when going downhill (i.e., grade<0) and increased energy expenditure when going uphill (i.e., grade>0). However, energy expenditure may also increase when going down steep grades in excess of roughly 0.10. In such cases, the altitude correction term may be adapted with an offset and different multiplication constant k. Indeed, in a variety of scenarios, the correction term may be adapted with offsets and multiplication constants that are appropriate for the given activity state and/or mode (e.g., running, walking, jumping, etc.).

Certain numerical simplifications may be used to reduce the number of computations performed on the portable monitoring device. For instance, by observing that the speed over a time epoch may be estimated as the number of user steps multiplied by the user's step length and the surface grade may be approximated as the change in user elevation divided by the change in user horizontal distance, the preceding additive adjustment term may be calculated as:

$$dcal = k'*steps*\Delta H-S*BMR.$$

Notably, all such mathematical manipulations of the preceding methods that yield identical or substantially equivalent results are considered within the scope of the present inventions.

Notably, in one embodiment, if ΔH–S exceeds a predetermined threshold, the processing circuitry may determine that the user is traversing stairs, in which case, specific stair estimation algorithms may be employed. With reference to FIG. 4R, the processing circuitry may employ an embodiment in which upstairs walking and running are given specific calorie burn algorithms based on ΔH–S. Downstairs logic may be incorporated therein. Likewise, specific equations and/or logic may be employed for different grade hills, both upwards and downwards in accordance with the preceding linear equations, or alternate nonlinear equations and means (e.g., lookup tables, polynomials, transcendentals, interpolations, neural nets, maximum likelihood estimates, expected value estimates, etc.).

For example, in the context of running/walking on stairs, hills or ground having a grade of greater than about 2-3%, the algorithm, determination or calculation of the energy and/or calorie "burn" may employ such considerations or factors as number of stair and/or hill steps, surface grade, ascent/descent distance on stairs and/or hill, pace thereof, ascent/descent on elevators. Indeed, in the context of swimming, the algorithm, determination or calculation of the energy and/or calorie "burn" may employ such considerations or factors as number of strokes, time between strokes and similar metrics (variance of stroke time, mean stroke time, etc.), depth underwater, stroke type, strokes per lap, lap time, pace and/or distance. Further, in the context of using a bicycle, wheelchair, skateboard, skis, snowboard, ladder, etc., the algorithm, determination or calculation of the energy and/or calorie "burn" may employ such considerations or factors as ascent/descent distance traversed, number of additional calories expended, time of a downward "run" or upward "climb", number of calories expended, number of pedal rotations, arm or wheel rotation, the grade of the surface, pushes, kicks and/or steps.

Figure 4E:
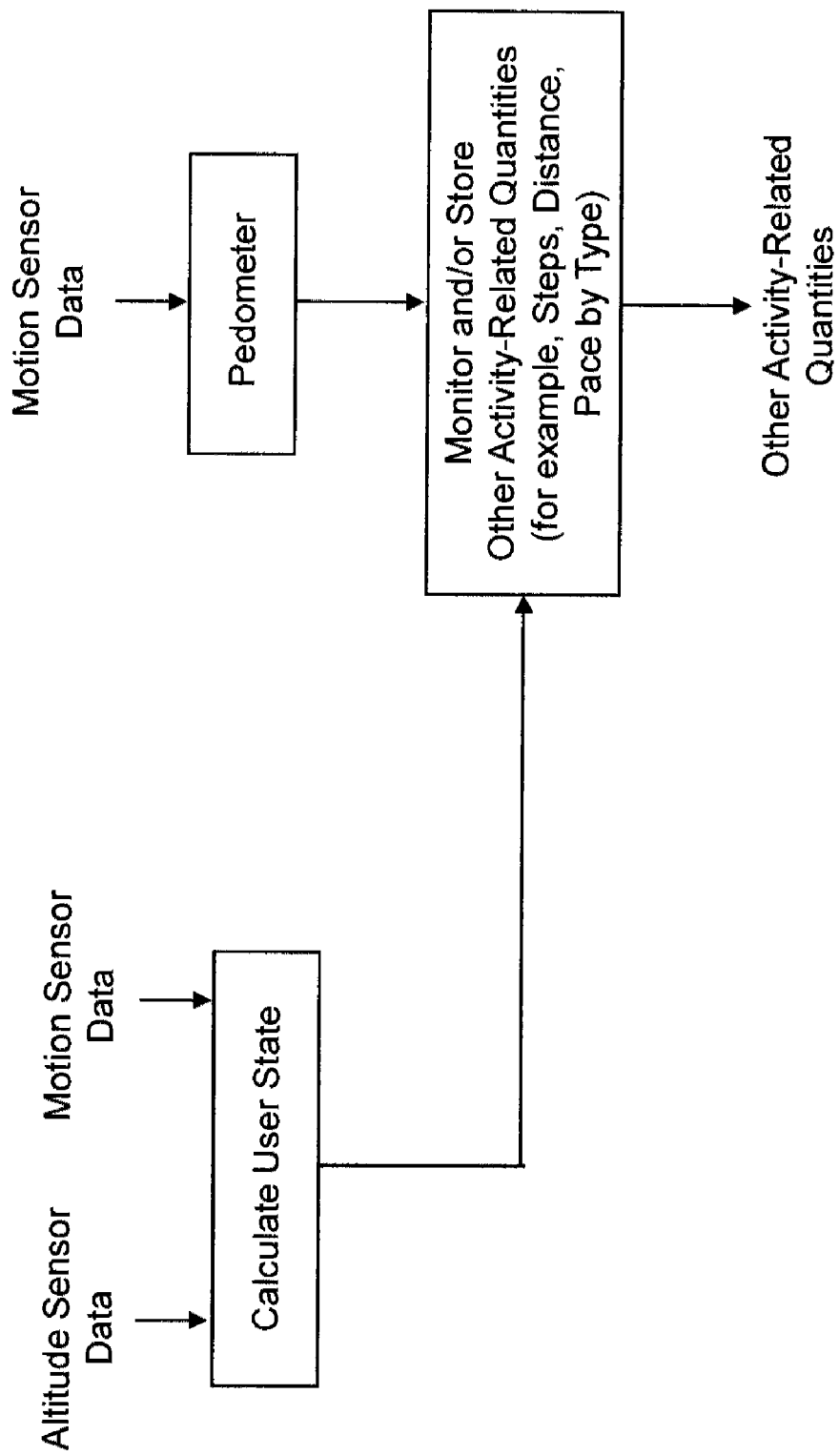
FIGS. 4E and 4G are flowcharts of exemplary processes for calculating, obtaining, assessing and/or determining other activity-related metrics including, for example, steps taken by the user based on certain sensor data, according to certain aspects of the present inventions.

As intimated above, data which is representative of the altitude and/or changes in altitude and data which is representative of the motion of the user may also be used to determine and/or classify other activity-related metrics such as, for example, user steps, distance and pace (FIG. 4E). For example, user distance may be calculated as the number of user steps multiplied by the user's step length, which in turn is calculated as a function of $\Delta H$–S and/or the change in altitude over time ("$\Delta H$–t"). Notably, other activity-related metrics may be determined by the processing circuitry, including, for example, (i) in the context of running/walking on level or substantially level ground, number of steps, also broken down as walking or running, distance traveled and/or pace (ii) in the context of running/walking on stairs, hills or ground having a grade of greater than about 3%, number of stair and/or hill steps, which may be categorized or broken down, correlated or organized/arranged according to, for example, the speed, pace and/or activity state of the user (for example, as walking, jogging or running), number of flights of stairs, ascent/descent distance on stairs and/or hills, pace, ascent/descent on elevators and/or escalators, surface grade, and/or number of calories expended by walking/jogging/running on stairs and/or hills as well as quantify/compare the additional calories burnt from stairs/hills over level ground.

Figure 4F:
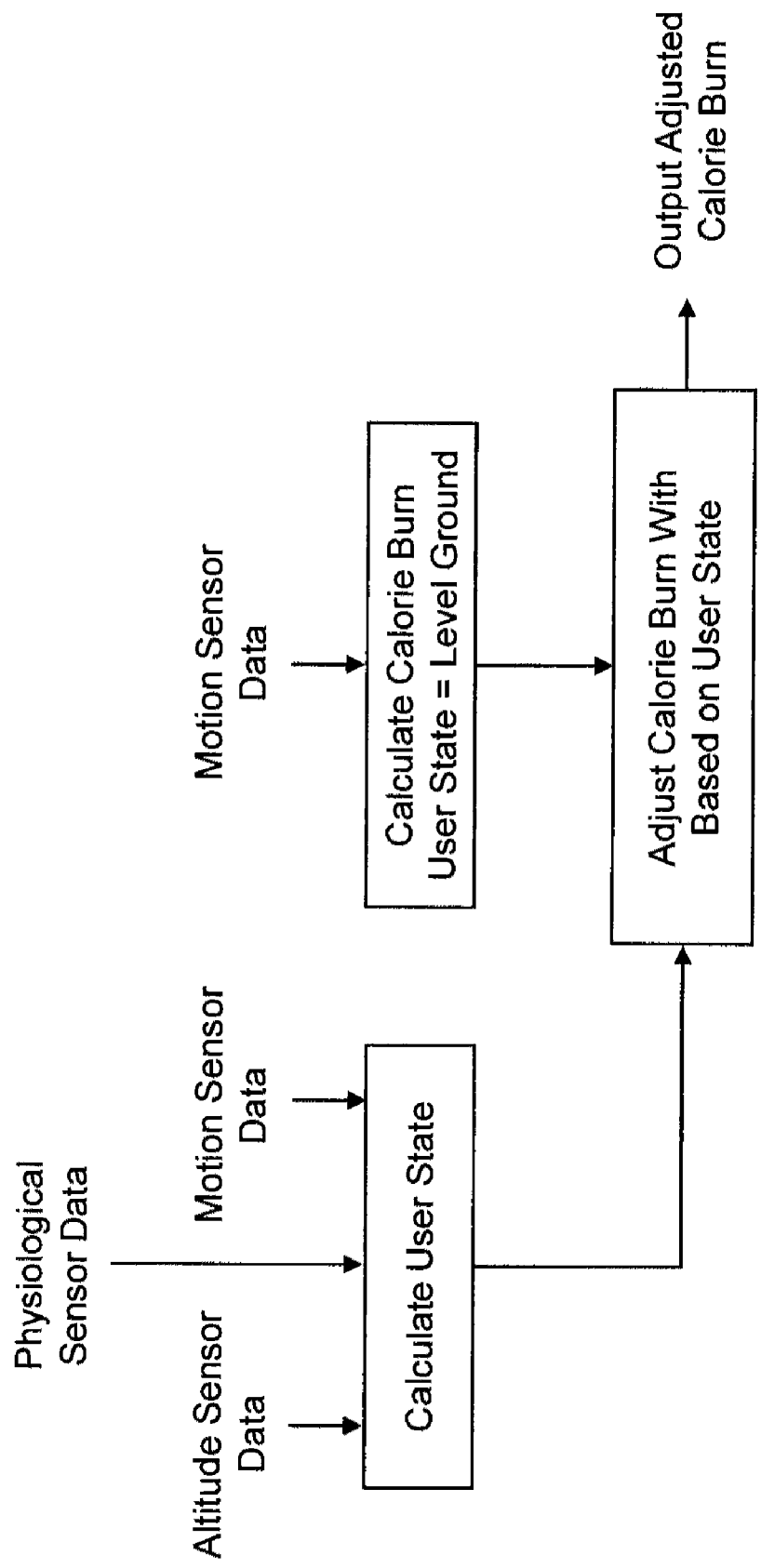

In another embodiment, data from one or more physiological sensors may be employed, alone or in combination with data of the motion sensor(s) and altitude sensor(s), to determine or assess the user state. (See, for example, FIGS. 4F and 4O). As discussed in more detail below, physiological sensor(s) determine, sense, detect, assess and/or obtain information which is representative of physiological condition and/or information of the user (for example, blood pressure, pulse rate, blood sugar and the waveform shape corresponding to the heart beat). Such an embodiment may, among other things, enhance the accuracy of identifying the user state and/or improve the confidence of the correctness/accuracy of the identified user state.

Figure 4G:
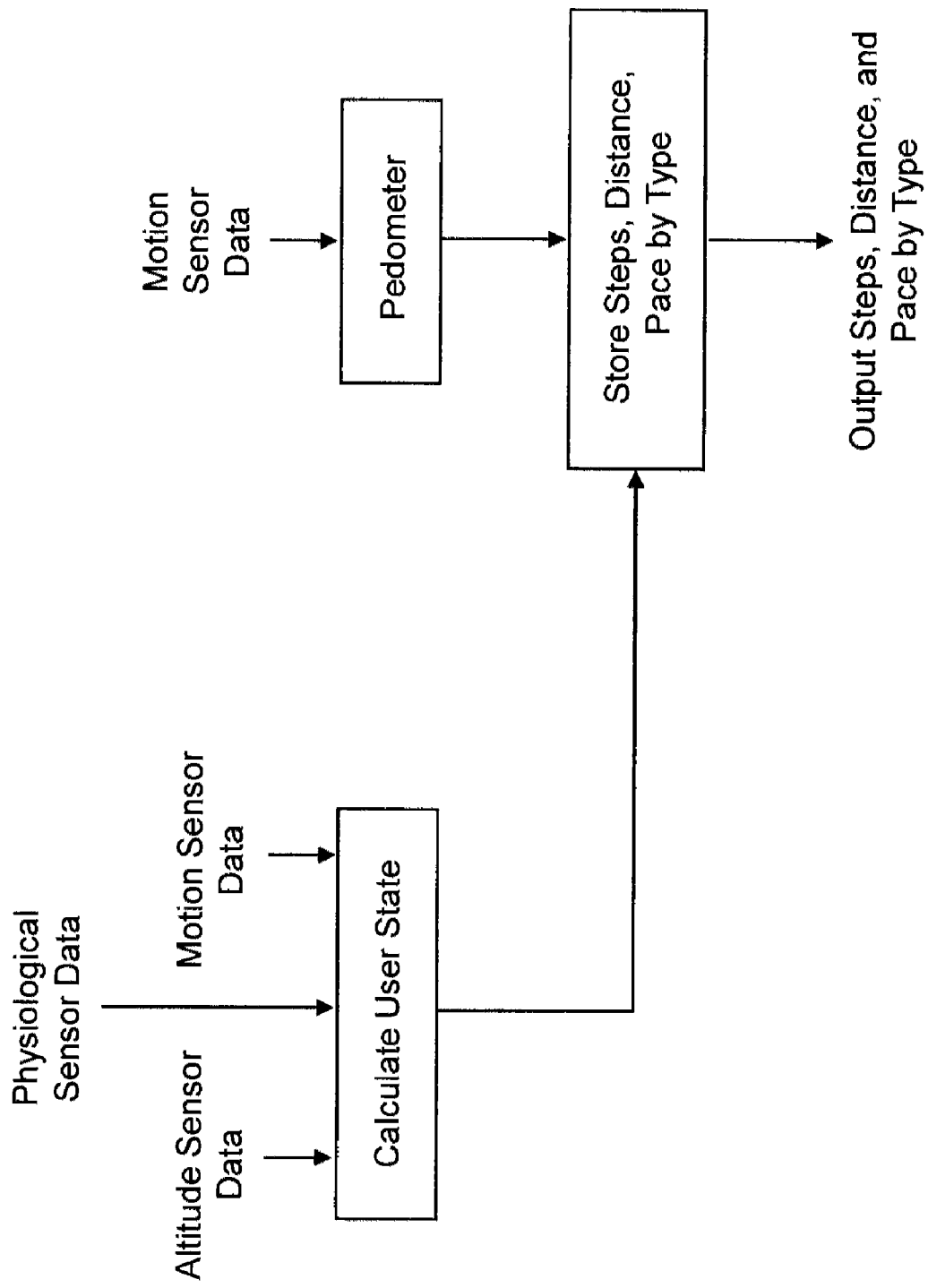
Figure 4H:
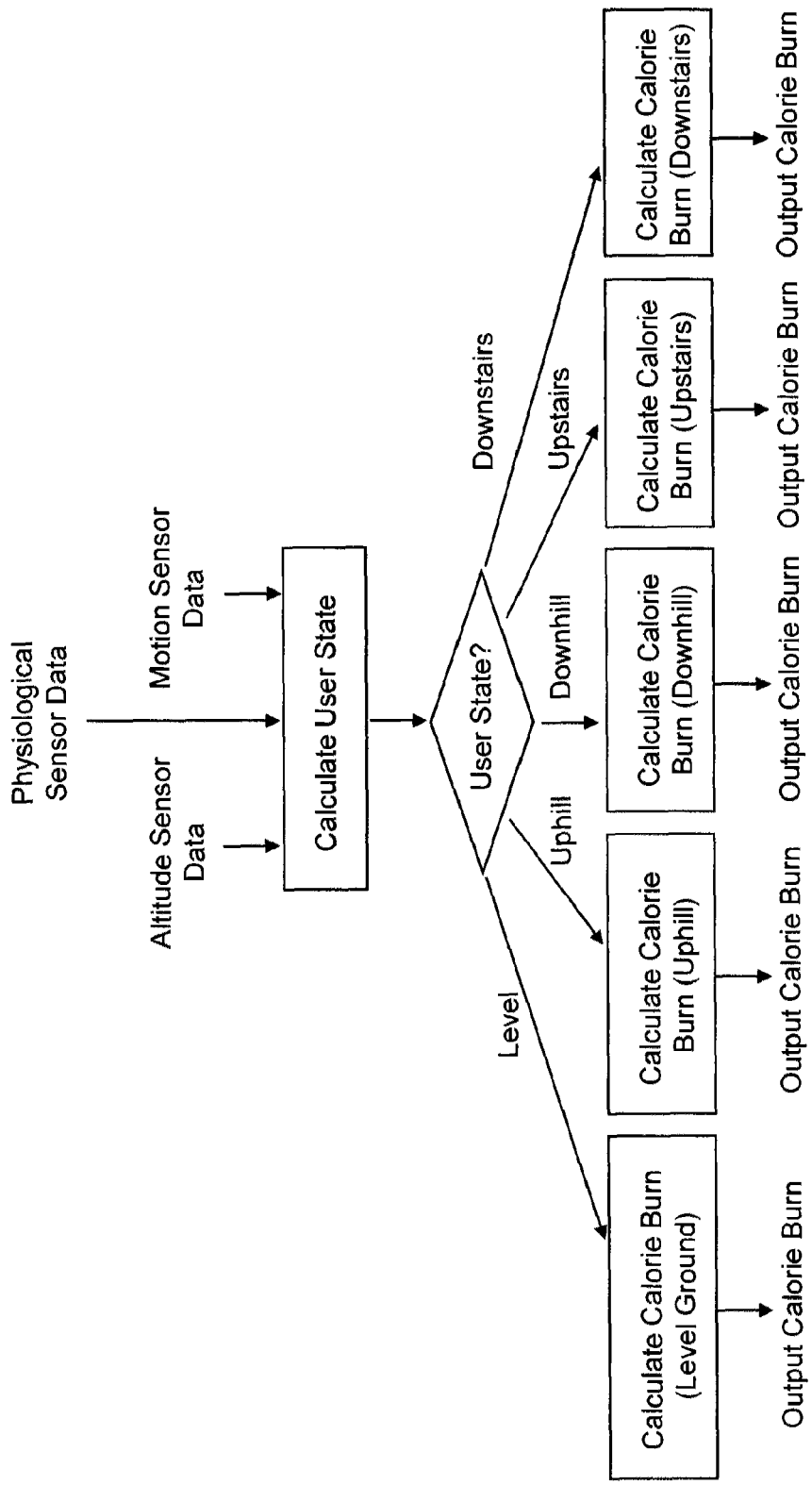
Figure 4I:
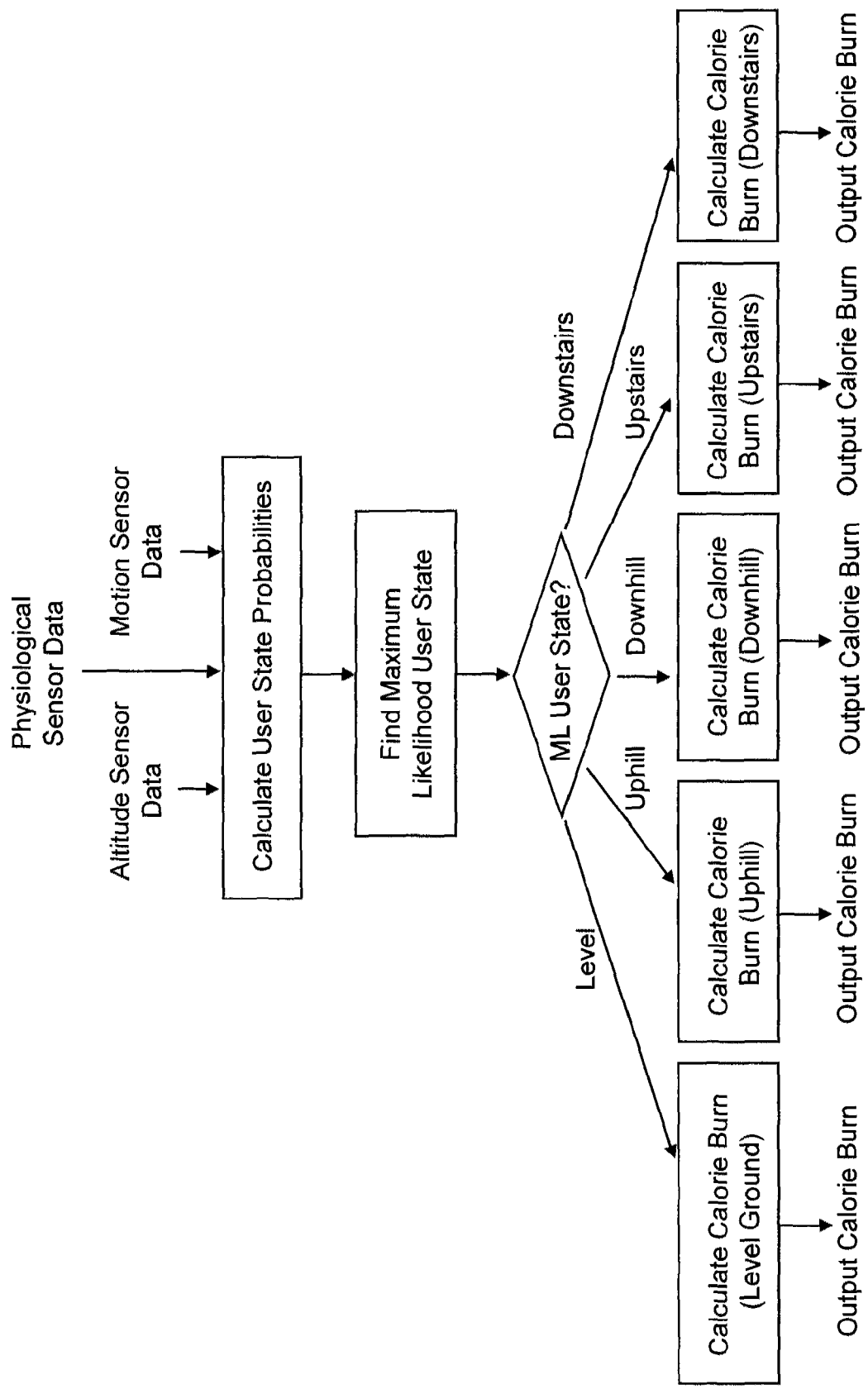
Figure 4J:
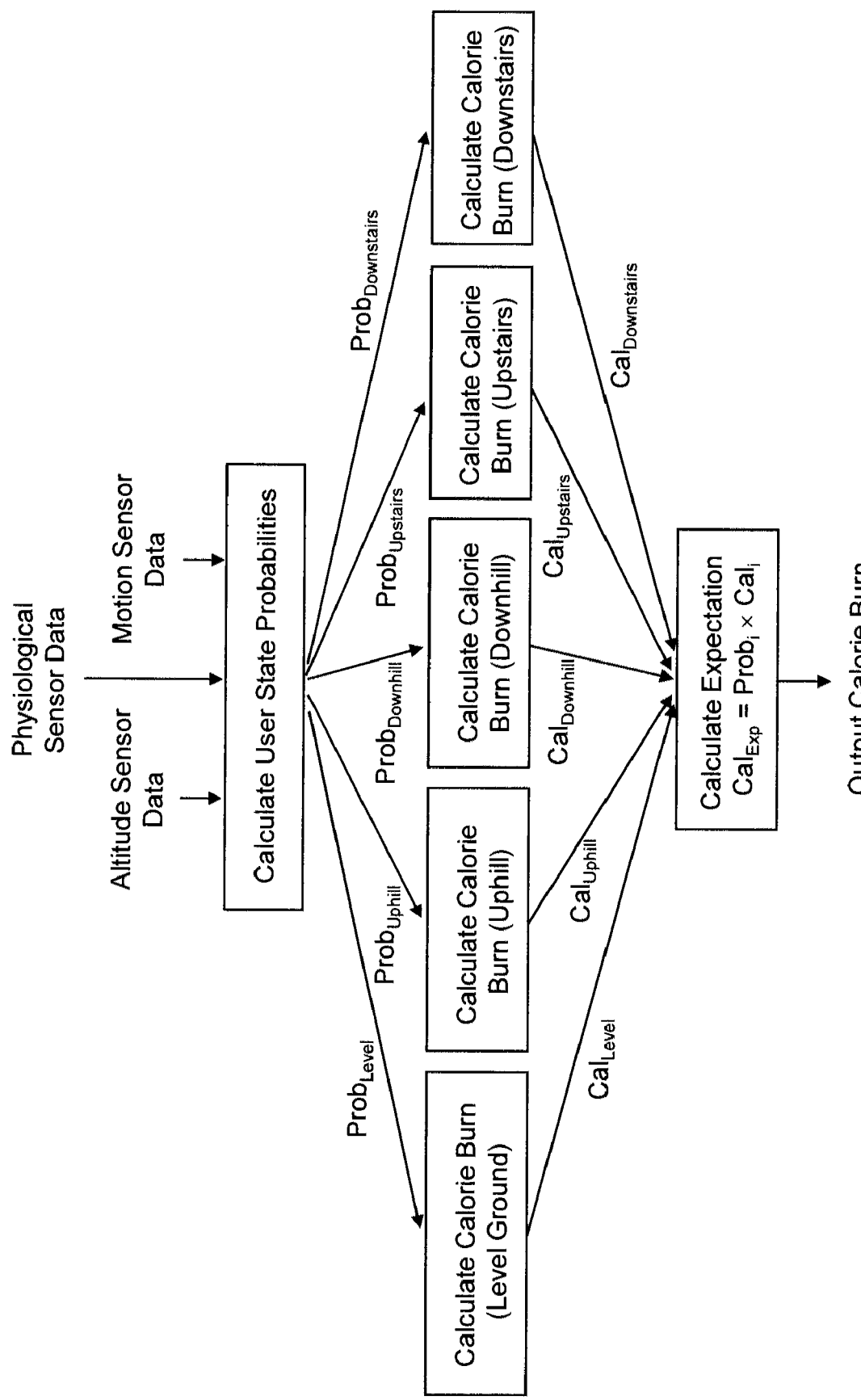

The data from the altitude, motion and physiological sensors may also be used to determine, calculate, estimate, improve and/or classify other activity-related metrics such as, for example, user speed and distance (FIG. 4G). Indeed, the same sensor combinations may also be used to determine, identify and/or classify the user state in order to select the appropriate activity quantification algorithm—see, for example, FIG. 4H wherein calorie burn corresponding to level ground, up/down hill, up/down stairs walking or running. Likewise this set or subset of sensors may be used to estimate and/or calculate the probability of each user state, which may then be used to select the activity quantification algorithm with maximum likelihood (see FIG. 4I or 4M) or merged together to provide the expected value (see FIG. 4J or 4N). A number of methods may be devised to implement each of the embodiments shown in FIGS. 4A-4J and 4M-4R, including but not limited to, iterative and batch algorithms that use ad hoc logic, statistical filtering and classification techniques, neural networks, k-means classifiers, and decision trees. Such conventional techniques or methods may be implemented in the present inventions or adaptively modified as they are used in the invention. As such, these embodiments of the inventions are merely exemplary and are not intended to be exhaustive or limiting of the inventions to, for example, the precise forms, techniques, flow, and/or configurations disclosed.

Figure 4K:
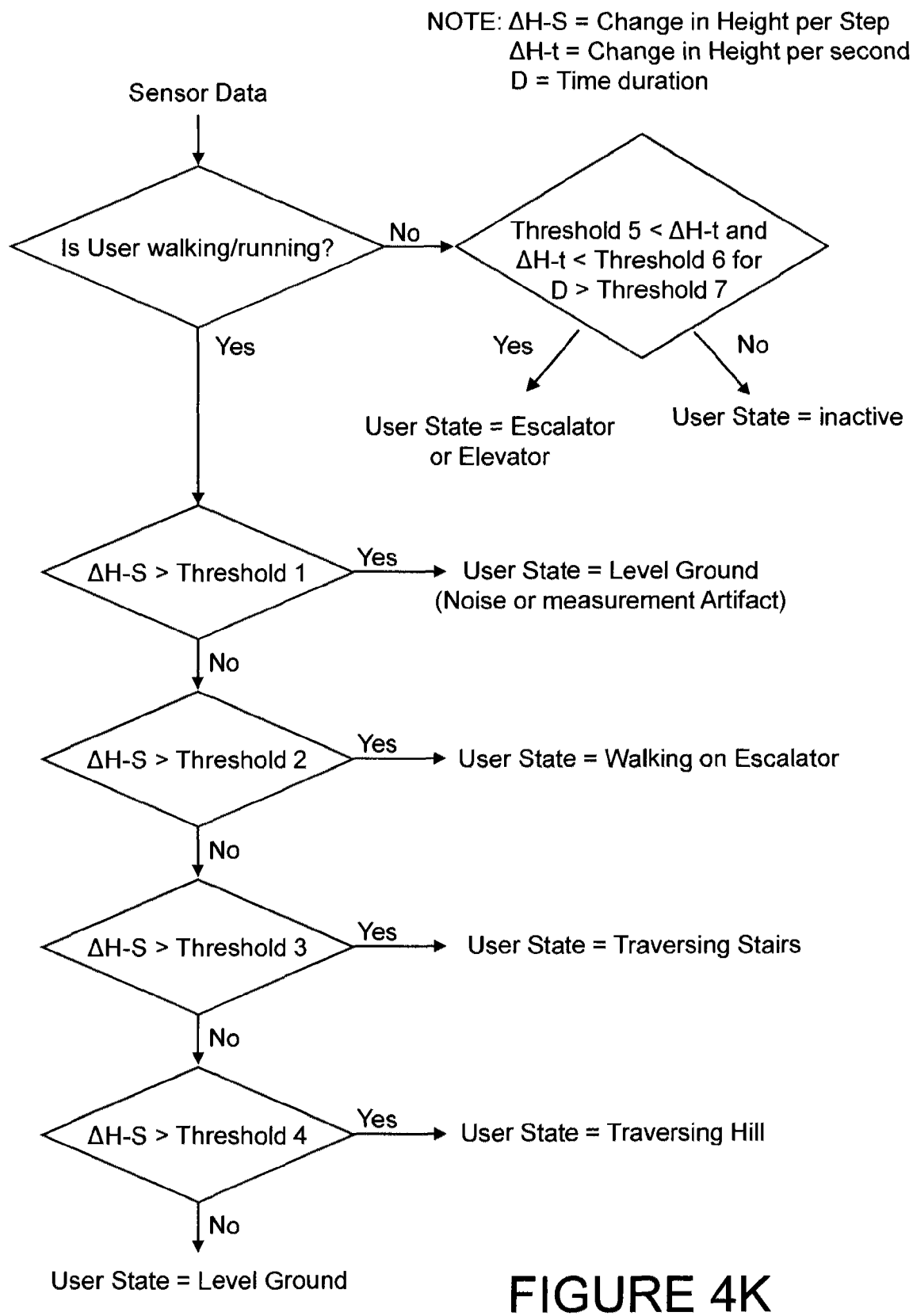
FIGS. 4K and 4L are flowcharts exemplary of processes for calculating, obtaining, assessing and/or determining the activity state of the user (for example, walking or running on relative flat or level ground, traversing stairs, on an escalator or in an elevator, traversing a hill or the like), based on certain sensor data including the attitude sensor data and/or physiological sensor data, according to certain aspects of the invention; notably, hereinafter the activity state of the user may be indicated as the "user state"
Figure 6:
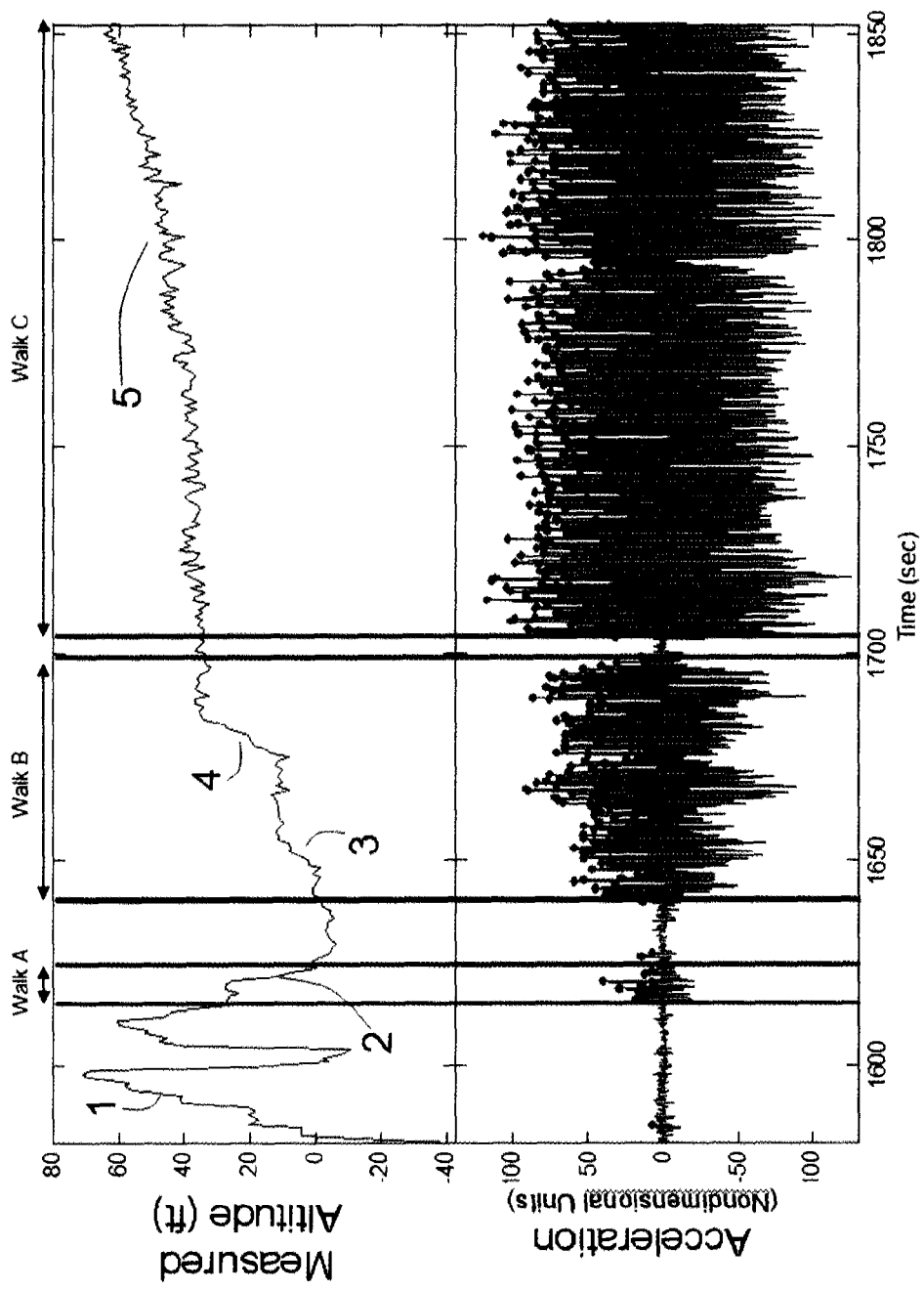
FIG. 6 is an example of determining the activity state of the user by evaluating the altitude sensor data based on or using algorithms or processes generally illustrated in the flowchart of FIG. 4K wherein altitude data is depicted in the top panel and acceleration data is depicted in the bottom panel; in this exemplary data set and activity state determination, the walking segments are marked A, B, C and are determined by the pedometer function with each step marked as a red dot in the bottom panel; drawing indicator 1 identifies a period of altimeter measurement artifact that is disregarded because the user has not performed any steps; drawing indicator 2 identifies a period of walking that includes a 20 ft drop in apparent altitude due to motion artifact—this is disregarded because the user only walked four steps during this interval, so $\Delta h/\Delta step=-5$ ft/step, which is likely not humanly possible under normal circumstances; drawing indicator 3 identifies a period of walking on stairs: 20 steps for a total height increase of 10 ft ($\Delta h/\Delta step=0.5$ ft/step) and is used to update the appropriate activity metrics; drawing indicator 4 identifies a period of walking up an escalator: 24 steps over 32 ft ($\Delta h/\Delta step=1.3$ ft/step) and is used to update the appropriate activity metrics, taking into account that the activity was partially assisted; drawing indicator 5 identifies a period of walking up a hill: 350 steps for a height increase of 33 ft ($\Delta h/\Delta step=0.1$ ft/step) and is used to update the appropriate activity metrics.

In one embodiment, the processing circuitry may evaluate the output of the altitude sensor to determine, calculate and/or estimate the activity state of the user by evaluating the altitude sensor data based on algorithms or processes based on the flowchart of FIG. 4K. With reference to FIG. 4K, in one embodiment, the processing circuitry determines the type of activity by evaluating the change in altitude of the user on a change in height or altitude per step basis ("$\Delta H$–S") or the use of an elevator by a sustained rate of height change pre time period (for example, per second) ("$\Delta H$–t") in the absence of steps. The change in height or altitude per step and change in height or altitude per second are evaluated against a plurality of thresholds and/or ranges to determine whether the user is, for example, moving (for example, running or walking) on level ground, on an escalator or in an elevator, traversing stairs and/or traversing a hill or the like. In one embodiment, Threshold1, Threshold 2, Threshold 3 and Threshold 4 have the relationship Threshold 1>Threshold 2>Threshold 3>Threshold 4 wherein the process seeks to detect and identify the causes of increases in user altitude. In other embodiments, the flow may be modified to detect and classify decreases or both increases and decreases in user altitude. Thus, in these embodiments, the processing circuitry employs data from the motion sensor to assess the user state based on data from the altitude sensor. An exemplary implementation is illustrated in FIG. 6.

Notably, for the avoidance of doubt, the inventions are not limited to processes and/or algorithms implemented in accordance with the flow charts of FIGS. 4A-4R. Such flow charts are merely exemplary. The present inventions may also implement batch processing algorithms (as opposed to the real-time algorithm), the use of probabilistic classification and estimation methods such as, for example, bayesian networks, Kalman filters, particle filters, unscented Kalman filters (aka sigma point Kalman filters), EM algorithm and Metropolis-Hastings algorithm, Gibbs sampling, Wiener filter, alpha-beta filter, or artificial neural networks. All permutations and combinations of the physiological conditions are intended to fall within the scope of the present inventions.

Figure 1B:
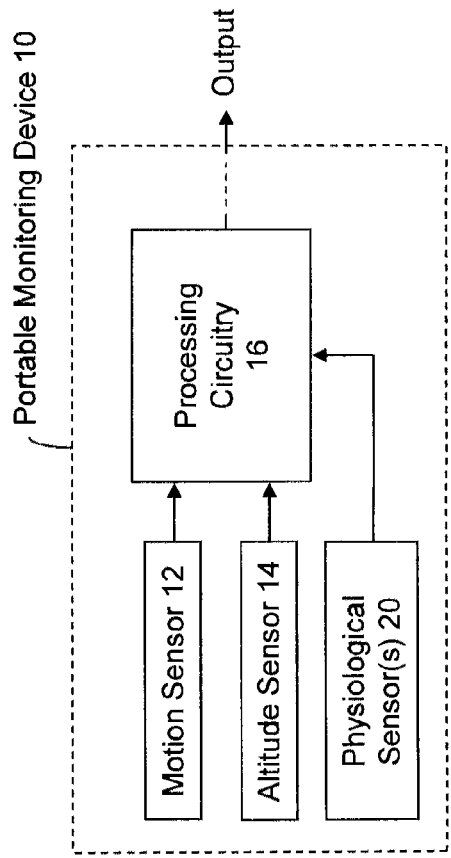
Figure 7:
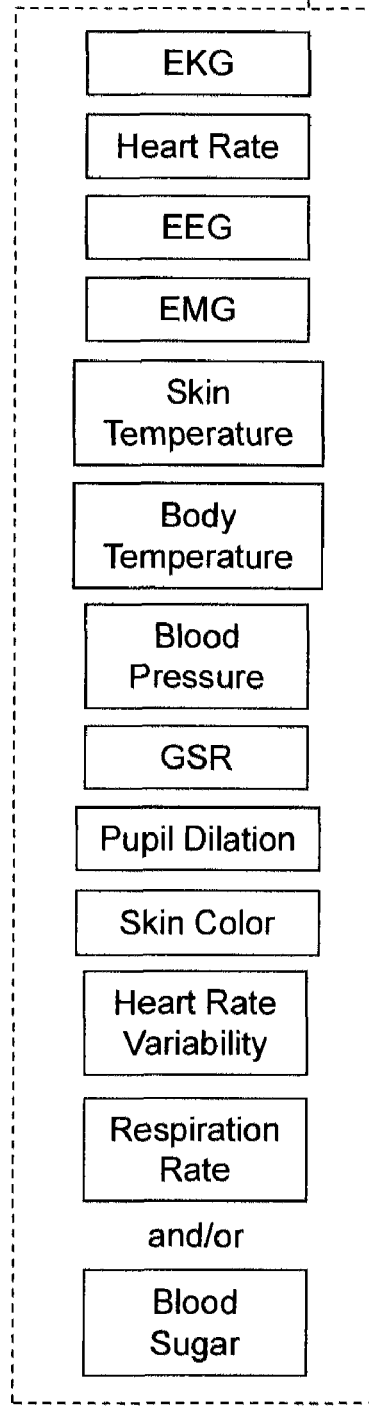
FIG. 7 is a block diagram representation of one or more physiological sensor(s) to determine, sense, detect, assess and/or obtain information which is representative of physiological information of the user, according to at least certain embodiments of the present inventions; notably, the one or more physiological sensor(s) may be incorporated in and/or coupled to the exemplary portable monitoring devices (for example, physically, electrically and/or optically coupled, including wired and/or wirelessly coupled) according to at least certain embodiments of the present inventions.

In another embodiment, the portable monitoring device of the present inventions includes one or more physiological sensors to further assess the activity state of the user. For example, with reference to FIGS. 1B and 7, the physiological sensor(s) may provide data which is representative of the physiological condition of the user. The processing circuitry may correlate the data from the physiological sensor(s) with the (i) data which is representative of the altitude and/or changes in altitude and (ii) data which is representative of the motion of the user, to determine, estimate and/or calculate energy and/or calorie "burn" of the user. For example, an apparent increase in altitude coupled with the expected number of human steps and a correspondingly increase in heart rate enables the processing circuitry (and techniques implemented thereby) to assess such data and more accurately correlate the activity to a user state—for example, distinguish stair steps from a measurement artifact.

Figure 4L:
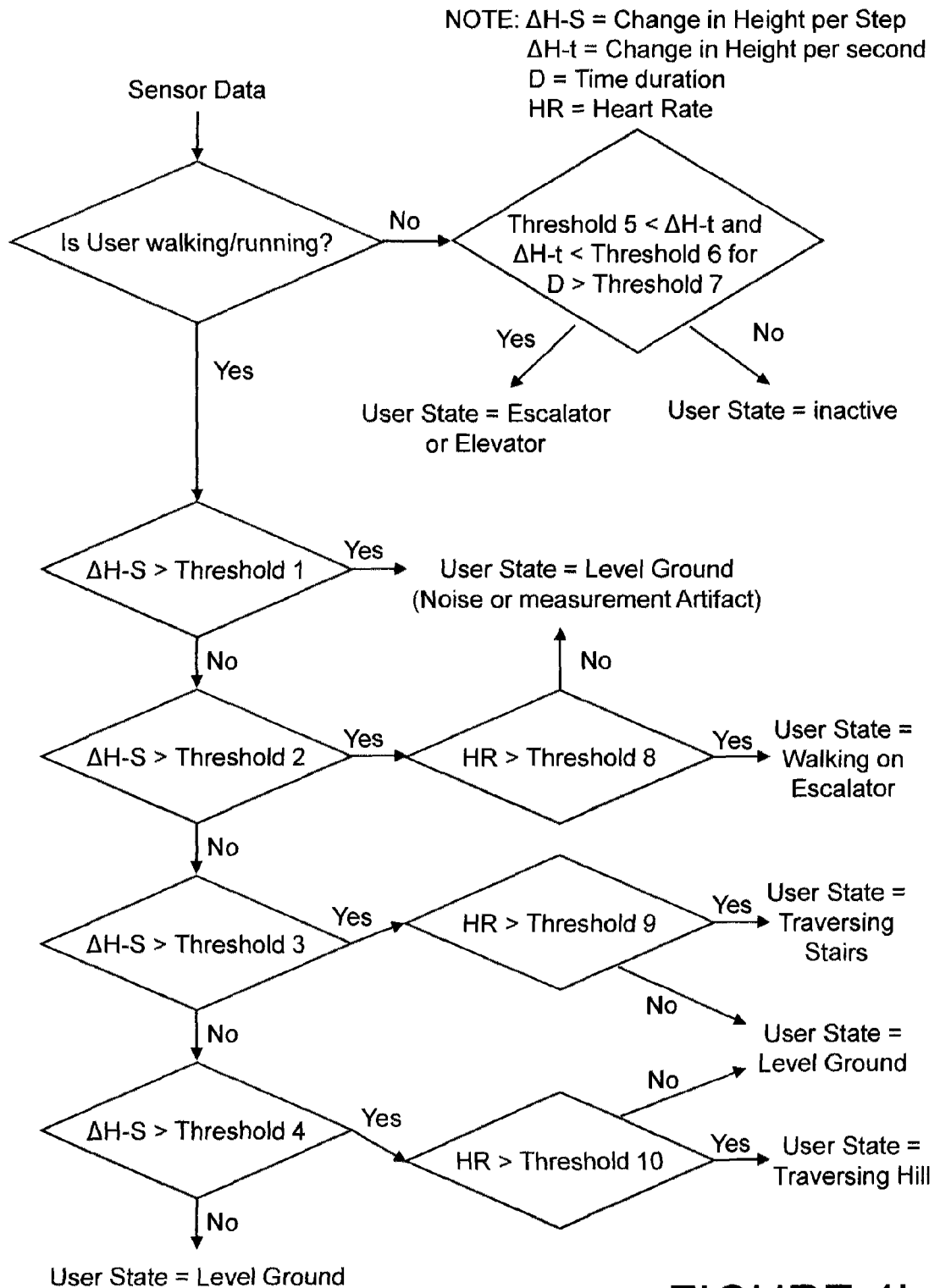
Figure 4M:
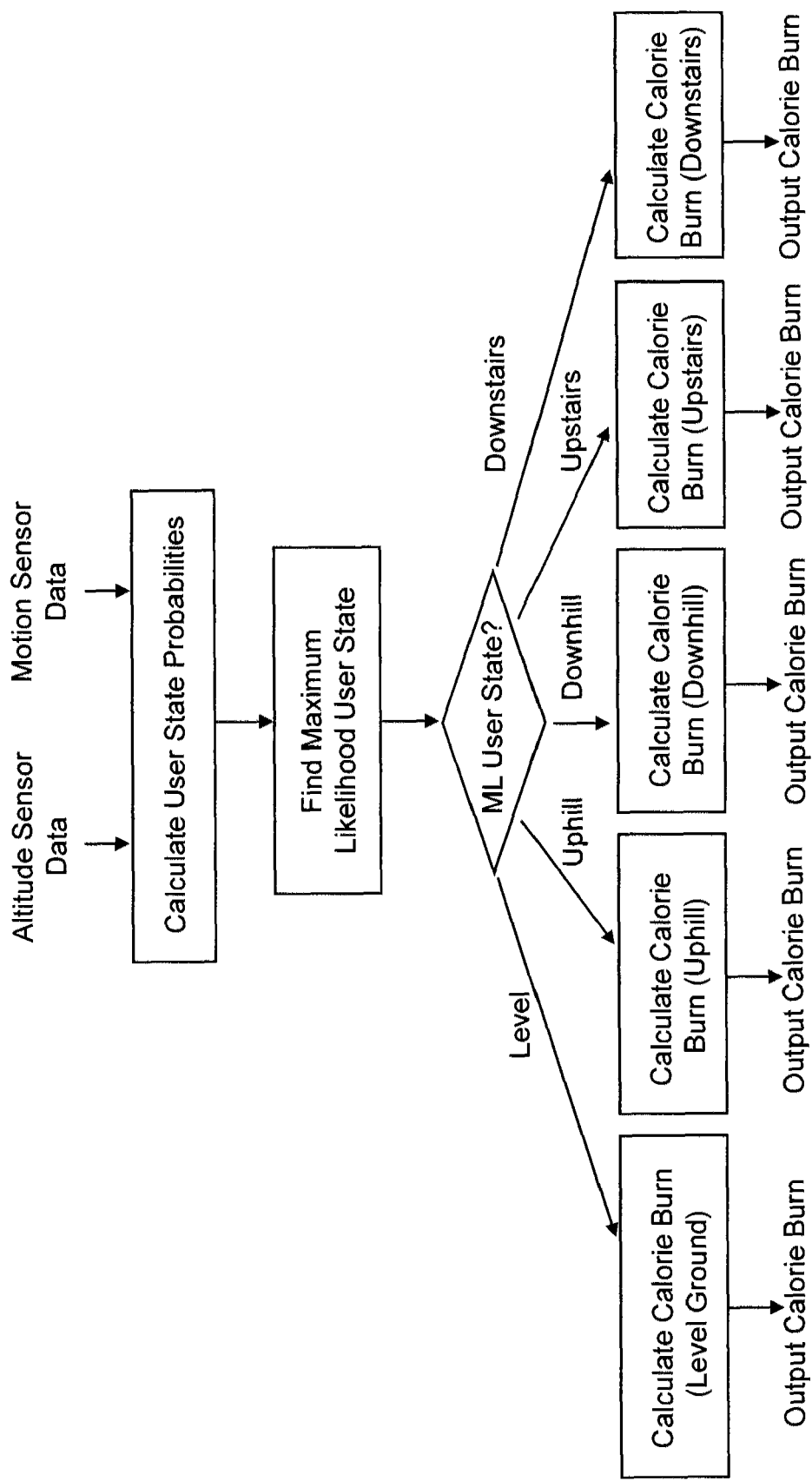
Figure 4N:
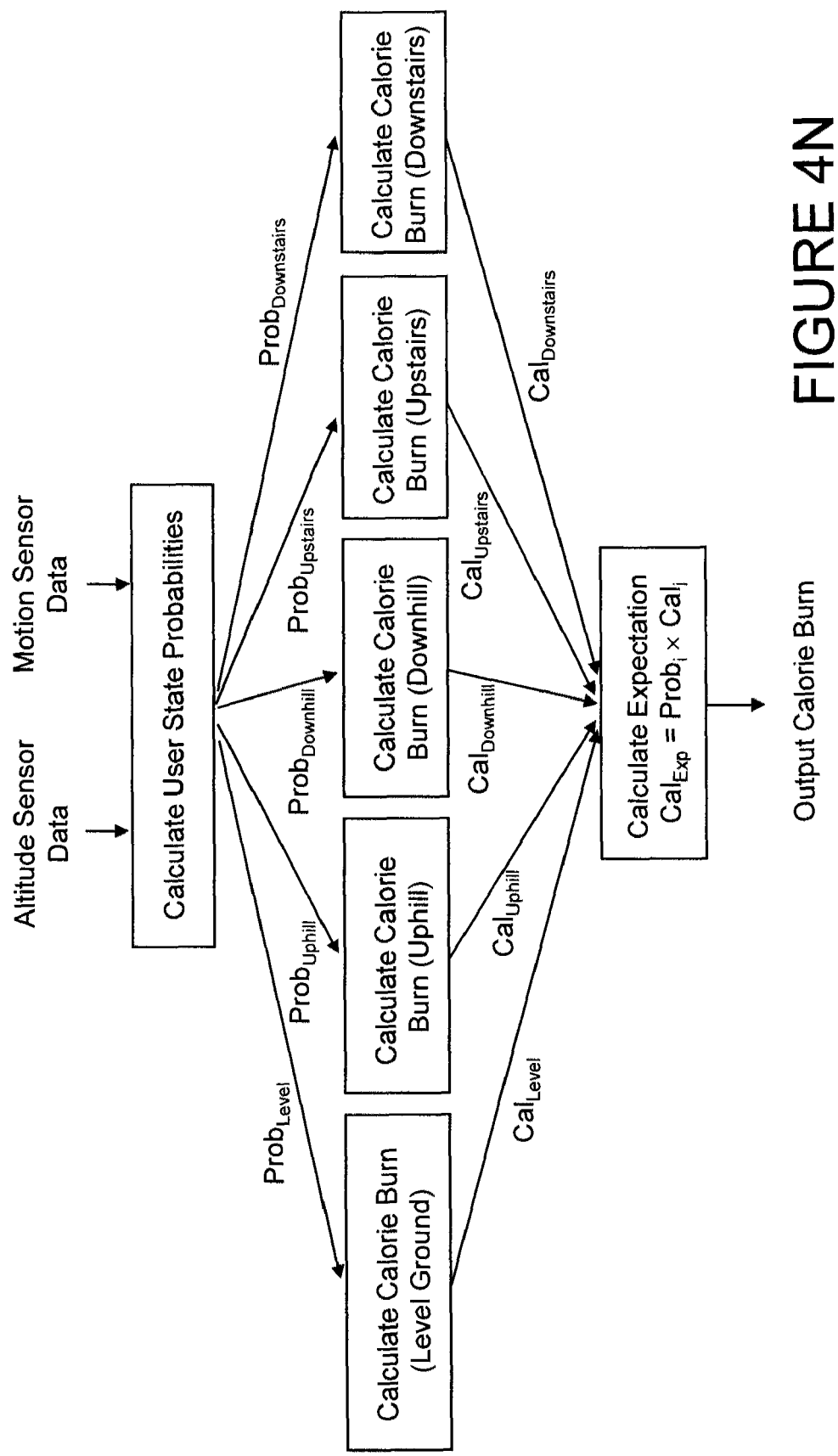
Figure 40:
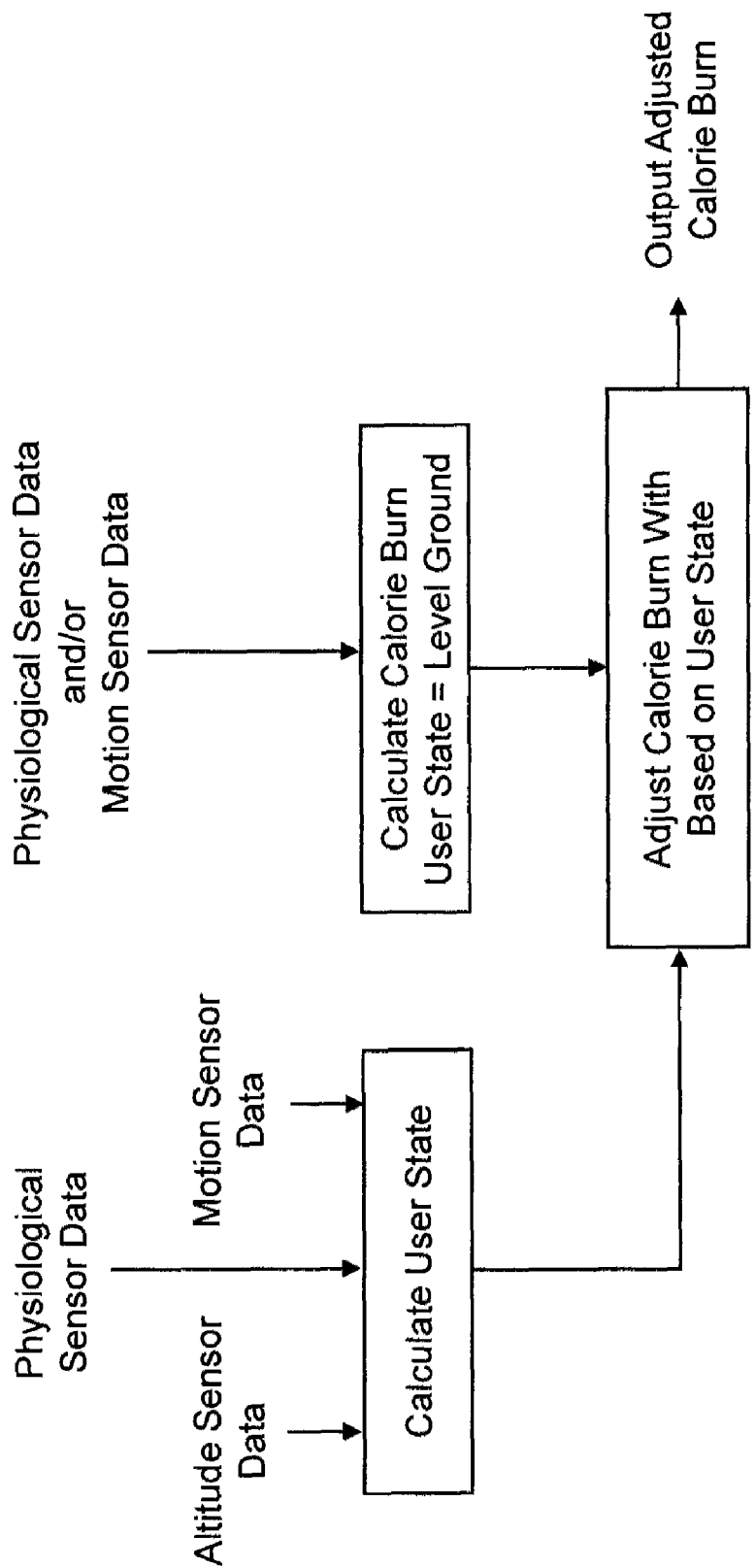
Figure 4P:
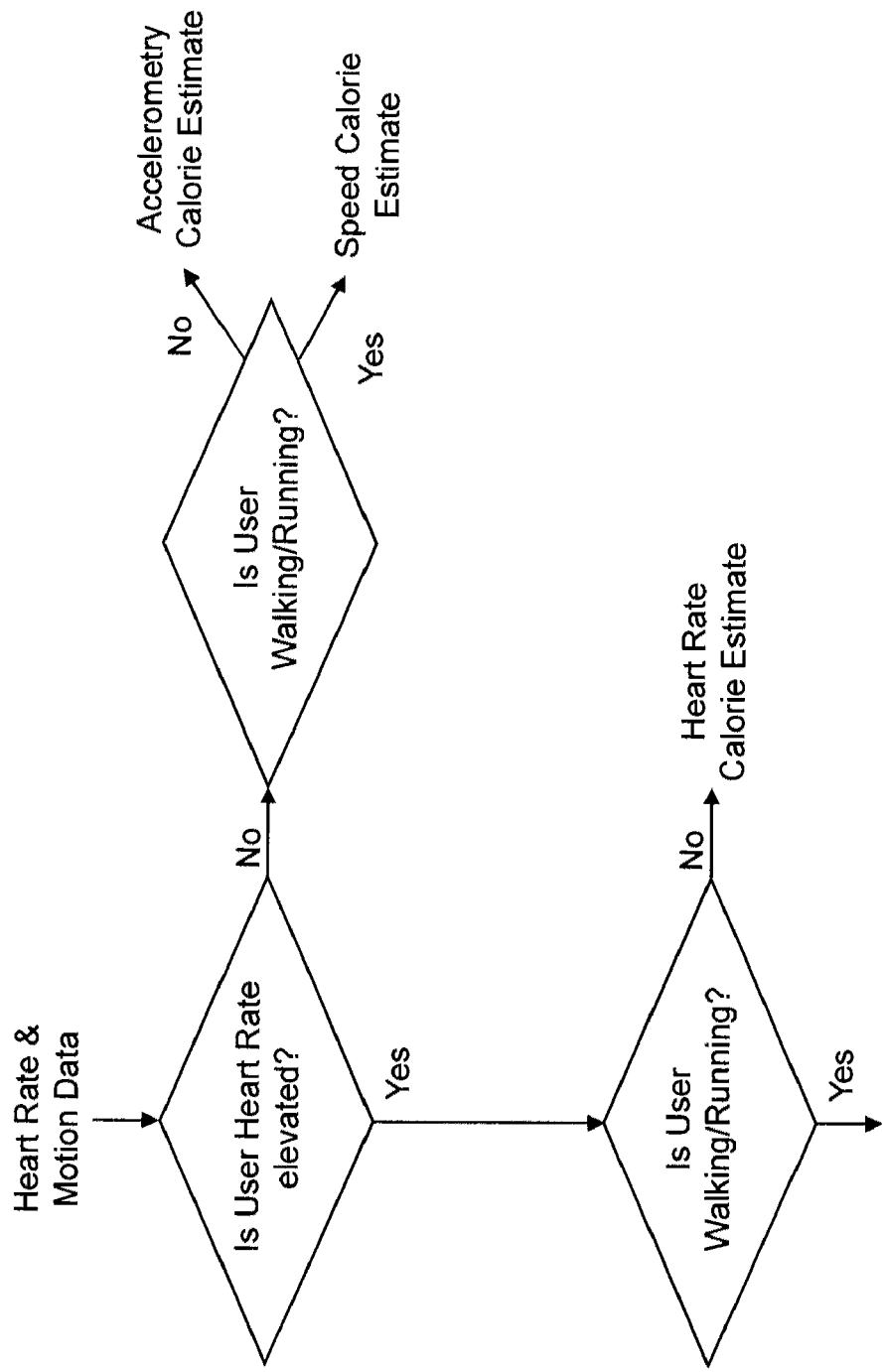
Figure 4Q:
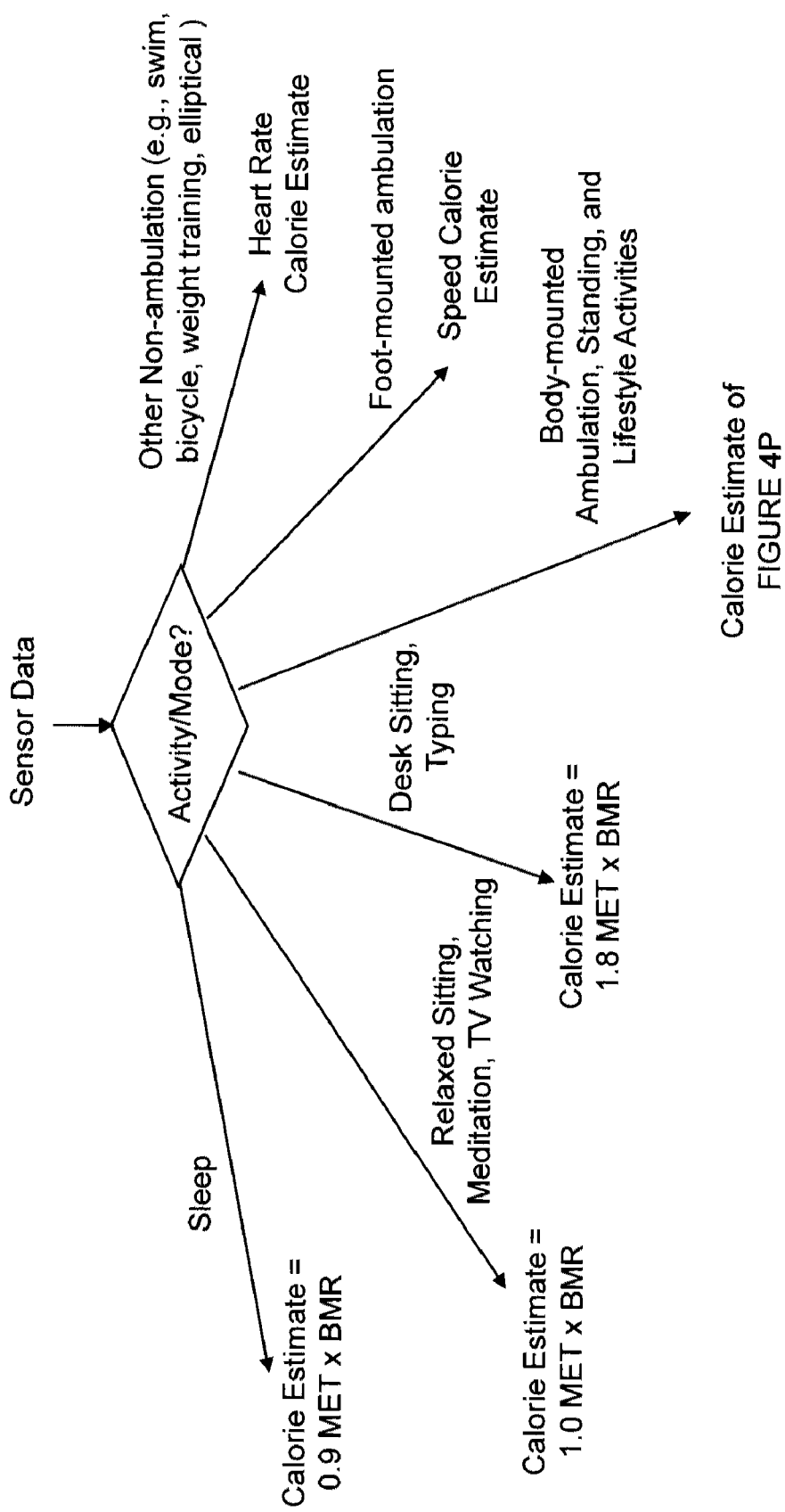
Figure 4R:
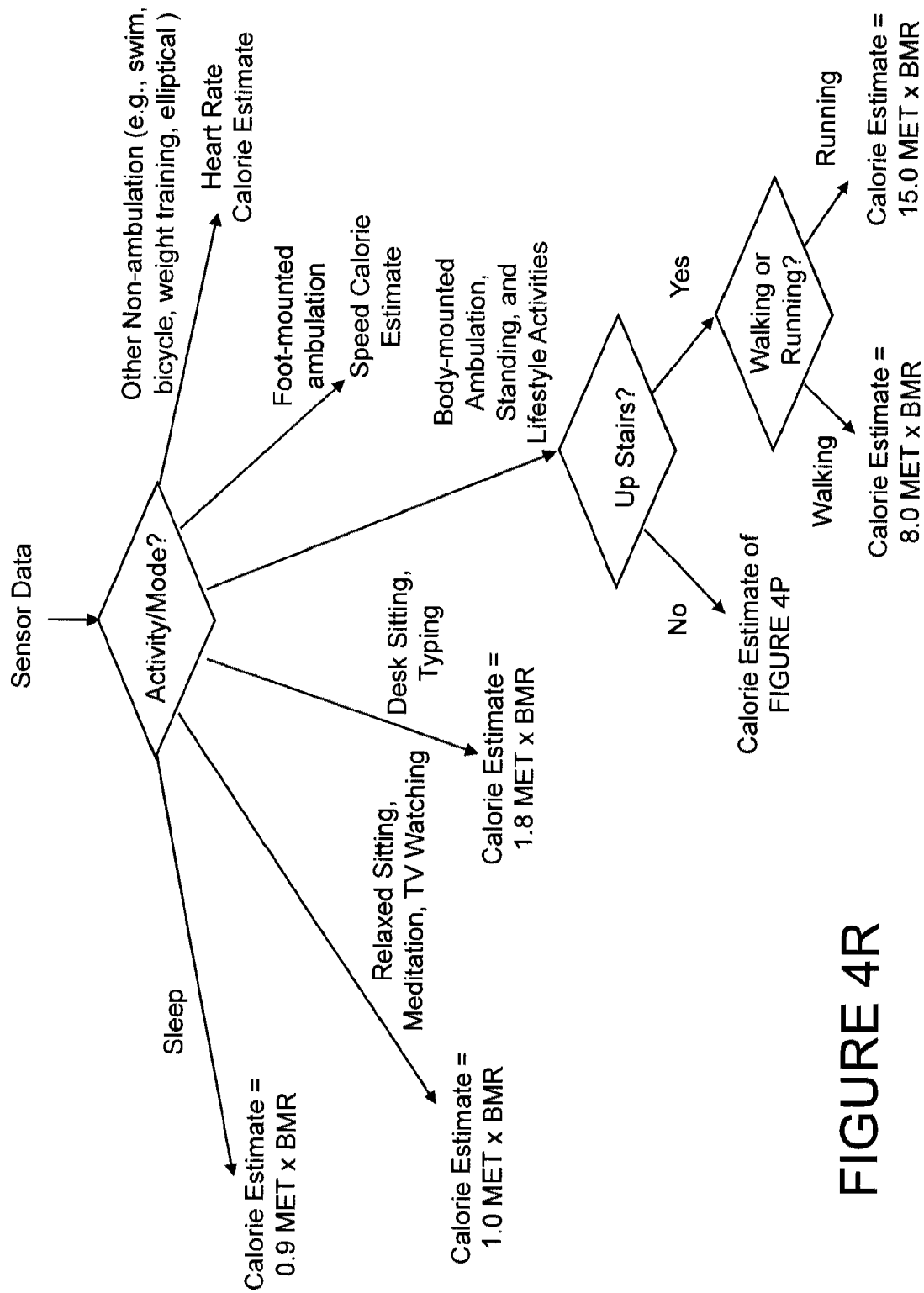

In one embodiment, the processing circuitry may employ a decision-tree based technique/algorithm to interpret or assess changes in altitude, motion and physiological condition of the user. The decision tree based technique/algorithm may employ the flow chart of FIG. 4L in which, as another embodiment, the processing circuitry determines the type of activity by evaluating the change in altitude of the user on a change in height per step basis ("ΔH–S") or the use of an elevator by a sustained rate of height change per temporal period (for example, seconds) ("ΔH–t") in the absence of steps in conjunction with heart rate ("HR"). The change in height per step, change in height per second, and heart rate are evaluated against a plurality of thresholds and/or ranges to determine whether the user is, for example, moving (for example, running or walking) on level ground, on an escalator or in an elevator, traversing stairs and/or traversing a hill or the like. In one embodiment, Threshold1, Threshold 2, Threshold 3 and Threshold 4 have the relationship Threshold 1>Threshold 2>Threshold 3>Threshold 4. Thus, in this embodiment, the processing circuitry employs data from the motion sensor to assess the user state based on data from the altitude sensor and physiological sensor. Similar techniques/algorithms may employ the flow of FIG. 4L and a similar flowchart based on thresholds in relation to other certain physiological conditions including blood pressure, pulse rate, blood sugar and the waveform shape corresponding to the heart beat.

In one embodiment, rather than making a firm "decision" based on thresholds, the processing circuitry may employ the sensor data individually or in combination in a statistical or ad hoc framework to provide probabilities for each potential user state. Such techniques may provide a higher degree of confidence in connection with determining the user state.

The processing circuitry may employ filtering methods and state estimation to mitigate, address and/or alleviate noise (for example, random noise) and outliers present or inherent in the altimeter data. For example, in a preferred embodiment, several parameters of interest may be described in state-space notation:

$$x(t)=[H(t)dH(t)]^T,$$

where x is the state vector, H is altitude or height, and dH is the first derivative of H with respect to time.

In this notation, dH(t) is similar or equivalent to the parameter ΔH–t described previously. Note that these parameters are expressed as functions of time.

In another preferred embodiment, several parameters of interest may be described in an alternate state space:

$$x(\text{step})=[H(\text{step})dH(\text{step})]^T,$$

where x is the state vector, H is the altitude, and dH is the first derivative of H now expressed as functions of step, where the implicit relationship on time for step is omitted for notational simplicity.

Notably, dH(step) is similar or equivalent to the parameter ΔH–S described previously. The time-space and step-space representations may be employed together or separately in one or more estimation techniques. Indeed, when used separately, many methods may be used to estimate the derivative that is not covered in the representation. For example, when only the time-space representation is used, the parameter dH(step) may be estimated as:

$$dH_{EST}(\text{step})=(H_{EST}(t)-H_{EST}(t-dT))/(\text{step}(t)-\text{step}(t-dT)),$$

where dT is a time interval, step(t) is the step count at time t, and the EST subscript denotes an estimate.

Similarly, when the step-space representation is used, the parameter dH(t) may be estimated as:

$$dH_{EST}(t)=(H_{EST}(\text{step}(t))-H_{EST}(\text{step}(t)-\text{step}(-dT)))/(t-dT),$$

where dT is a time interval.

Given the state vector x, many models may be employed to regularize the estimates of x in a model-based observer such as a Luenberger observer, Kalman filter, least squares estimator, recursive least squares estimator, intermediate multiple model filter (IMM), extended Kalman filter, particle filter, unscented Kalman filter (aka sigma point filter), etc. In a time-space representation, the altitude of the user may be described by a constant velocity model:

$$x(t+dT)=Fx(t)+w,$$

$$F = \begin{bmatrix} 1 & dT \\ 0 & 1 \end{bmatrix},$$

where dT is a time interval and w is process noise.

In a step-space representation, the altitude of the user may be described by a constant velocity model:

$$x(\text{step}+d\text{Step})=Fx(\text{step})+w,$$

$$F = \begin{bmatrix} 1 & d\text{Step} \\ 0 & 1 \end{bmatrix},$$

where dStep=x(step(t+dT))–x(step(t)) and w is process noise.

Note that in both models, a constant altitude may be obtained by fixing dH=0. One or more constant altitude models and constant velocity models may be desirable in a multiple model filter. In certain cases, it may be useful to use a multiple model filter such as an IMM or multiple hypothesis filter in order to obtain fast estimate convergence during transitions that are not constant velocity. Process noise in a constant velocity model may be tuned through historical analysis of pressure measurements while the user is not moving.

The model-based approach permits the prediction of future altitude measurements as:

$$x_{PRED}(t+dT)=CFx_{EST}(t),$$

$$x_{PRED}(\text{step}+d\text{Step})=CFx_{EST}(\text{step}),$$

$$C=[1\ 0],$$

for both models.

Defining z=H+v to be a noise corrupted measurement of altitude, a residual may be calculated as:

resid=z−$x_{PRED}$ which allows the statistical rejection of outliers against known measurement and process noise statistics through, for instance, hypothesis testing. Other outlier rejection and step offset compensation methods may be employed including those apparent to those skilled in the art.

By setting C=[1 0], we have implicitly assumed that the measurements obtained are altitude measurements. However, the present inventions are not limited to such, nor are they limited to the set of linear models as described thus far. For instance, a raw measurement may be barometric pressure and it may relate to altitude by the function H=C(pressure), where C(•) is a standard, nonlinear barometric equation. In such cases, the system may be linearized to work within the framework of a linear estimator (e.g., extended Kalman filter) or a nonlinear estimator may be used (e.g., particle filter).

The processing circuitry may employ other estimation and filtering methods. For instance, in one embodiment, H may be estimated with a median, moving average, exponentially weight moving average, low pass filter, etc. dH(step) and dH(t) may likewise be estimated in a variety of ways involving finite differencing with or without smoothing, etc. All such techniques are intended to fall within the scope of the present inventions.

Figure 8B:
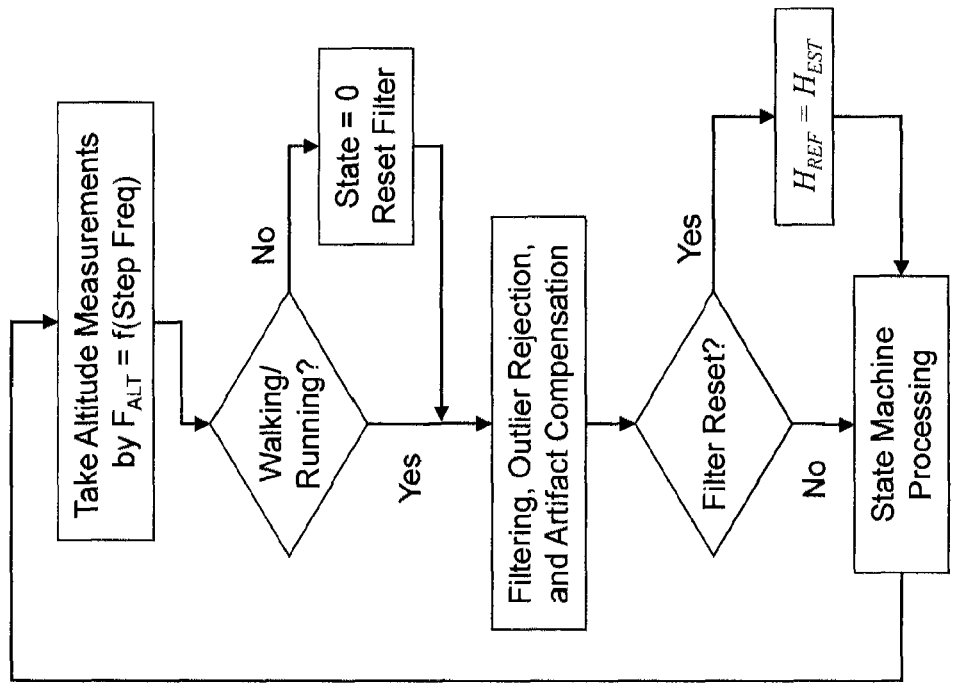
FIGS. 8A-8G are flowcharts of exemplary processes or logic employed by the processing circuitry (for example, a state machine) to determine, estimate and/or calculate changes in altitude), according to certain aspects of the present inventions.
Figure 8A:
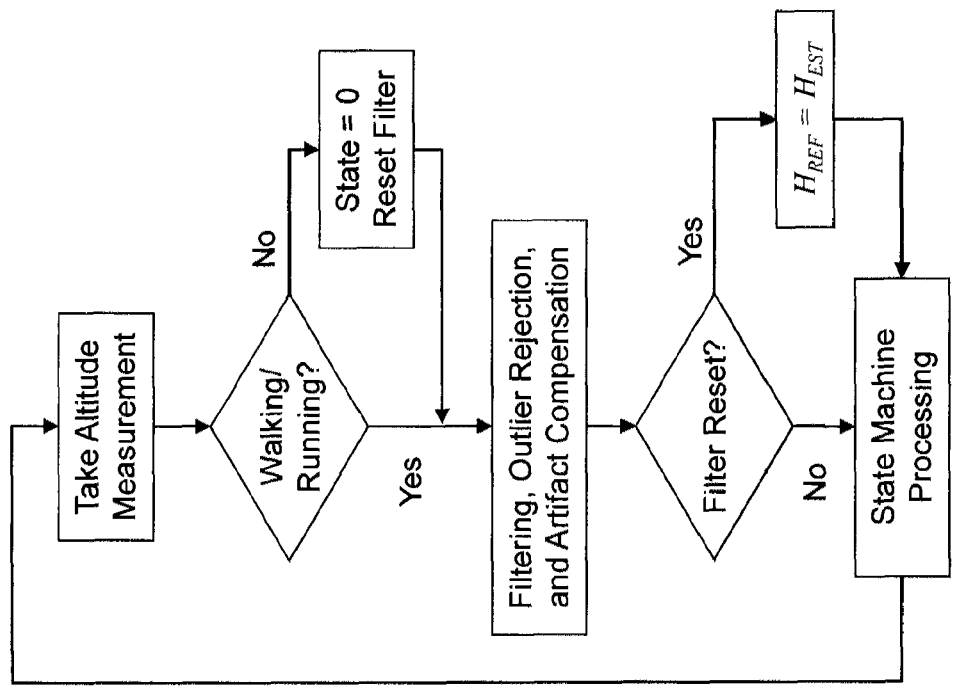
Figure 8C:
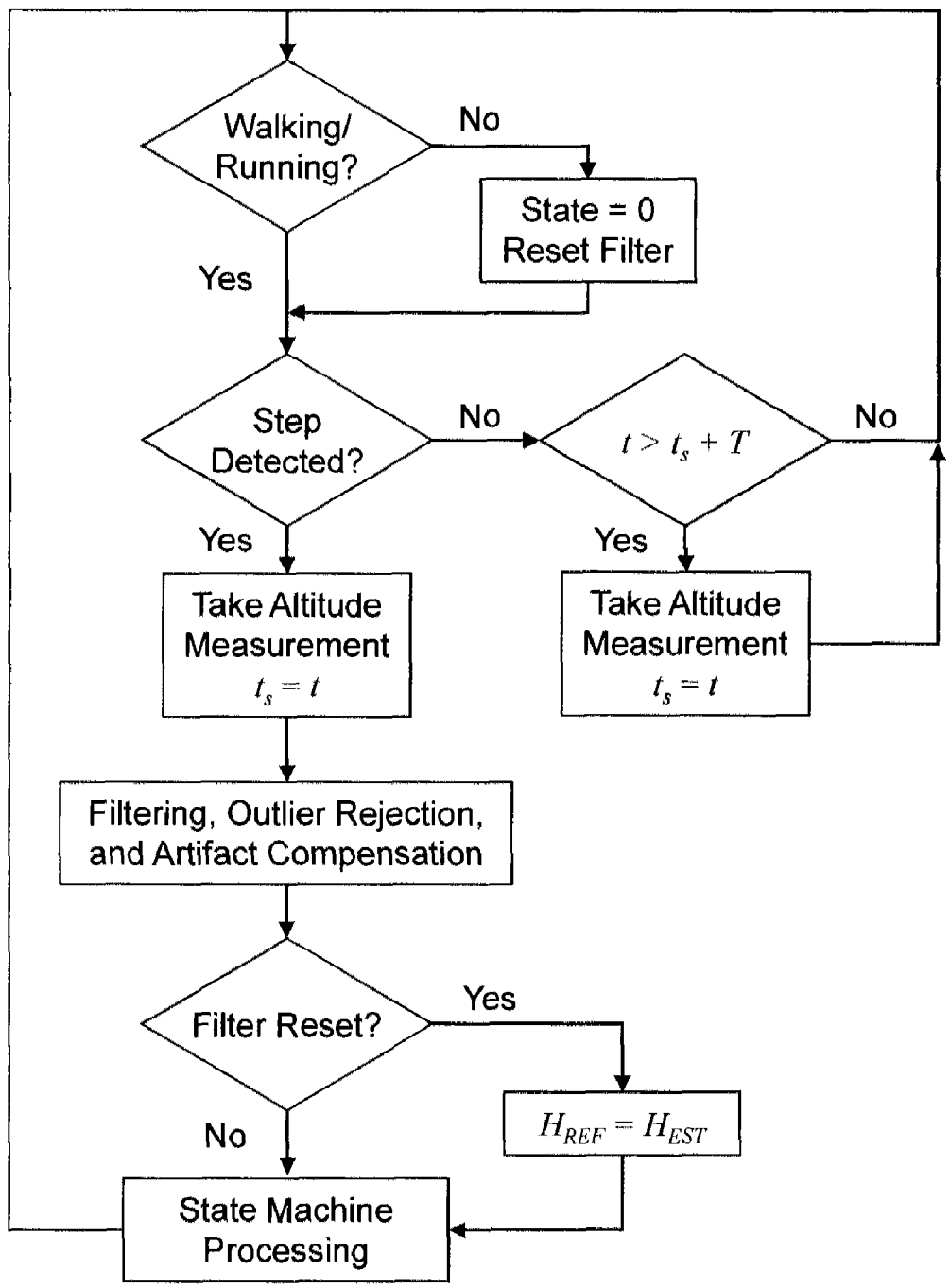
Figure 8E:
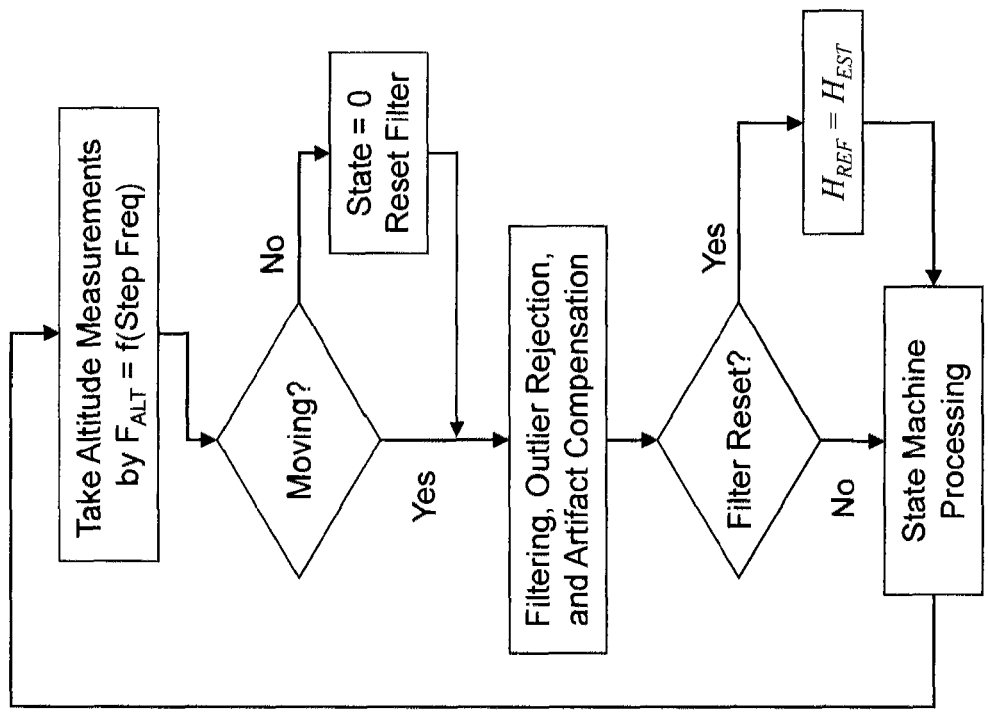
Figure 8D:
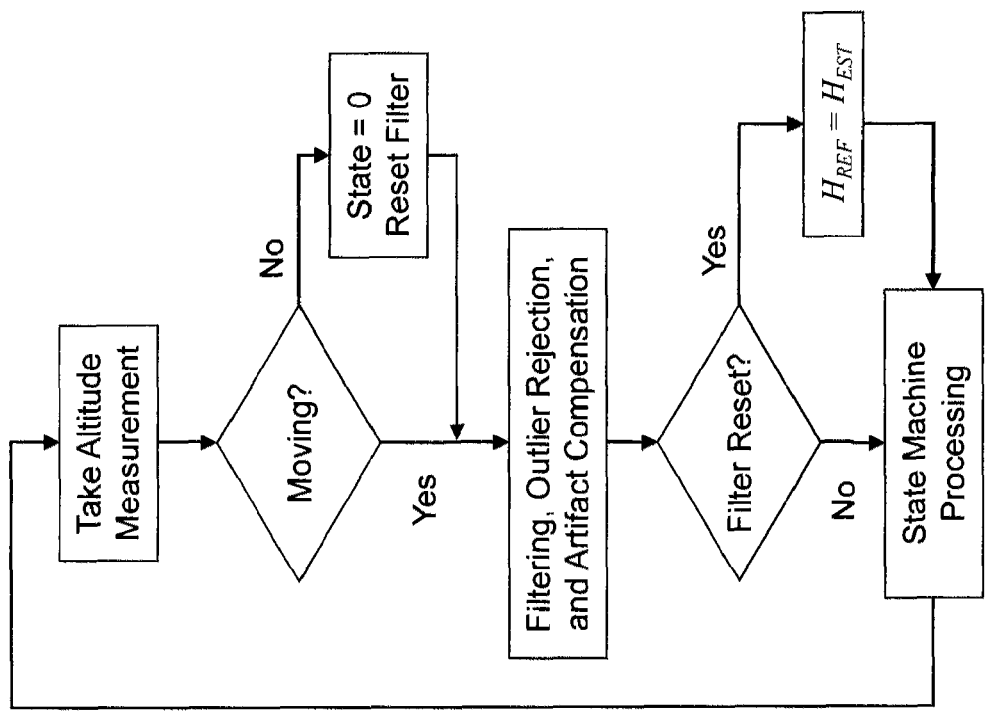
Figure 8F:
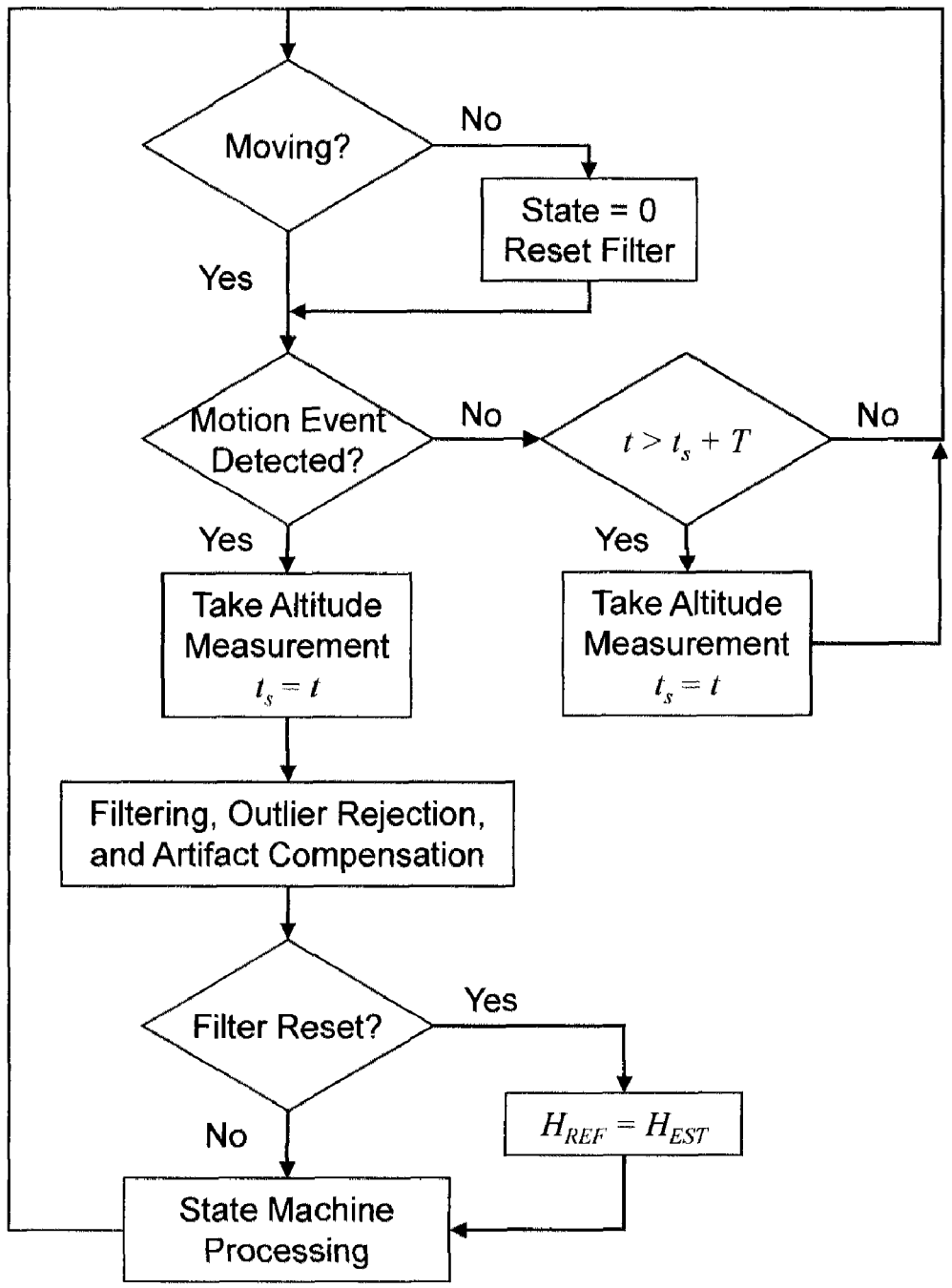

The processing circuitry may employ state machine logic to determine, estimate and/or calculate a change in altitude. FIGS. 8A-8F illustrates several embodiments of exemplary state machine logic for calculating human-derived altitude. In some embodiments for calculating human-derived altitude (FIGS. 8A-8C), data of the motion sensor is used to determine if the user is currently walking/running as well as if the user recently executed a step. This may be achieved, for instance, with a pedometer. For example, FIG. 8A depicts an embodiment where, although data of the motion sensor is used to determine if the user is currently walking/running, the sampling of the altitude sensor (to acquire data which is representative of the altitude and/or change in altitude of the user) is performed independent of the data from the motion sensor. In contrast, FIG. 8B depicts an alternate embodiment where the sampling rate of the altitude sensor is calculated as a function of the data from the motion sensor. In this case, the sampling frequency $F_{ALT}$ is a function of the user's step frequency. FIG. 8C depicts an embodiment where sampling of the altitude sensor is triggered from events detected by the motion sensor. In this exemplary embodiment, the event is detection of a step by the user. Although not depicted in FIG. 8C, altitude measurements may be obtained following some delay after the detection of the triggering event. This may be useful in systems where a change in measured altitude occur after some latency, as in cases where a barometric pressure sensor is mounted in a sealed enclosure and samples the external atmospheric pressure through a vent. Altitude sensor measurements may also be triggered by events related to the stop of motion as in, for instance, when the user stops walking for several seconds.

Notably, in other embodiments, characteristics of the motion sensor are used to determine if the user is currently moving as well as if the user recently executed a motion event. (See, for example, FIGS. 8D-8F). Thus, in these embodiments for calculating human-derived altitude (FIGS. 8A-8C), data of the motion sensor is used to determine if the user is currently walking/running as well as where the user recently (for example, within a previous predetermined amount of time) executed a motion event.

Figure 8G:
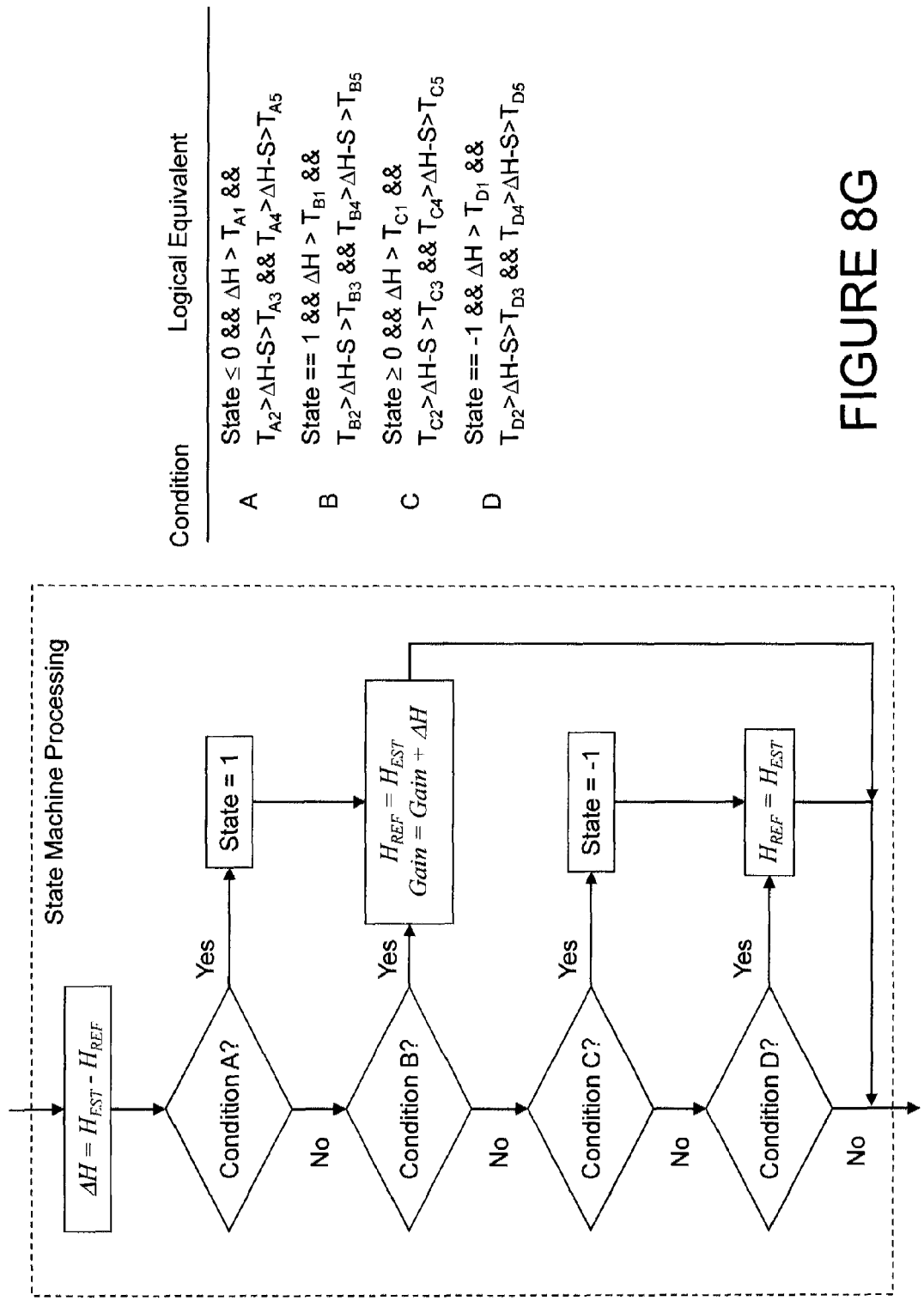

FIG. 8G provides exemplary state machine logic that may be used to accumulate human-derived elevation gain. In this exemplary embodiment, the state machine logic employs a plurality of thresholds to indicate the start, stop, and continuation of sustained elevation changes. These thresholds are denoted by $T_{ij}$, i∈{A, B, C, D}, j∈{1, 2, 3, 4}; however, these are intended as examples and in other embodiments of the inventions, there may be differing numbers and combinations of thresholds. Elevation gain is accumulated when the current estimate of elevation $H_{EST}$ exceeds a reference $H_{REF}$ by at least the amount given by the threshold, as well as when ΔH−S and ΔH−t are within certain thresholds. Appropriate settings of the thresholds may provide "hysteresis" in the accumulation of elevation gain and likewise restrict impossible or improbable conditions. For instance, setting $T_{A2}$=1 ft/step and $T_{A3}$=0 ft/step restrict user elevation gains to fall within those prescribed by typical staircases. A typical stair step is 6 inches and a user walking up two stairs a time may cover 1 ft per step.

Figure 8H:
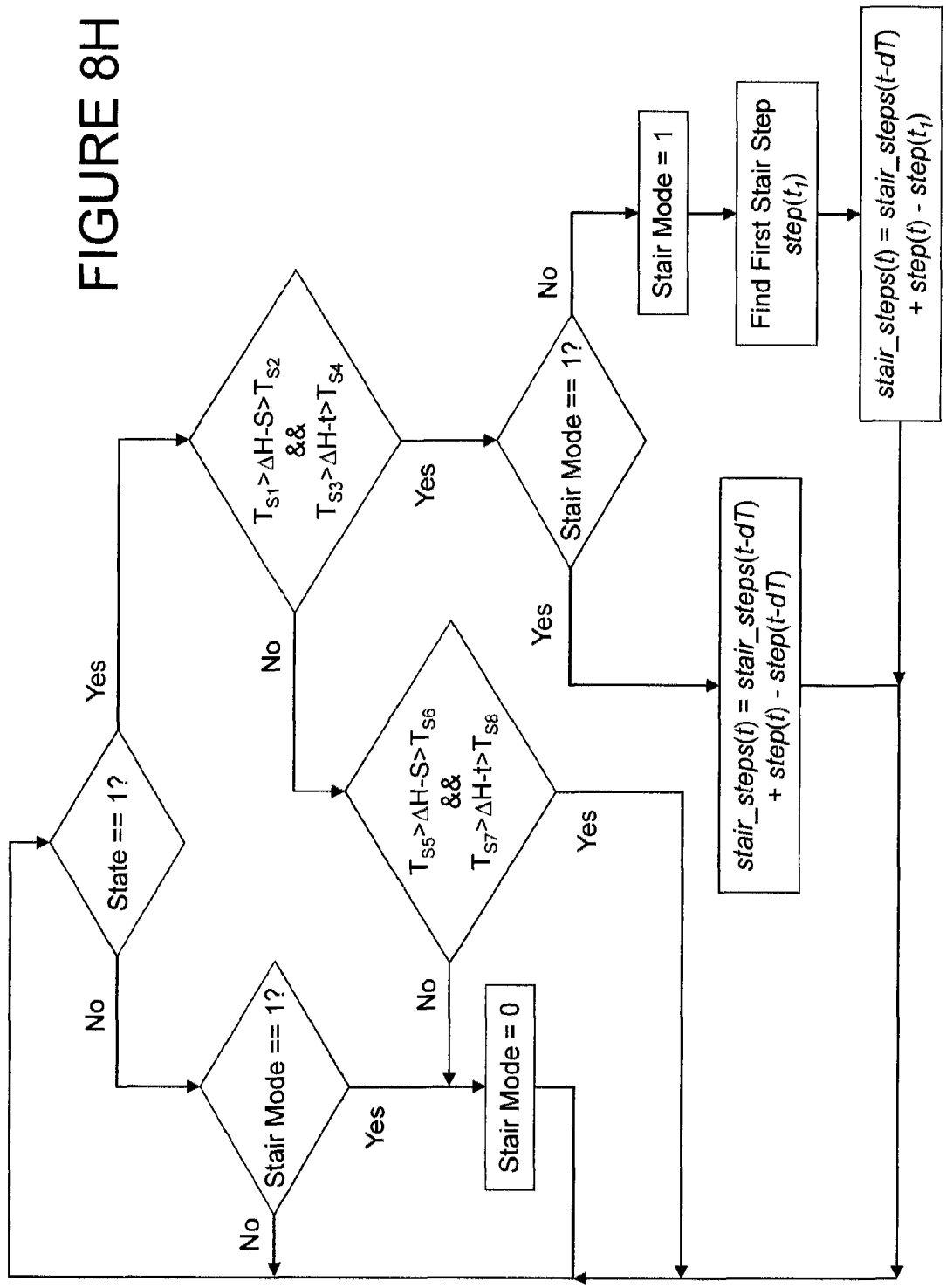
FIG. 8H is a flowchart of an exemplary process or logic to compute, estimate and/or determine a number of stair steps traversed by the user (for example, the number of upward stair steps), according to certain aspects of the present inventions; notably, in this exemplary embodiment, when ΔH–S and ΔH–t meet a first criteria, the processing circuitry determines, calculates and/or estimates an onset of the first step of the stair sequence.

As mentioned above, in one embodiment, the processing circuitry computes, estimates and/or determines a number of stair steps traversed by the user (for example, the number of upward stair steps). For example, with reference to FIG. 8H, in one exemplary embodiment, when ΔH−S and ΔH−t first meet a first criteria, the processing circuitry determines, calculates and/or estimates an onset of the first step of the stair sequence. An exemplary value for the threshold $T_{S2}$ is 5 inches, which is a low riser height for a staircase. Stair steps are accumulated thereafter until ΔH−S and ΔH−t do not meet a second criteria.

Notably, the processing circuitry may determine, calculate and/or estimate a first step in a stair sequence using any technique now known or later developed. For example, the processing circuitry may employ the following: One or both of the derivatives (ΔH−S and ΔH−t) may be back-propagated to their intersection with a relatively flat region of the measured and/or filtered altitude curve. Indeed, the first step may be identified as the changepoint between two intersecting lines in either the time or step-space representations (or both) and well-known estimation techniques may be employed.

The method described here may be adapted to calculate the number of downward stair steps, and/or the altitude gain/loss from upward/downward stair steps, and/or the calorie expenditure from the upward/downward traversal of stairs and/or the number of stair flights traversed upward/downward and/or the number of stair flight/step equivalents traversed upward/downward (e.g., by dividing the altitude gain/loss by a nominal stair flight/step height). All combinations and permutations are intended to fall within the scope of the present inventions. In one embodiment, the portable monitoring device may be used to determine, calculate and/or estimate the step rise and/or step tread on a staircase.

In lieu of or in combination with stair steps, altitude gain, etc., the portable monitoring device may also calculate metrics (for example, motivational metrics) and/or calculate the state of avatars (for example, a digital "pet", a graphical representation of the user or his/her alter ego, a game character, or physical object that glows and/or changes physical configuration) that are partially or completely determined by user altitude changes. For example, the device may calculate (and, in addition, may display to the user) "elevation points", where one elevation point is representative of a change in altitude, a stair, and/or a flight of stairs (for example, one elevation point is equal to approximately ten feet, or one flight of stairs). A user may then be motivated to increase an elevation point score or total by, for example, traversing more stairs, flights of stairs and/or hills. Moreover, the device may also maintain the state of a virtual avatar, for example, a flower, whose growth and/or health is related to user altitude changes, or a building, whose size and/or growth is related to user altitude changes, or an entity that morphs between states that are indicative of increased or decreased elevation gains such as a stair case, ladder, hill, or mountain, or specific landmarks like the Eiffel Tower, Mt. Everest, and the Moon. Indeed, all games and/or avatars that are controlled in part or wholly by changes in altitude sensor data are intended as embodiments of the present inventions.

In other aspects of the present inventions, the altitude changes may be combined, integrated and/or fused with other information such as user speed, step frequency, surface grade, stair steps, calorie burn, energy expenditure, heart rate, etc. to obtain more general "activity points", where, for example, activity points may be described as:

$$AP = k1*MET + k2*\Delta H + k3*(HR - HR_0),$$

where k1, k2, and k3 are parameters, MET are metabolic equivalent units expended, HR is the user's heart rate and $HR_0$ is a nominal at-rest heart rate.

This equation is provided merely for illustration. Indeed, all relationships that describe activity points and/or "grades" and/or activity metrics that are not inherently physical quantities (e.g., calorie burn) and/or avatar states as an integrated, combined and/or fused output from one or more of user motion data, user physiological data, user elevation data, and/or user location data are simply embodiments of the present inventions. Likewise, all relationships that describe elevation points, and/or "grades" and/or metrics that are not inherently physical quantities (e.g., elevation gain) and/or avatar states as an output from either altitude data alone or in combination with user motion data, user physiological data, and/or user location data are simply embodiments of the present inventions. In some embodiments, the motivational metrics and/or avatars may be computed and/or displayed on the portable monitoring device. In other embodiments, the motivational metrics and/or avatars may be computed and/or displayed on other media (e.g., www.fitbit.com) using data from the portable monitoring device. In yet other embodiments, the motivational metrics and/or avatars may be computed and/or displayed on both the portable monitoring device and other media.

Notably, in one embodiment, the processing circuitry may adjust certain thresholds (for example, thresholds employed in conjunction with the techniques described herein) dynamically according to a variety of parameters to mitigate noise and drift from appearing in the output accumulated elevation gain. For example, such parameters may be based on surface conditions, weather, temperature, humidity, user motion, and physiological data from the user. Examples include the surface grade, user speed, user step frequency, user energy expenditure rate, user activity state (e.g., walking versus running versus jumping), $\Delta H-S$, $\Delta H-t$, weather conditions (e.g., incoming storm, wind, rain), the rate of change in barometric pressure while the user is not moving, the rate of change of temperature change, variation in the barometric pressure signal and/or altitude measurement (e.g., random noise), motion sensor data energy, motion sensor data variation, and/or heart rate.

In an exemplary embodiment, the thresholds required to accumulate an elevation gain follow a decreasing function with respect to surface grade, such that shallower grades require larger altitude gains and steeper grades permit smaller altitude gains. Furthermore in this regard, different functions may be used for walking and running such that shallower grades have lower thresholds for running than they do in comparison to walking. This is motivated by the fact that humans selectively perceive surface grades according to how fast they move on the surface. That is, shallower grades are easier to detect when the user is running rather than walking. Similar effects may be achieved by setting the thresholds as a function of surface grade and user speed or surface grade and user step frequency. Indeed, all possible combinations of the previously mentioned parameters may be used. Note that certain surface grades may be rejected from accumulation by setting their respective thresholds to infinity. In one embodiment, elevation gains and/or losses are only permitted for grades in excess of ±2%. The thresholds may also be adapted according to the drift and/or noise present on the altitude sensor while the user is not moving. In this way, the algorithm may adjust for changing weather conditions as observed by a barometric pressure sensor.

Surface grade may be expressed as the elevation change over a horizontal distance:

$$g = \Delta H/d.$$

When d is not directly measured (as in the case of GPS tracking), it may be calculated as:

$$d = sqrt(d_s^2 + \Delta H^2),$$

where $d_s$ is the distance traveled overland by the user.

For typical walking and running surface grades, it is sufficient to approximate $d=d_s$. Other numerical approximations exist and are apparent to one skilled in the art. The overland distance may be measured by any of a variety of methods, some of which were described above. They include use of a pedometer function or foot-mounted distance tracking. In other embodiments, the inventions may have functionality that determines the elevation change and/or slope between two points through, for instance, the use of GPS with an altimeter.

Notably, FIGS. 8A-8H are illustrative and are not intended to limit the implementation of the present inventions. For the avoidance of doubt, the thresholds depicted in the figures may be implemented on the measurements and/or estimates of altitude. The threshold logic may also be implemented over a sequence of points or over a time interval or both. In certain circumstances, it may not be useful or desirable to include all of the threshold parameters described. For instance, it may not always be useful to include thresholds against $\Delta H-S$ or $\Delta H-t$. The thresholds may also be supplanted with probabilistic functions evaluated jointly or conditionally over ($\Delta H$, $\Delta H-S$, $\Delta H-t$) or individually over some or all of the same parameters. The portable monitoring device may also employ a variety of timers and event counters to block certain calculation steps when, for instance, significant jumps in elevation are seen, noise increases, or outliers are encountered. Timers and/or counters may also be employed to reset the state of the algorithm (for example, state=0) and/or filter when a downward or upward accumulation event has not occurred within a certain time interval or number of iterations. The reference altitude $H_{REF}$ may also be refined over time or reinitialized according to certain criteria through a variety of filtering and estimation techniques. The methods described herein may be adapted to calculate elevation loss, or to calculate elevation gains/losses distinguished by surface grade and/or stair conditions.

The sampling rate of the sensors of the portable monitoring device may be predetermined or fixed. In one embodiment, the sampling rate is programmable or controllable. For example, in one embodiment, the portable monitoring device may control and/or determine the sampling rate of the sensors based on considerations of electrical power consumption and the rate thereof. In this regard, the portable monitoring device may employ electrical power saving circuitry and/or techniques to control and/or determine the sampling rate of the sensors.

In one embodiment, the sampling frequency of the altitude sensor ($F_{ALT}$) may be controlled, determined and/or calculated based on data from the motion sensor. For example, with reference to FIG. 9A, in one embodiment, if the motion of the user does not exceed a threshold within a time period (for example, a predetermined or programmable time period), the altitude sensor may be placed into a mode that does not sample (for example, a low power mode), or $F_{ALT}$ may be reduced or decreased. Subsequently, if the motion exceeds a threshold, for example, for a predetermined or minimum time duration, $F_{ALT}$ may be increased.

Notably, "motion" in this context is meant generally and includes features derived from raw motion sensor data. Examples would be the signal energy, variance, range, etc. The mapping of motion to $F_{ALT}$ may be a continuous function or discrete settings. In the case of one or more discrete settings (e.g., sampling modes), the features used to transition between modes are not necessarily the same, nor are the thresholds and other parameters dictating the transitions.

FIGS. 9B and 9C depict other exemplary embodiments in which the sampling mode or frequency of the altitude sensor is determined by the output of a pedometer.

Here again, the portable monitoring device senses the motion of the user and, based thereon, controls and/or determines the sampling rate of the altitude sensor. In this way, the portable monitoring device manages or controls the electrical power consumption, and the rate thereof.

FIG. 9D illustrates another embodiment where altitude sensor readings are triggered from step events detected by a pedometer, or a maximum time T between samples (whichever occurs first). Although not depicted in FIG. 9D, altitude sensor readings may be scheduled to occur after a delay from the step event. The step-space representation and models described above are suited to this type of sampling. Setting T=∞ reduces to the case where altitude readings are only generated through triggering from a pedometer.

In another embodiment, the altitude sensor may be read or its sampling mode/frequency may be controlled or set according to peaks and/or other morphological features derived from the motion sensor. For example, the sampling rate of the altimeter may be set higher and/or its measurement settings may be adjusted (e.g., to a finer setting) if the motion sensor provides a signal that is indicative of the user losing balance and/or about to fall or falling (e.g., free fall). Similarly, the sampling settings may be adjusted to capture fast transient elevation changes that may be experienced during jumping with one's legs or by other means (e.g., skateboard, skis and snowboard, pole vaulting, and the like—the settings being determined by data from the motion sensor that is indicative of the activity).

The aforementioned discussions in connection with FIGS. 8A-8H and 9A-9D may be implemented in conjunction with any of technique to calculate calorie burn, including the techniques described and illustrated herein. All permutations and combinations of (i) calculating elevation or altitude change and (ii) altitude sampling techniques, and (iii) techniques to calculate calorie burn are intended to fall within the scope of the present inventions. Moreover, as stated above, the inventions are not limited to processes and/or algorithms implemented in accordance with the flow charts of FIGS. 8A-8H and 9A-9D. Such flow charts are merely exemplary. The present inventions may also implement batch processing algorithms (as opposed to the real-time algorithm), the use of probabilistic classification and estimation methods such as, for example, bayesian networks, Kalman filters, EM algorithm and Metropolis-Hastings algorithm, or artificial neural networks.

Figure 1C:
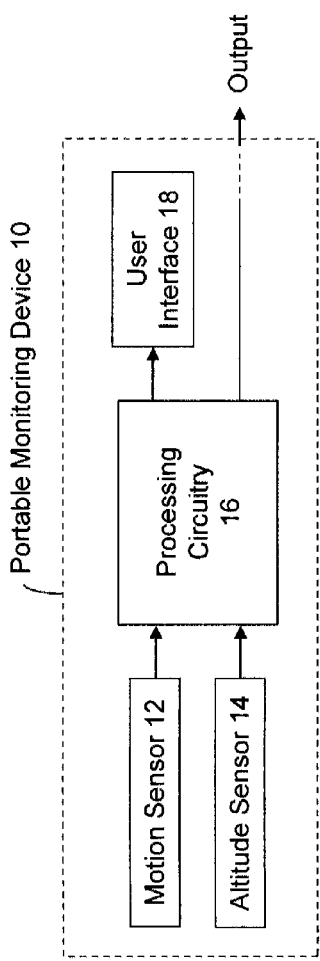

The portable monitoring device of the present inventions may also include a user interface to facilitate communication with the user. (See, for example, FIG. 1C) The user interface may include one or more displays, one or more of a speaker, microphone, vibramotor, and/or an input mechanism. (See, for example, FIGS. 10A-10F). Indeed, any manner of or mechanism for outputting and/or inputting of data and/or commands are intended to fall within the scope of the present inventions.

Figure 1D:
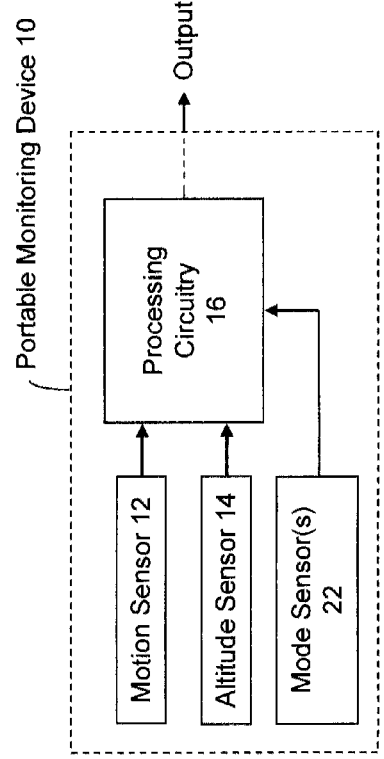

In one embodiment, the portable monitoring device includes one or more mode sensors to input, detect and/or determine a mode of movement by the user. (See, for example, FIG. 1D). For example, the user may input, detect and/or determine that the user is in a wheelchair, on a ladder, skate board, skis, snowboard and/or a bicycle. In response thereto, the processing circuitry may correlate and/or employ the data from the mode sensor(s) with the (i) data which is representative of the altitude and/or changes in altitude and (ii) data which is representative of the motion of the user, to determine, estimate, and/or calculate energy and/or calorie "burn" of the user. For example, where the user is on a bicycle, the processing circuitry may determine or calculate energy and/or calorie "burn" of the user using the (i) data which is representative of the altitude and/or changes in altitude and (ii) data which is representative of the motion of the user. Notably, the mode sensor may be responsive to a user input or detected mode of movement.

Figure 11A:
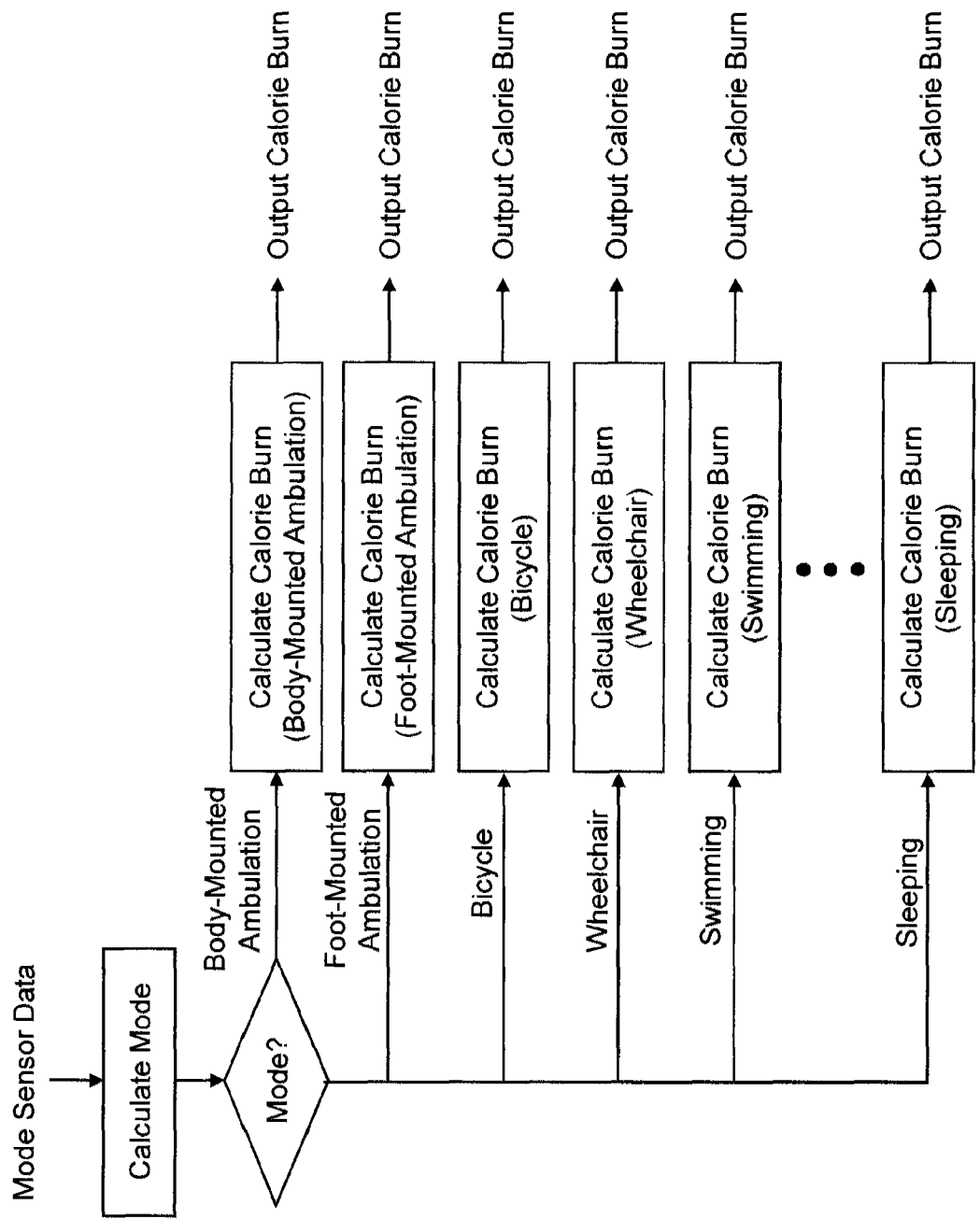
FIGS. 11A and 11B are flowcharts of exemplary processes of calculating, obtaining, assessing and/or determining calorie burn and other activity-related metrics for the user based on, among other things, data from one or more mode sensors.
Figure 11B:
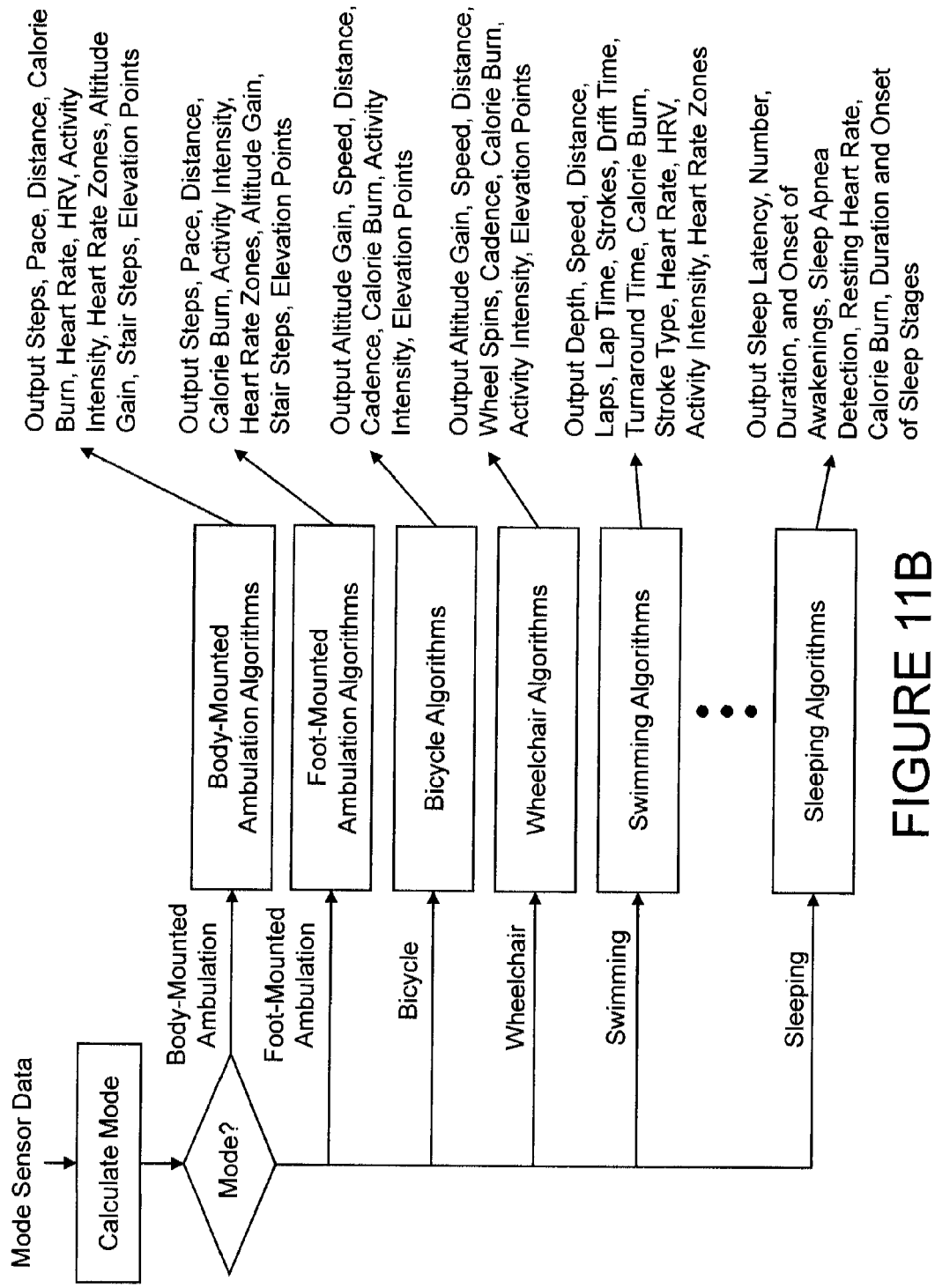

In one embodiment, FIG. 11A depicts the processing flow for the use of the mode sensor in selecting the appropriate algorithm for determining calorie "burn" of the user. Similarly, FIG. 11B depicts the processing flow for the use of the mode sensor in selecting the appropriate activity-tracking algorithms for the user based on the mode of motion or movement.

There are many mechanisms and techniques by which the mode sensor(s) may be implemented. One embodiment employs buttons and a feedback mechanism such as a graphical display, flashing lights, haptic device, piezoelectric buzzer, vibramotor, and/or speaker (all, for example, elements of the user interface) to navigate a menu system to select different modes. Another embodiment uses one or more of the motion sensors to recognize user gestures to select and deselect certain modes. In yet another embodiment, the portable monitoring device may include a user interface having an input device (for example, one or more buttons) and/or sensors that mate with specialized housings for each mode. For example, placing the device onto a designated wheelchair mounting device could push a button on the device to select a wheelchair mode. In another embodiment, device may be placed near a designated RF beacon that is affixed to a bicycle spoke, in which case the device would execute bicycle mode functionality. Other implementations may use, for example, RFIDs, magnetic sensors, LEDs and photodetectors, piezoelectric strip/material and/or strain gauges, to detect the presence of the specialized mounting apparatus. In yet another embodiment, the motion sensor(s), altitude sensor(s), and physiological sensor(s) are employed to recognize user activity and automatically select the mode.

Notably, the mode may be selected and/or determined from a plurality of pre-programmed or predetermined modes (for example, during manufacture). Such pre-programmed or predetermined modes may be stored in memory in the processing circuitry of the device. In addition thereto, or in lieu thereof, the modes may be user defined (after manufacture—for example, in situ or during operation) and programmed into or onto the device by the user at a later time and corresponding activity quantification algorithms may be adaptively "trained" or "taught" by the user.

In yet another embodiment, the portable monitoring device includes the motion sensor, altitude sensor, physiological sensor and mode sensor. Indeed, all permutations and combinations of sensors, whether in conjunction with a user interface or not, may be employed or implemented in a portable monitoring device according to the present inventions. All such combinations and permutations are intended to fall with in the scope of the present inventions.

The portable monitoring device may include transmitter circuitry to communicate energy and/or calorie "burn" of the user to, for example, an external user interface, the internet, social or media site (for example, Fitbit or Facebook) and/or computing system. (See, for example, FIG. 1F). The portable monitoring device may also output raw or pseudo-raw sensor data as well as a correlation thereof (see, for example, FIG. 6). Indeed, the portable monitoring device may output the other activity-related metrics, including, for example, (i) in the context of running/walking on level, substantially level, or relatively level ground, (a) number of steps, which may be categorized according to the number of steps associated with a user state, for example, walking, jogging and/or running, (b) distance traveled and/or (c) pace, (ii) in the context of running/walking on stairs, hills or ground having a grade of greater than, for example, about 3%, (a) number of stair and/or hill steps, which may be categorized, correlated or organized/arranged according to, for example, the speed, pace and/or activity state of the user (for example, the number of stair and/or hill steps pertaining to walking, jogging and/or running), (b) number of flights of stairs, (c) ascent/descent distance on stairs and/or hills, (d) pace, (e) ascent/descent on elevators, (f) number of calories expended by walking/jogging/running on stairs and/or hills and/or (g) quantify/compare the additional calories expended or burnt from stairs/hills relative to, versus or over level ground, (iii) in the context of swimming, number of strokes, time between strokes, leg kicks and similar metrics (variance of stroke time, mean stroke time, etc.), depth underwater, strokes per lap, lap time, pace and/or distance, (iv) in the context of using a bicycle, wheelchair, skateboard, skis, snowboard, ladder, etc., (a) ascent/descent distance traversed, (b) number of additional calories expended, (c) time of a downward "run" or upward "climb", (d) number of calories expended, (e) number of pedal rotations, (f) arm or wheel rotation, (g) the grade of the surface, (h) pushes, kicks and/or steps. This list of activities (if applicable to the particular embodiment) is merely exemplary and is not intended to be exhaustive or limiting of the inventions to, for example, the precise forms, techniques, flow, and/or configurations disclosed.

The portable monitoring device of the present inventions may include communication circuitry which implements or employs any form of communications (for example, wireless, optical, or wired) and/or protocol (for example, standard or proprietary) now known or later developed, all forms of communications and protocols are intended to fall within the scope of the present inventions (for example, Bluetooth, ANT, WLAN, Wi-Fi, power-line networking, all types and forms of Internet based communications, and/or SMS); all forms of communications and protocols are intended to fall within the scope of the present inventions.

Figure 1G:
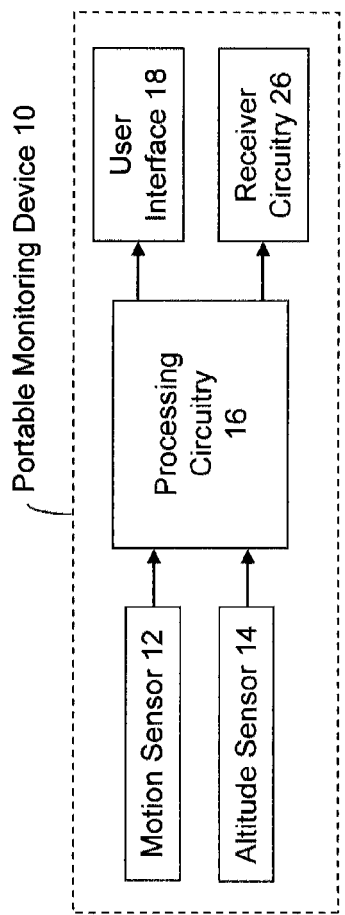
Figure 1H:
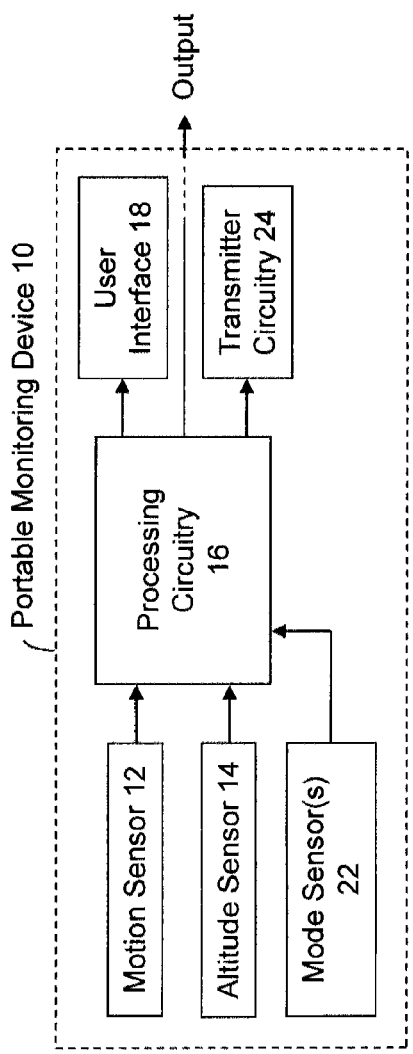
Figure 1I:
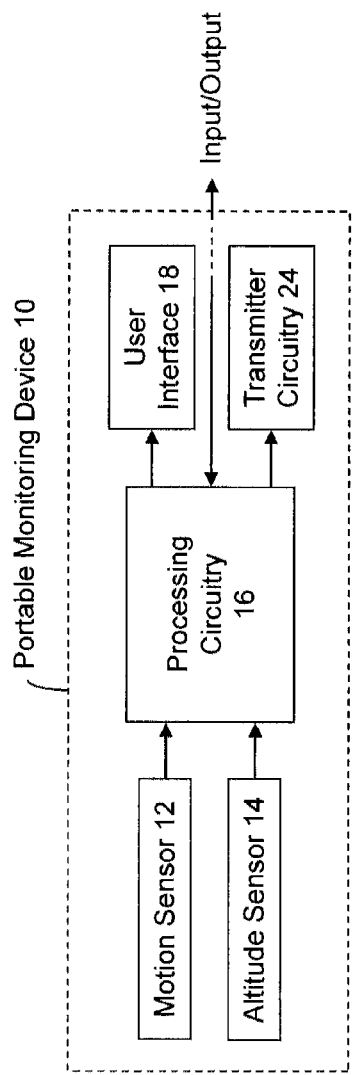
Figure 1J:
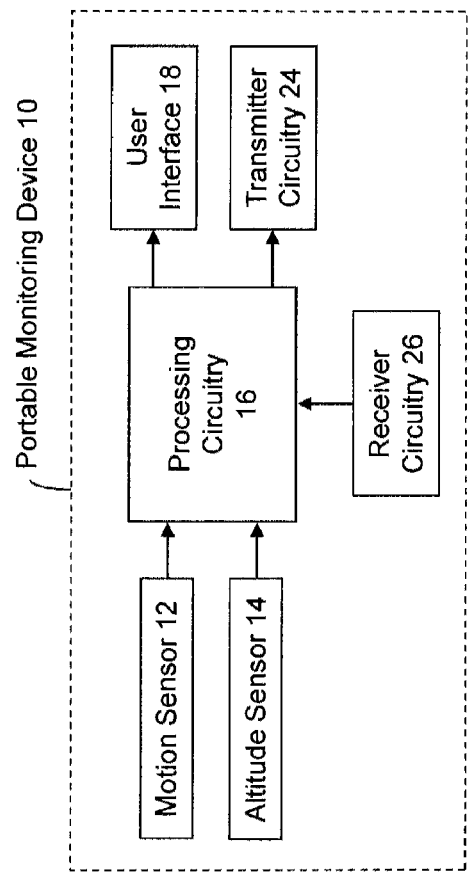
Figure 1M:
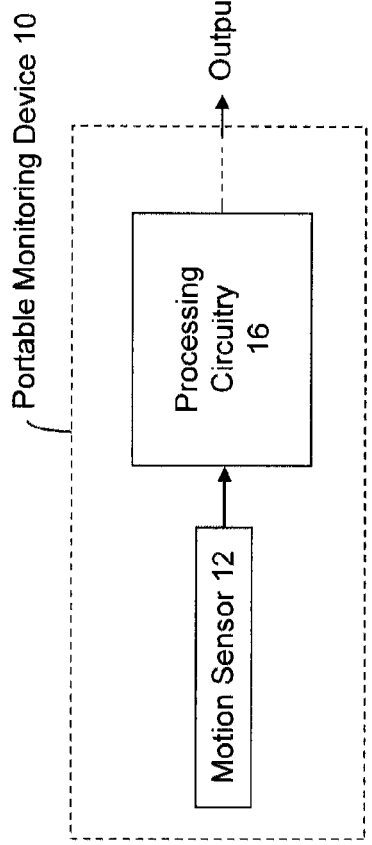
FIGS. 1M-1X are block diagram representations of exemplary portable monitoring devices, according to at least certain aspects of certain embodiments of the present inventions, wherein the portable monitoring devices, according to at least certain aspects of certain embodiments of the present inventions, include one or more motion sensors, and, in certain embodiments, may also include processing circuitry, transmitter circuitry and/or receiver circuitry, one or more physiological sensors, and one or more mode sensors.
Figure 1N:
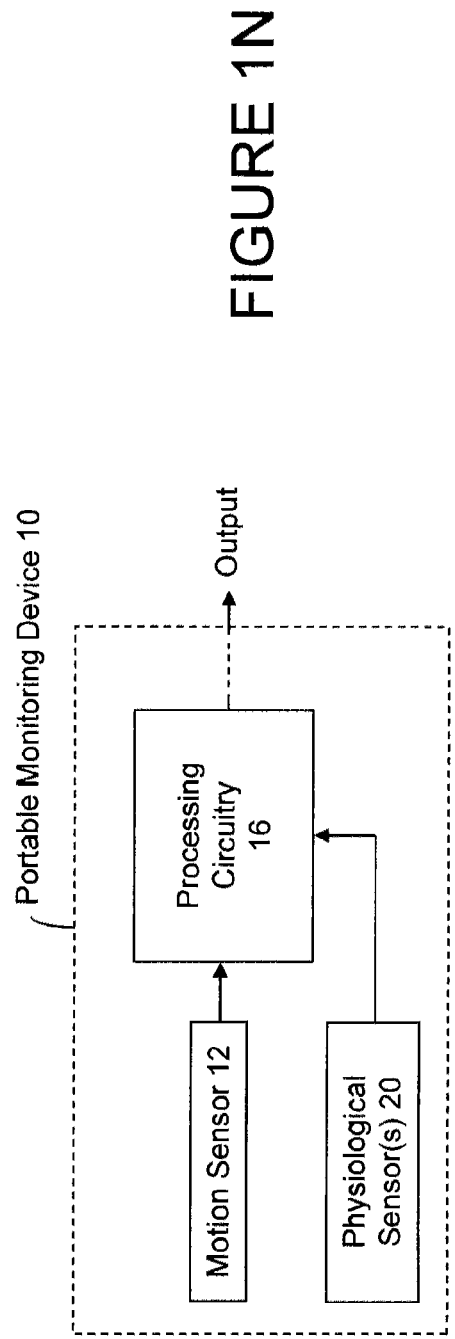
Figure 1O:
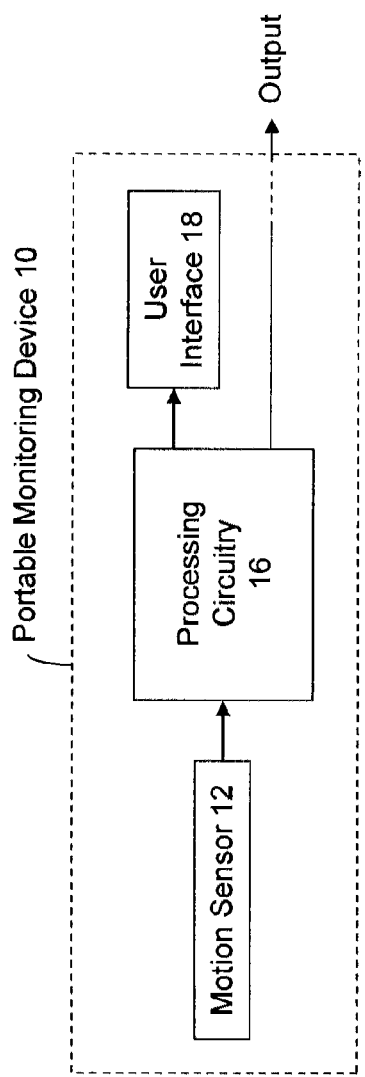
Figure 1P:
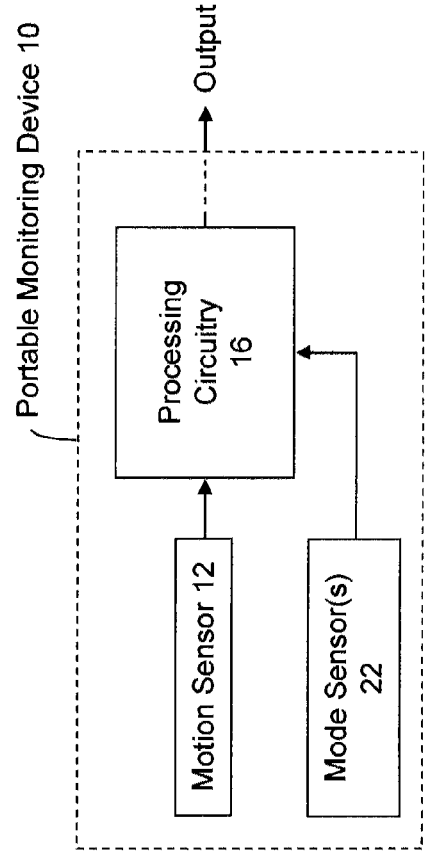
Figure 1Q:
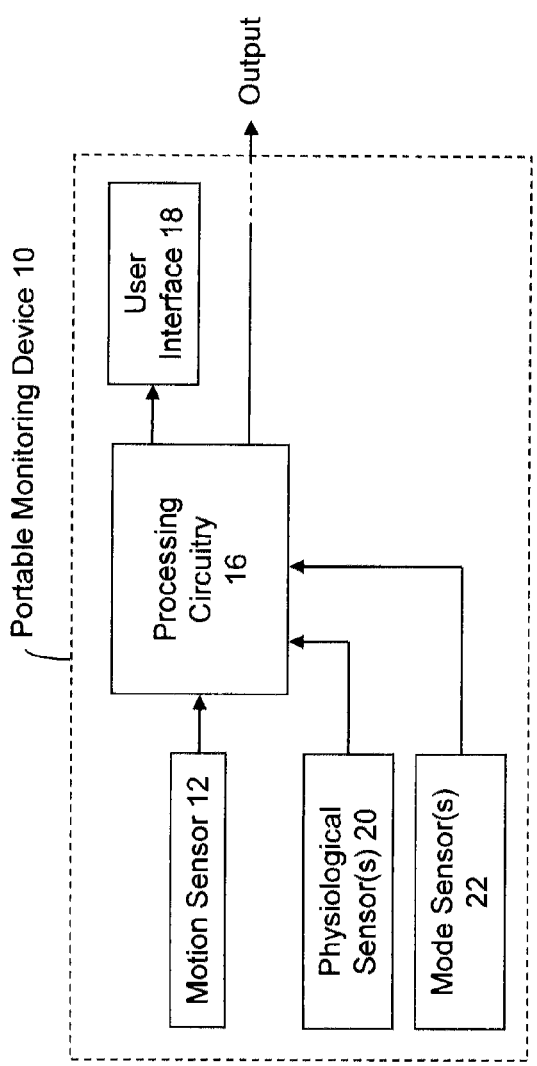
Figure 1R:
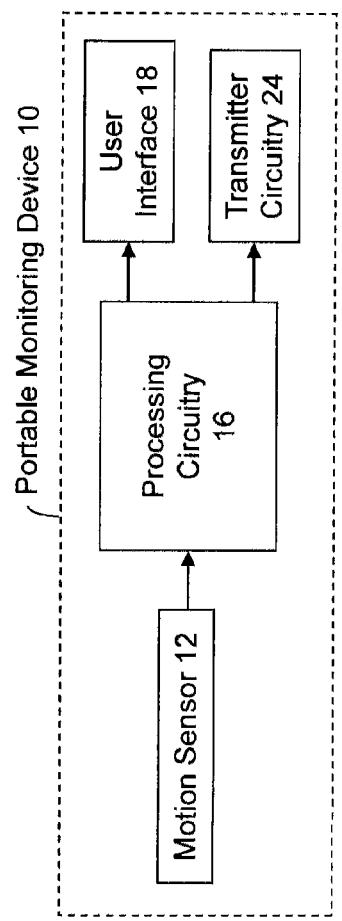
Figure 1S:
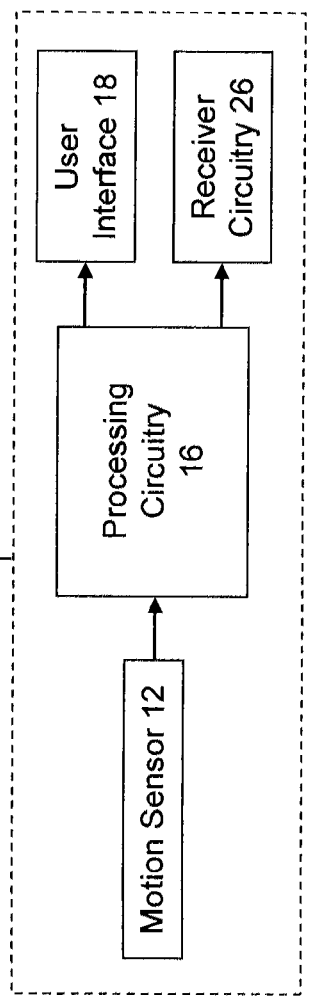
Figure 1T:
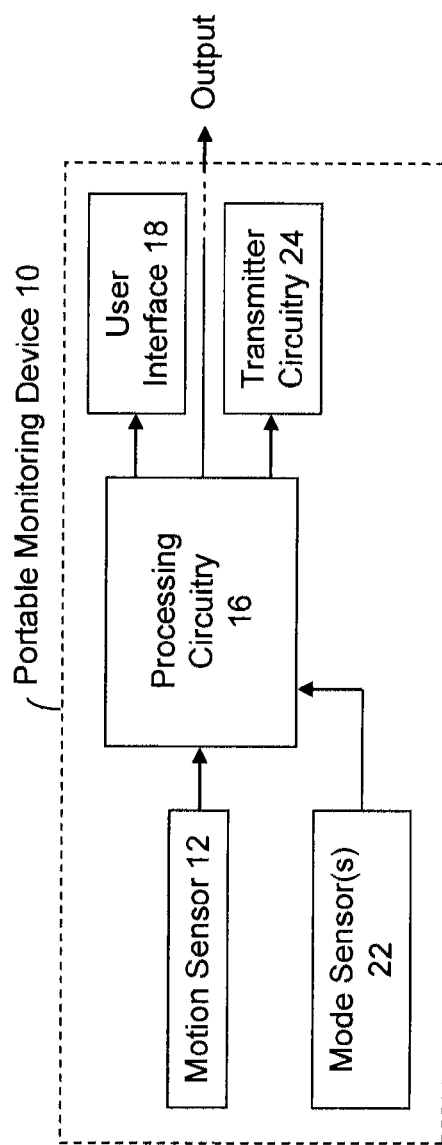
Figure 1U:
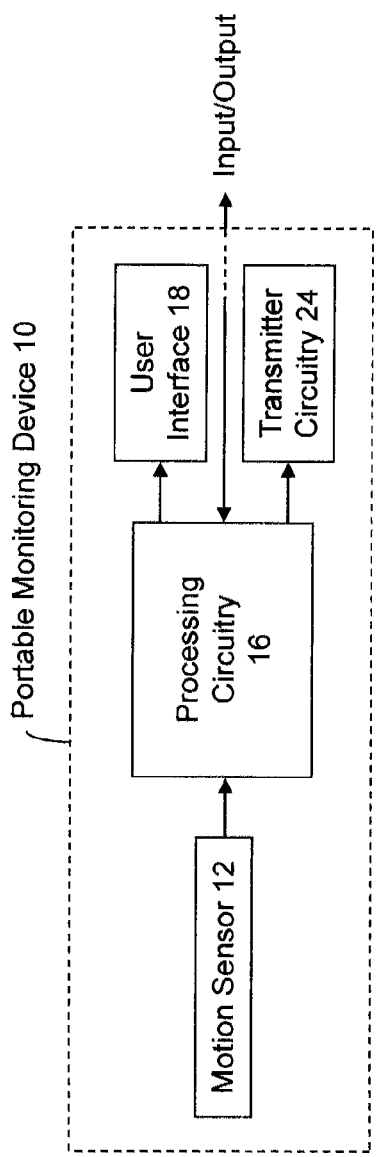
Figure 1V:
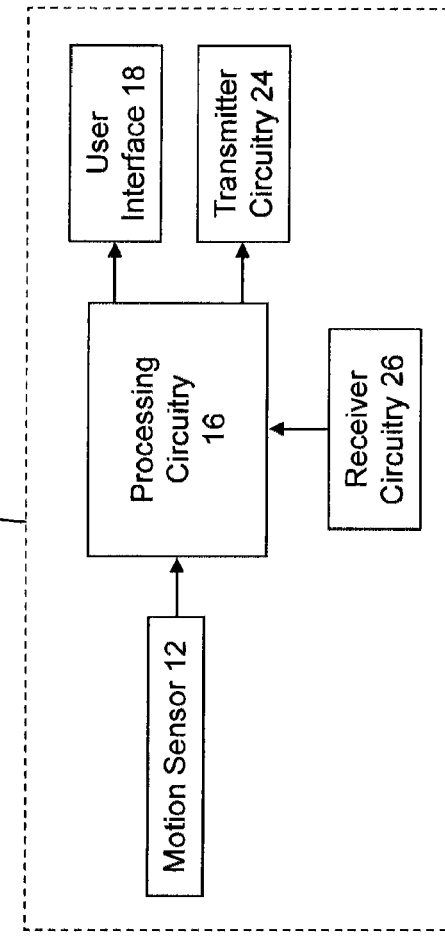
Figure 1W:
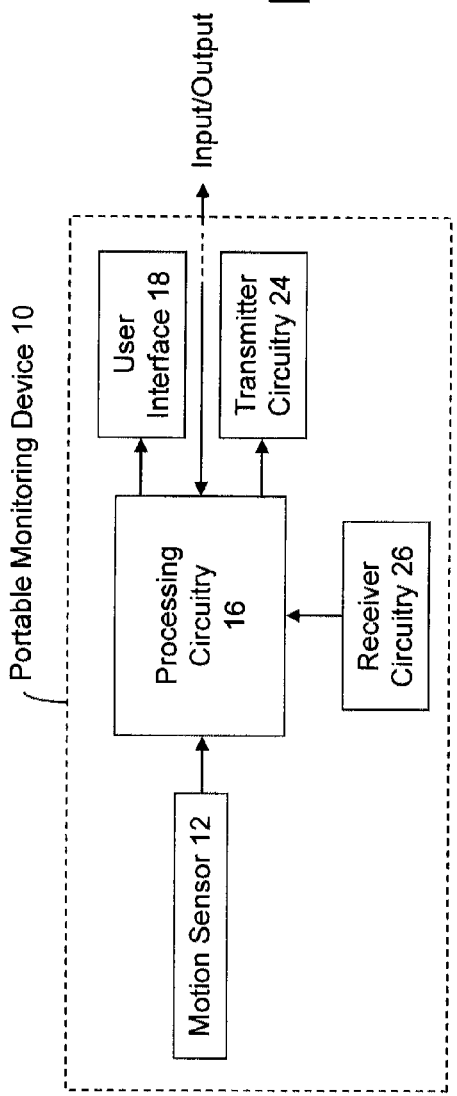

The portable monitoring device may include receiver circuitry to more fully communicate with the user and/or external circuitry. (See, for example, FIG. 1G). For example, the portable monitoring device may receive external data or commands regarding exercise time, energy use and/or calorie "burn", and milestones, for example, from the internet, social or media site (for example, Fitbit or Facebook) and/or computing system; all forms of receiver circuitry and receiving protocols are intended to fall within the scope of the present inventions.

Figure 1X:
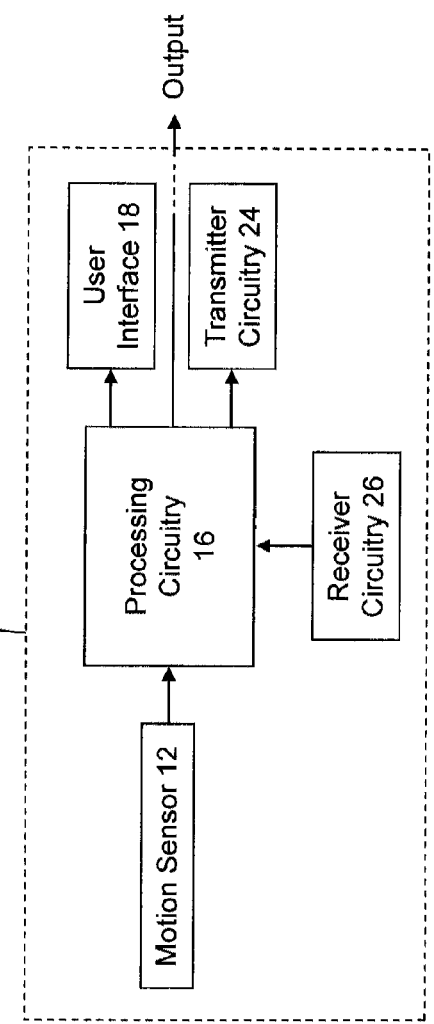

Again, all permutations and combinations of sensors, user interface, transmitter circuitry and receiver circuitry, may be employed or implemented in a portable monitoring device according to the present inventions. (See, for example, FIGS. 1A-1X). All such combinations and permutations are intended to fall with in the scope of the present inventions.

As such, the portable monitoring device of the present inventions may interface or communicate via any connectivity and protocol (for example, wired, wireless, electrical and/or optical and/or all types and forms of USB and/or removable memory). All communication mechanisms, techniques and architectures are intended to fall within the scope of the present inventions. Thus, the portable monitoring device may employ wired and/or wireless transmitter circuitry to communicate energy and/or calorie "burn" of the user to, for example, an external user interface, the internet, social or media site (for example, Fitbit or Facebook) and/or computing system. (See, for example, FIG. 1F). As noted above, the portable monitoring device may also output raw or pseudo-raw sensor data as well as a correlation thereof (see, for example, FIG. 6). Indeed, the portable monitoring device may be communicate energy and/or calorie "burn" or expenditure of the user (or such raw or pseudo-raw sensor data), for example, via transmitter circuitry, removable memory, wireless and/or wired (for example, electrical or optical) communication.

For example, in one embodiment, the portable monitoring device may be placed into a data transfer mode (for example, via engagement with a dock station, user input/instruction and/or proximity to base device) in which the display and/or suitable visual elements are used to transmit data, for example, to a base device (for example, a mobile phone, computer and/or internet portal device (for example, a router)). The base device may include one or more visual monitoring devices. In one embodiment, for example, the portable monitoring device may transmit data by switching on/off LCD segments, switching on/off individual or clusters of display pixels, and/or modulating the intensity and/or color of display pixels in the display of the user interface while base device (for example, mobile phone) monitors the display sequence with a camera and/or video camera. The data may be transmitted in any format now known or later developed including a suitable human readable format (for example, numbers and words), a binary sequence of bits (for example, bar code), or otherwise.

In another embodiment, the portable monitoring device includes or provides for bidirectional communication of the second portable monitoring device and/or a base device. In this embodiment, the second device controls a light source (e.g., camera phone flash, different colors on screen, pixels on/off) and the portable monitoring device analyzes and/or monitors the visual sequence with one or more visual sensors. This method of data transfer and communication may remove the need for additional wireless and/or wired hardware for transmitting data from the invention to another device, which itself may transfer the data to another service (e.g., www.fitbit.com).

As discussed herein, the display of the user interface may be the primary mechanism of displaying information to the user. That display may be placed into a mode to facilitate or execute an optical transfer communication. In other embodiments, the portable monitoring device may have specific visual sources that are only intended for data transfer, as well as the combination of both the primary user display and a data transfer display.

Notably, because alignment and placement of the portable monitoring device with a second device are important to the transfer process, either or both of the devices may have on-screen guides or instructions to aid alignment and placement. In one embodiment, the second device may show a template overlaid in its video display to help the user place the invention correctly relative to the second device. The portable monitoring device may have visual landmarks (e.g., borders, buttons, colors, and/or display elements) that enable the second device to visually track certain aspects of the portable monitoring device during data transfer. Visual tracking may also provide the user with alignment cues to improve placement (e.g., arrows). These same strategies may be employed by the portable monitoring device in cases of bidirectional communication.

The portable monitoring device may be equipped with one or more vibramotors, buzzers, and/or speakers with which to alert the user. For instance, the device may buzz or emit a sound to encourage the user to walk or move after observing a sedentary period of 30 minutes or more. The device may buzz or emit a sound in order to notify the user that the battery level is low. The device may buzz or emit a sound to act as a time-based alarm. Indeed, all manner of audible and/or haptic alerts are considered to be within the scope of the present inventions.

There are many inventions described and illustrated herein. While certain embodiments, features, attributes and advantages of the inventions have been described and illustrated, it should be understood that many others, as well as different and/or similar embodiments, features, attributes and advantages of the present inventions, are apparent from the description and illustrations. As such, the above embodiments of the inventions are merely exemplary. They are not intended to be exhaustive or to limit the inventions to the precise forms, techniques, materials and/or configurations disclosed. Many modifications and variations are possible in light of this disclosure. It is to be understood that other embodiments may be utilized and operational changes may be made without departing from the scope of the present inventions. As such, the scope of the inventions is not limited solely to the description above because the description of the above embodiments has been presented for the purposes of illustration and description.

Figure 12A:
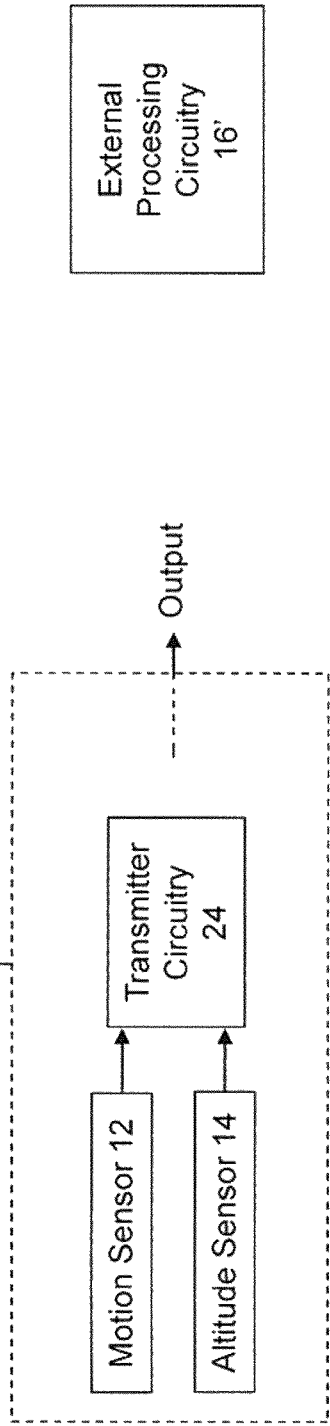
FIG. 12A is a block diagram representation of exemplary portable monitoring devices, according to at least certain aspects of certain embodiments of the present inventions, wherein the portable monitoring devices, according to at least certain aspects of certain embodiments of the present inventions, includes an altitude sensor and a motion sensor, and wherein the processing circuitry is external to the portable monitoring devices calculates or determines energy and/or calorie "burn" and/or other activity metrics due to activity of the user using altitude and motion sensor data; notably, other embodiments of the portable monitoring device of this aspect may also include one or more physiological sensors, one or more mode sensors, transmitter circuitry and/or receiver circuitry; for example, any portable monitoring device of the present inventions may employ or be implemented in any embodiment where the processing circuitry is disposed external to the portable monitoring device.

For example, in one embodiment, the portable monitoring device of the present invention includes an altitude sensor and motion sensor (and in certain embodiments other sensors such as one or more physiological sensors and/or one or more mode sensors). In this embodiment, the portable monitoring device, however, may not include processing circuitry to monitor, calculate, determine and/or detect energy and/or calorie "burn" due to physical activity of the user (for example, a human or non-human animal). In this embodiment, some or all of the monitoring, calculating, determining and/or detecting may be implemented "off-device" or external to the portable monitoring device. Here, the portable monitoring device may store and/or communicate (i) data which is representative of the altitude and/or changes in altitude of the user and/or (ii) data which is representative of motion of the user to external processing circuitry wherein such external processing circuitry may monitor, calculate, determine and/or detect energy and/or calorie "burn" due to physical activity of the user. (See, FIG. 12A). Such external circuitry may implement the calculation processes and techniques in near real-time or after-the-fact. The data which is representative of the (i) altitude and/or changes in altitude of the user and/or (ii) motion of the user may be communicated to such external processing circuitry, for example, via transmitter circuitry (see FIG. 12A), removable memory, electrical or optical communication (for example, hardwired communications via USB). Importantly, such an architecture/embodiment is intended to fall within the scope of the present inventions.

Moreover, the portable monitoring device of this embodiment (i.e., external processing circuitry) may include all permutations and combinations of sensors (for example, one or more physiological sensor(s) and/or mode sensor(s). For example, the portable monitoring device of the present inventions may include one or more altitude sensors (see, for example, FIGS. 1A-1L); in other embodiments, the portable monitoring device does not include one or more an altitude sensors (see, for example, FIGS. 1M-1X).

Figure 12B:
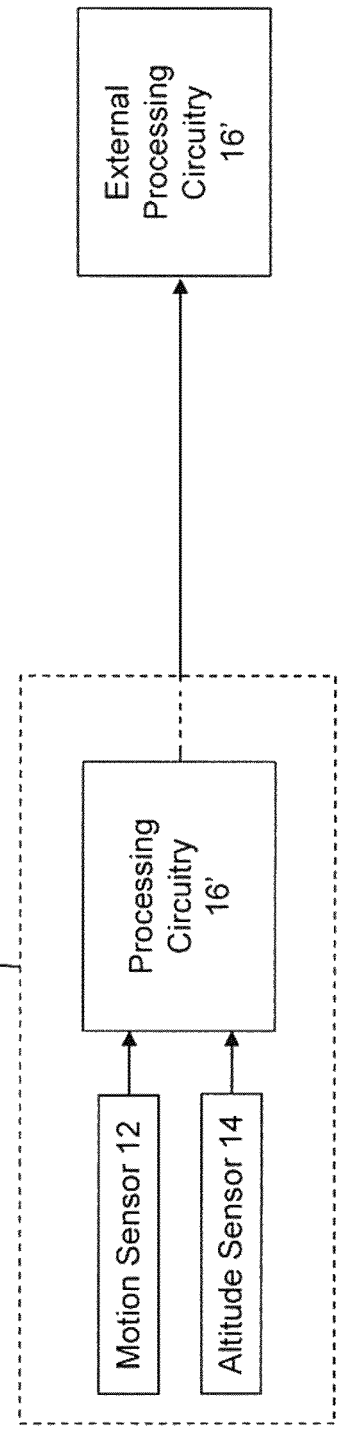
FIG. 12B is a block diagram representation of exemplary portable monitoring devices, according to at least certain aspects of certain embodiments of the present inventions, wherein the portable monitoring devices, according to at least certain aspects of certain embodiments of the present inventions, includes an altitude sensor, a motion sensor, and certain processing circuitry—wherein certain other processing circuitry is external to the portable monitoring devices and the processing circuitry, in combination, calculates or determines energy and/or calorie "burn" and/or other activity metrics due to activity of the user using altitude and motion sensor data; notably, other embodiments of the portable monitoring device of this aspect may also include one or more physiological sensors, one or more mode sensors, transmitter circuitry and/or receiver circuitry; for example, any portable monitoring device of the present inventions may employ or be implemented in any embodiment where the processing circuitry is disposed external to the portable monitoring device.

Notably, in one embodiment, the processing circuitry to monitor, calculate, determine and/or detect energy and/or calorie "burn" due to physical activity of the user may be distributed between resident circuitry and external circuitry. (See, FIG. 12B). In this embodiment, circuitry disposed in the portable monitoring device may implement certain processes and algorithms and the external processing circuitry may implement other processes and algorithms wherein, the circuitry, in combination, monitors, calculates, determines and/or detects energy and/or calorie "burn" due to physical activity of the user.

In another embodiment, the exemplary portable monitoring devices may employ a MEMS altitude sensor. In this regard, the altitude sensor includes a MEMS pressure sensing structure to generate data which is representative of the altitude of the structure. For example, with reference to FIG. 13, in one embodiment, the MEMS pressure sensing structure includes a multi-diaphragm structure wherein a first diaphragm 1 is more fully exposed to changes in the ambient environment relative to a second diaphragm which is less exposed to changes in the ambient environment due to a plurality of micro-pores 3. The diaphragms 1 and 2 form a portion of a sealed chamber (for example, vacuum-sealed chamber). In one embodiment, the MEMS pressure sensing structure includes a pressure sensing element 5 to sense, sample, determine and/or obtain changes in pressure. Here, first diaphragm 1 is responsive to the environment with low pneumatic impedance so that there is effectively no latency. The second diaphragm is responsive to the environment through micro-pores that "delay" the rate of change of the pressure. This difference may deflect the bidirectional pressure sensing element 5 toward the side with lower pressure.

Figure 13:
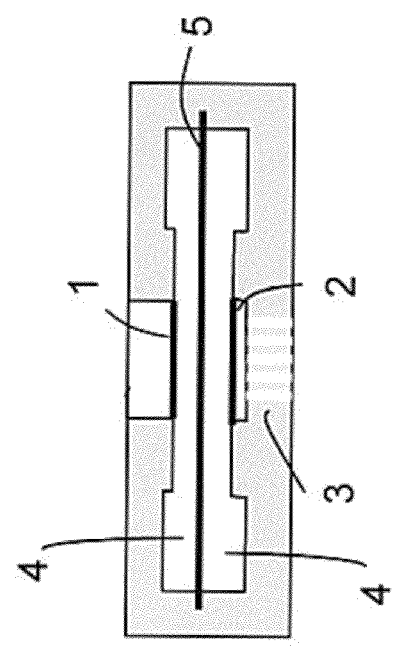
FIG. 13 is a cross-sectional representational view of an altitude sensing microelectromechanical system (MEMS) to sense, sample, determine and/or obtain altitude data, according to at least certain aspects of certain embodiments of the present inventions; notably, the altitude sensing MEMS of FIG. 13 may be incorporated in any of the exemplary portable monitoring devices of the present inventions.
Figure 14:
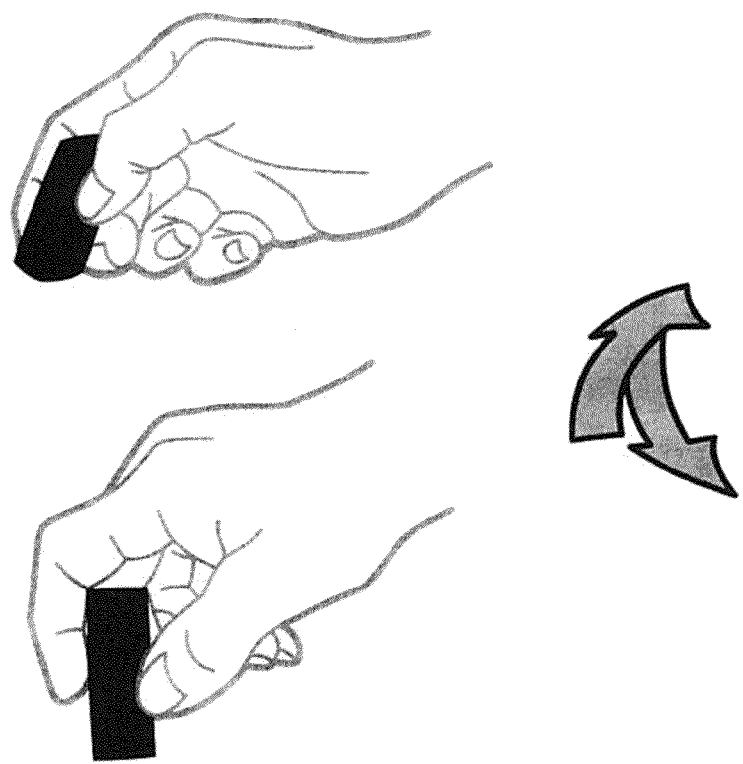
FIG. 14 illustrates an exemplary gesture of the portable monitoring device that is mostly contained in the orthogonal plane to the gravitational vector which may be used as a user interface mechanism (e.g., to navigate a menu system)

The sensor structure depicted in FIG. 13 is just one embodiment of one aspect of the inventions. The chambers on either side of the bi-directional sensing element need not be equal in size and either or both sealing diaphragms 1 and 2 may be omitted in some embodiments. For instance, the element producing the pneumatic impedance that delays pressure changes may effectively seal the chamber from contaminants because the element is a continuous polymer film.

In operation, the deflection in pressure sensing element 5 provides information which is representative of the change in altitude (due to changes in pressure). That is, the micro-pores "delay" the rate of pressure change caused by the second diaphragm in response to small changes in altitude relative to the first diaphragm (which has a low pneumatic impedance path to ambient). The deflection of in pressure sensing element 5 may be measured via changes in stress or strain in pressure sensing element 5. In addition thereto, or in lieu thereof, the deflection may be measured by changes in capacitance or voltages of sensing plates (not illustrated).

Pressure equalization in a single-pore system can be expressed analytically for a simplified system. Assuming the inner chamber has volume V and is subject to a pressure difference of $\Delta p$ which is much less than the absolute pressure p (i.e., $\Delta p \ll p$) and that the inner chamber is exposed to the external environment through a hole of radius r and that the system has low Knudsen number, the mean velocity of gas flow at the orifice is $$u = -\frac{r}{3\pi\eta}\Delta p,$$

where $\eta$ is the viscosity of the gas (Roscoe 1949, Yu, et al. 1988). The rate of change of the mass of gas in the chamber is $$\dot{m} = -\rho\pi r^2 u,$$

where $\rho$ is the density of the gas.

Finally, assuming the gas to be ideal and the system to be isovolumetric and isothermal, it can be shown that the rate of change of pressure in the chamber $p_c$ is $$\dot{p}_c = \left(\frac{\rho RT}{3\eta M}\right)\left(\frac{r^3}{V}\right)\Delta p,$$

where R is the universal gas constant, T is the temperature, and M is the molar mass of the gas.

As such, it can then be shown that the time constant for the system $\tau$ is $$\tau = \left(\frac{3\eta M}{\rho RT}\right)\left(\frac{V}{r^3}\right).$$

For illustration, operating at standard temperature and pressure, representative numbers for air are $M=0.0289$ kg mol$^{-1}$, $\eta=1.8369\times10^{-5}$ Ns m$^{-2}$, $\rho=1.2041$ kg m$^{-3}$. Assuming the chamber to be a 1 mm cube ($V=10^{-9}$ m$^3$), a 1 sec time constant (i.e., $\tau=1$ sec) can be achieved with a hole of size r=0.816 µm. The Knudsen number of the system is 0.04<<1 so the preceding assumption of small Knudsen number is appropriate.

In the preceding analysis, the effects of a finite length to the orifice (so that it acts as a channel) and other parasitic effects such as surface tension are omitted. These effects increase the pneumatic resistance of the pore and enable it to be sized larger for a given time constant $\tau$. It is assumed that one skilled in the art can derive a similar expression or use simulation to account for these effects. The atmospheric permeability of thin polymeric membranes that can also be applied across macro-sized holes in the relatively deep silicon walls of a MEMS produced pressure chamber, or cover arrays of micro-machined surface channels leading to such a chamber can be employed and are well understood. For instance, the $O_2$ permeability of various common polymers was documented by Robb (1968) to span more than 5 orders of magnitude, making selection of a suitable thickness of gas permeable membrane more a choice of manufacturing convenience then of limited alternative chemistries.

Similarly, gas porous silicon membranes capping a chamber or channels leading to a chamber can be made by MEMS processes with bulk etching & processing techniques to produce predictable gas permeability characteristics. For instance, Galambos, et al. (1999) demonstrated that silicon nitride ($Si_3N_4$) could itself be etched to produce a gas permeable filter in a micromachined channel. More generally, Wu (2004) described the properties of porous polycrystalline membranes etched on $Si_3N_4$ using MEMS technology to cover cavities. MEMS processing techniques may produce a membrane structure with stochastically predictable micro cracks or pores that facilitate atmospheric gas flow, without the need for precisely machined orifices.

Importantly, the present inventions are neither limited to any single aspect nor embodiment, nor to any combinations and/or permutations of such aspects and/or embodiments. Moreover, each of the aspects of the present inventions, and/or embodiments thereof, may be employed alone or in combination with one or more of the other aspects and/or embodiments thereof. For example, while many of the inventions have been described in connection with a portable monitoring device including one or more altitude sensors (see, for example, FIGS. 1A-1L), many of the inventions may be implemented in connection with a portable monitoring device which does not include one or more an altitude sensors (see, for example, FIGS. 1M-1X). For the sake of brevity, many of those permutations and combinations will not be discussed and/or illustrated separately herein.

Notably, although exemplary embodiments and/or processes have been described above, the inventions described and/or illustrated herein may also be implemented in conjunction with other activity metric determination techniques. As such, the inventions are not limited to processes and/or algorithms implemented in accordance with the flow charts of FIGS. 4A-4R; rather, such flowcharts are merely exemplary.

Further, the portable monitoring device may communicate with external circuitry using the transmitter circuitry (see, for example, FIGS. 1F, 1H-1L, 1R and 1T-1X), receiver circuitry (see, for example, FIGS. 1G, 1J-1L, 1S, and 1V-1X), removable memory, electrical or optical communication or connector (for example, hardwired communications via USB).

As mentioned above, the portable monitoring device may store and/or transmit the raw data or pseudo-raw (i.e., processed) data from on or more (or all) of the sensor(s). For example, in the context of the motion sensor, the portable monitoring device may store and/or transmit data which is representative of acceleration, angular rate, location and/or compass bearing. In the context of the altitude sensor, in one embodiment, the portable monitoring device may store and/or transmit data which is representative of pressure, altitude, time of flight and/or radar cross section. Further, in the context of the physiological sensor(s) and naturally-derived metrics, the portable monitoring device may store and/or transmit data which is representative of heart waveform (for example, ECG trace), heart rate, blood sugar, blood pressure and/or EEG. In addition, in one embodiment, the portable monitoring device may store and/or transmit data provided by the mode sensor(s) including, for example, bicycling, swimming, skateboard or wheel chair.

Notably, the data which is stored and/or transmitted may be filtered versions of the aforementioned, for example, filtered using passive elements (for example, RC networks) and/or active elements (for example, active electronics), frequency-domain methods (Butterworth filter, etc), statistical methods (Kalman filter, etc), time-series analysis (ARX models, etc) and/or wavelets.

The raw or pseudo-raw (for example, filtered versions) of the aforementioned data may be stored and/or transmitted in time epochs that differ from the original (e.g., 1 Hz instead of 100 Hz) or in summary versions (e.g., mean, variance, integral, power, coefficient of variation, etc.) and may include signal quantities that are derived typically for use in a classification algorithm and other downstream calculations. In addition, the raw or pseudo-raw (for example, filtered versions) of the aforementioned data may be stored and/or transmitted in compressed or uncompressed formats. Such data may also be stored and/or transmitted in a matched to a value format that, for example, captures the approximate or exact value of the data (e.g., look-up table, ranges like "small", "medium" and "large").

The data and parameters derived by the portable monitoring device may be transferred, displayed, and/or modified remotely as in, for example, a computer program or website such as www.fitbit.com. Such content may furthermore be modified by the remote application and transferred back to the device for storage and display. For example, the user may adjust information regarding one or more physiological parameters that effect metabolism, which in turn are used to correct calorie burn estimates on the portable monitoring device. Likewise, the user may adjust information regarding height, step length, the intensity of a workout, the type of activity over a particular time duration (e.g., walking, running, weight lifting, driving or riding in an automobile, etc.) and this information may be used to adjust estimates of calorie burn, distance traveled, speed, avatar state, and other activity-related metrics stored and/or displayed on the portable monitoring device.

Data and derived parameters from one or more of the present inventions and/or one or more other devices may be stored, displayed, and/or modified remotely as in, for example, a computer program or website such as www.fitbit.com. The devices may generate their data independently, operate dependently upon one another (e.g., as accessories to one another), or both. The remote application may combine the data or generate new data which is then displayed in the remote application and/or other remote applications and/or the portable monitoring device of the present inventions and/or other devices. The remote application may also overlay the data to the user to present a holistic view of the data streams obtained from multiple devices. For example, two devices (called "Device A" and "Device B" for simplicity here which are respectively a pedometer and heart rate monitor) may generate data streams representative of user activity and/or physiological information which is transferred to www.fitbit.com. The user may create a data stream of manually or automatically annotated events on Device B, which are subsequently used by www.fitbit.com to override or modify the data from Device A during the same periods of time as the annotated events. The annotated events may likewise be presented in a manner that attracts user attention preferentially to the data of Device B. Notably, the data that is overridden or modified may be transferred back to Devices A and B for storage and/or display to the user.

In addition, the portable monitoring device may also facilitate social interaction features. In one embodiment, the portable monitoring device may contain user identification "credentials" (for example, stored in memory) that communicate with second or base devices to link a plurality of users (for example, two users) in a social network (for example, via the internet or device-to-device). The second device may or may not be a portable monitoring device according to one or more of the embodiments of the present inventions. As an example, two people may link their devices to become "friends" on www.facebook.com, www.fitbit.com, www.linkedin.com, and/or other social networks. The "friend" status may be may be passed to the internet directly from the device or routed through intermediate devices (e.g., Fitbit Tracker to mobile phone to internet). Linking of devices may be achieved in a variety of well-known ways for pairing two devices. In one embodiment, the two devices may be linked through a bump gesture or physical tapping (e.g., contact) of the two devices that initiates wireless communication between the two. A combination of motion sensing (e.g., accelerometer and/or gyro), and/or magnetic signature sensing, and/or wireless (e.g., NFC, RFID, RF proximity sensing) may be employed.

In other embodiments, the portable monitoring device may provide user contact information such as email addresses, telephone numbers and/or a user name, which may be transmitted when the devices are linked. The device may be configured to transmit only specific pieces of contact information.

In other embodiments, the portable monitoring device may monitor, catalog and/or track the number, duration, frequency, and quality of social interactions between two or more people in a social network. As an example, the portable monitoring device may use wireless proximity detection between portable monitoring devices to determine, monitor, catalog and/or track episodes in which the devices were in the same proximity, for example, to determine, monitor, catalog and/or track the amount of time two users spent time with one another. Summary metrics like the duration of interaction, frequency of meetings, physical distance, etc. are exemplary parameters of interest.

In another embodiment, the portable monitoring device may include one or more audio sensors to monitor, determine and/or track the quality and/or tone of conversation between the user and others (with or without a similarly-equipped device). In yet another embodiment, the same interactions between "friends" in a social network are specifically monitored, cataloged and/or tracked.

In another embodiment, the portable monitoring device may interact with other devices through wireless communication to allow the user to play a game. For example, a pair of devices may be bumped together to initiate a game-like contest between the two users based on their step counts. Other examples may include animated virtual "fight" sequences between avatars placed on both devices. The users' devices may buzz, glow, etc. to notify the users that there is another contestable device nearby. It may do this for "friends" only or for anyone with an appropriate device. The contest may follow deterministic behavior or probabilistic behavior.

Again, in the context of the aforementioned embodiments, the devices may consist of the portable monitoring device according to any of the embodiments described herein and a second device, which may be a second portable monitoring device or may be a different device (for example, a mobile phone or tablet).

Notably, the use of "wireless" also extends to visual and/or magnetic detection and identification of compatible devices. For instance, the invention may have a magnetic field sensor that can recognize the magnetic signature of compatible devices.

As noted above, the portable monitoring device may contain user identification credentials (for example, stored in memory). Here, the portable monitoring device may enable the user to authenticate to certain services or be automatically recognized. For instance, a user attempting to login to "www.fitbit.com" from a computer may be automatically routed to the appropriate, designated, associated and/or correct user account and bypass authentication steps by placing the portable monitoring device into a specific authentication mode, or by virtue of proximity detection of the device by the computer.

Likewise, the user may be automatically identified when approaching other devices that are configured to recognize the invention. For instance, the user may be recognized as she approaches a weight scale that communicates with her device.

In situations where a plurality of portable monitoring devices are "present" in a single location (e.g., a family where each family member owns a device), it may be useful for each portable monitoring device to have a unique identifier so that a user associated with which device may be determined. The indicator may be chosen by the user or it may be preprogrammed onto the device. The indicator may be turned off or disabled by the user. In one embodiment, when the device is placed stationary (e.g., display side up on a table surface) and then subsequently moved or jolted, it displays the indicator. The display may also show other content such as motivational messages, general messages, animations, graphics, etc. In another embodiment, the device may show the same or similar information through an input from the user through the user interface. In yet another embodiment, the device may display the same or similar information when the device is coupled to or removed from a specific fixture (e.g., charger) or put in proximity of fixture (e.g., RF beacon, magnetic source). The unique identifiers comprise a specific color shown on a multicolor LED, color/animation sequence, nickname/keyword, word sequence, vibration sequence, custom avatar, or image.

In one embodiment, the portable monitoring device has a RFID and/or NFC tag embedded in it. The tag may be either read or write. If the tag is read-only, then it stores some static information about the device, for instance, a unique identification number. If the tag is read and write, then either a NFC writer device can write to it or an onboard MCU is connected to the tag and can write to it. If another device equipped with a NFC reader (e.g., smartphone) is brought in proximity to the device, then an app (e.g., Fitbit mobile app) launches automatically and transfers data with the device (e.g., communication to and from www.fitbit.com). If the application "knows" the portable monitoring device (e.g., it is set up to recognize the device), then it transfers data. If the application sees that the device belongs to someone else, it offers the ability to "friend" that person or establish a similar relationship. It may also show some personal information about the user, who may be a human or nonhuman animal. If the application sees that the device is an unknown device, it offers a setup option. Data transfer functionality may occur directly through the RFID tag itself (e.g., the RFID antenna is connected to an EEPROM that the onboard microprocessor can write to) or the RFID/NFC may act as just an automatic discovery mechanism while data transfer is over another system such as ANT, Bluetooth, Zigbee, Wifi, etc.

In one embodiment, the portable monitoring device is a multi-protocol local area network (LAN) to wide area network (WAN) gateway where local devices may be Bluetooth, ANT, Zigbee, etc. and the gateway communicates to the internet via or over a communication path (for example, a cell phone network, WLAN, etc.). The portable monitoring device may operate as an "open hotspot" so that no user setup is required for subsequent devices. For instance, a user may have elsewhere established a network account (e.g., www.fitbit.com or another website) to the device (e.g., Fitbit Tracker) through its unique device ID, then the device automatically recognizes compatible devices and sends their data to the correct account and location. The data may go directly to the destination or through an intermediary first. Destinations or intermediaries could be other devices or a network service (e.g., www.fitbit.com). The "original" portable monitoring device to account/location link setup could have been done as part of a user initiated setup process or could have been pre-configured as part of the purchasing or acquisition process at the manufacturer or another intermediary. The following is an additional exemplary embodiment:

A user owns a Garmin ANT device that is set up to sync data to Garmin's website. She then acquires the current invention. Once she connects the invention to the internet, the Garmin device can automatically send its data to Garmin's website through the invention without any further setup. The invention could also send the data to Garmin's website via an intermediary website (e.g., www.fitbit.com).

The user may also turn off and on (disable or enable) the ability for data destinations to receive the data.

The communication circuitry of the portable monitoring device may provide for one-way or two-way communication to, for example, facilitate or provide input of data and/or commands. Indeed, where the device includes two-way communications, the communication circuitry facilitates or provides data or command transmission to and from peripheral devices and/or the Internet. Thus, in certain embodiments, the communication circuitry facilitates or provides external connectivity to, for example, the Internet and/or remote or local external devices and/or appliances.

Where the communication circuitry provides one-way or two-way communication to the Internet and/or (remote or local) external devices and/or appliances, the portable monitoring device may upload data and/or commands to and/or download data and/or commands from, for example, selected websites, health professionals, trainers, weight or health oriented monitoring groups/organizations or specialists, and/or the like (hereinafter collectively "third party" or "third parties"). In this way, the portable monitoring device may manually or automatically provide data to such third parties. The portable monitoring device may also receive data and/or instructions/comments, for example, health or training guidance or feedback via the device. For example, where the portable monitoring device provides data (for example, activity levels, steps and/or sleep quality) to one or more third party devices or websites, such third parties (for example, health professionals or trainers) may monitor and/or provide feedback based on such data. In this way, such third party or parties may provide periodic, continuous and/or intermittent monitoring and/or feedback, notwithstanding the user/patient is substantially remote or distant from such third parties, or where significant monitoring of the user/patient is inconvenient or not feasible (for example, due to costs or locations).

The communication circuitry may also facilitate programming of the portable monitoring device, for example, programming the device to acquire selected data (via enabling and/or disabling selected sensors) and/or calculate, monitor and/or determine selected physiological parameters (via enabling or disabling the processing circuitry accordingly). The programming of the portable monitoring device may be via the user or third party. In this way, for example, a third party may customize or tailor the acquisition of physiological data based on the user, the situation (for example, physical condition of the user), and the acquisition of desired information.

In certain embodiments, the portable monitoring device may also operate, program and/or control local external devices and/or appliances. For example, the communication circuitry of the device may also function as a relay or hub to provide or facilitate communication for external devices to each other or to the Internet. For example, the device may connect to the Internet via WLAN but also be equipped with an ANT radio. An ANT device may communicate with the device to transmit its data to the Internet through the WLAN of the device (and vice versa). Moreover, where the communication circuitry is equipped with Bluetooth, other Bluetooth-enabled devices (for example, mobile or smart telephones) that come within suitable or effective reach or range, the device may transmit data to or receive data from such Bluetooth-enable device and/or the Internet through the network of the mobile or smart telephones. Indeed, data from another device may also be transmitted to the device and stored (and vice versa) or subsequently transmitted at a later time.

In another preferred embodiment, the portable monitoring device is a single protocol or multi-protocol wireless bridge that may relay, store, and/or display data from compatible wireless devices. Compatible devices need not be activity monitors. For example, a weight scale may transmit data of the user's weight to the device and it may display an historical graph of the user's weight. Data transfer may be bidirectional. Data may be stored and later transferred through the device's wireless communication circuitry to other services such as the Internet.

In a preferred embodiment, when the portable monitoring device is placed stationary (e.g., display side up or display side down on a table surface), it attempts wireless communication with nearby compatible wireless devices. Indeed, in several embodiments a wireless communication attempt is initiated by the portable monitoring device through one or more gestures detected by the motion sensor. For instance, the device may be placed display side up on a surface for a fixed time interval then subsequently flipped to the display side down position.

As mentioned above, the portable monitoring device may include a user interface having a display. In one embodiment, the display is customizable in that the information and content of the display may be customized by the user. The user may configure the types of information "screens" as they show up on the device and in which order. This may be achieved through configuration on the device or an external application (e.g., a settings manager on www.fitbit.com). As indicated above, the portable monitoring device, in addition to monitoring, calculating and/or determining of one or more activity and physiological parameters (based on or using data from resident sensors), may receive web content for display on the user interface of the portable monitoring device. The following are examples of the types and/or content of information that may be provided to the user.

- Historical and current graphs and/or data of user activity and/or foods consumed and/or sleep data that are measured by the device and/or stored remotely (e.g., fitbit.com);
- Historical graphs and data of user weight and/or body fat data measured by a weight scale and transferred to the device (either over the Internet or by the scale itself);
- Historical graphs and data of other user-tracked data measured by the device or stored remotely. Examples include heart rate, blood pressure, arterial stiffness, blood glucose levels, cholesterol, duration of TV watching, duration of video game play, mood, etc.;
- Physiological data corresponding to average or norms, for example, for comparison purposes wherein, in one embodiment, the user's physiological data is compared to or contrasted with average physiological data (for example, on an age, gender or condition basis (for example, a pregnant women's physiological data is compared with typical physiological data based on stage, size and age));
- "Mash-up" data pertaining to user's physiologic data and user's water intake—for example, correlations of (i) hydration levels to manually logged water consumption and (ii) hydration levels to automatically measured water consumption via a "smart" water bottle (e.g., Camelback flow meter hydration gauge system);
- "Mash-up" data pertaining to user's physiologic data and user's sleep—for example, correlations of (i) heart rate to blood pressure and (ii) body weight and/or fat to sleep time, patterns and/or quality;
- "Mash-up" data pertaining to user's physiologic data and user's activity—for example, correlations of (i) hydration to activity levels and (ii) heart rate and/or variability to activity levels and/or patterns;
- "Mash-up" data pertaining to physiologic data and potentially related external events such as correlations of (i) user's body weight and/or fat to ambient environment for example, geography, temperature and/or weather, (ii) user's heart rate and/or blood pressure to financial markets (for example, S&P 500, NASDAQ or Dow Jones); here the data analysis of the user's biometric or physiologic data is correlated to web content and/or external devices that are in communication with the biometric monitoring device;
- Coaching and/or dieting data based on one or more of the user's current weight, weight goals, food intake, activity, sleep, and other data;
- User progress toward weight, activity, sleep, and/or other goals;
- Summary statistics, graphics, badges, and/or metrics (e.g., "grades") to describe the aforementioned data;
- The aforementioned data displayed for the user and his/her "friends" with similar devices and/or tracking methods;
- Social content such as Twitter feeds, instant messaging, and/or Facebook updates;
- Other online content such as newspaper articles, horoscopes, stock, sports or weather reports, RSS feeds, comics, crossword puzzles, classified advertisements, and websites; and
- Motivational messages, system messages (e.g., battery status, "sync data" notifier), device communications that may be similar to social content (e.g., the device may communicate greetings to the user like "Hello", "Good Morning"), and/or other messages similar in content to a fortune cookie; and
- Email messages and calendar schedules; and
- Clock and/or stop watch.

For the avoidance of doubt, it should be understood that these examples are provided for illustration and are not intended to limit the inventions, including the scope of data that may be transmitted, received, or displayed by the device, nor any intermediate processing that may employed during such transfer and display.

Notably, selected content may be delivered according to different contexts. For example, in the morning, motivational messaging may be displayed along with the user's sleep data from the previous night. In the evening, a daily summary of the day's activities may be displayed. Notably, sleep and activity may be monitored and derived from other devices, manual log entries on a website, etc.—not the present invention. Such information, however, may be communicated to, for example, the user and/or the Internet via the device.

Furthermore, in several embodiments the device has a motivational avatar whose state is dependent on user activity. Nominally, the avatar may be a "flower" or plant that grows and shrinks as a function of the duration and intensity of a user's physical activity over a period of several hours. In a preferred embodiment, the device may be programmed with a customizable avatar and the behavior of the avatar may change over time as the user interacts with the device. The device may also be programmed with optional games and interventions to help the user meet goals.

Programming or customizing may be implemented via the user interface, an external device via the communication circuitry (for example, via wired or wireless connection to a computer or personal computing device) and/or through a web interface (e.g., www.fitbit.com) on the user interface of the device. Similarly, the firmware loaded on the device may be updated and configured by the user through the communication circuitry (for example, via wireless connection). Indeed, functions and features of the device (for example, certain sensors or data processing) as described here may also be modified, enabled and/or disabled (for example, on an individual basis or global basis).

In a preferred embodiment, the portable monitoring device may be mounted to different parts of the user and/or exercise equipment to perform functions that are specific or adapted to its location. For example, when mounted on the torso, the portable monitoring device may monitor the user's steps, distance, pace, calorie burn, activity intensity, altitude gain/loss, stair steps, etc. based on data from the motion sensor and altitude sensor using one set of algorithms. When the portable monitoring device is mounted to the user's foot, the device may monitor the same or similar parameters using possibly a different sensor configuration and another set of algorithms. Additionally, it the portable monitoring device may monitor the impact accelerations present on the foot to determine 1) if the user is running with soft or hard footfalls or 2) if the user is running on a soft or hard surface (e.g., the amount of time spent running on concrete vs. grass). When the portable monitoring device is mounted to the wrist, arm, hand, it may perform sleep tracking functionality, swimming functionality, ambulatory activity functionality, or stress biofeedback functionality using, in part or wholly, a heart rate and/or respiratory rate sensor and/or galvanic skin response (GSR) sensor—the determination of which mode of operation may be determined automatically through mode or motion sensor data, or the user may place the device into the appropriate mode manually.

Note that in the case of the hand, the portable monitoring device may be held rather than mounted. In a preferred embodiment, a gesture of the device mostly contained in the orthogonal plane to the gravitational vector may be used as a user interface mechanism (e.g., to navigate a menu system). Because the gesture is mostly orthogonal to gravity, it may be reliably distinguished between other motions that produce signals that are mostly parallel to gravity (e.g., walking, running, and jumping). In a preferred embodiment, the gesture is similar to the flick of the wrist (as typically produced when dealing cards or throwing a flying disc) and/or the reverse motion toward the body. Due to the fast motion of this gesture, it may be readily distinguished from other motions that are orthogonal to gravity (e.g., hip rotations). In lieu of or in combination with the preceding gesture, the device may incorporate another gesture wherein the direction of gravity relative to one or more axes of an accelerometer begins in a first orientation, then is moved to a second orientation that is roughly 90° degrees different, then returned to the first orientation. For example, in the case of a device with a 3D accelerometer, a 1 g acceleration may be sensed on one accelerometer axis in the first orientation (and close to 0 g on both other axes), then go to near 0 g in the second orientation (and close to 1 g on one of the other axes), then return to 1 g when the device is returned to the first orientation. Because such rotations do not occur often in natural use of an activity monitoring device, it may be readily used as a gesture for user interactions. Notably, these gestures may be recognized with a variety of sensors other than or in combination with an accelerometer such as a magnetic compass, gyroscope, mechanical switch, etc.

In regards to swim tracking, the use of inertial and/or magnetic sensors (e.g., compasses) may be used to determine the lap count of the user. Speed and distance may subsequently be calculated based on a configured lap length. When the device is placed on a bicycle hub or wheel, it may perform bicycle activity tracking (e.g., cadence, calorie burn).

As mentioned before, the portable monitoring device may also transmit its data to a secondary display device so that the user may see its output in real-time. In another embodiment, the device may communicate with another activity monitoring device (e.g., ANT-enabled heart rate monitor) either directly or indirectly through a wireless bridge (e.g., a smart phone that routes data from one device to another, or between both). When the portable monitoring device is placed on a free weight or weight training apparatus, it may perform functions related to weight training (e.g., tracking repetitions, sets, time between repetitions/sets, type of exercise, form.).

In another aspect of the present inventions, the portable monitoring device may select which sensors and algorithms to use based on its mounting condition. For instance, if the device is mounted to the arm, it uses an optical heart rate monitor to calculate calorie burn. If the portable monitoring device is mounted to the torso, it uses an accelerometer to calculate calorie burn. In this example, the device may determine its location partially or wholly from the quality of the heart rate signal: if no signal is present, the device is not mounted to the arm. In this example, mounting conditions may furthermore be determined through the design of the mounting fixtures. For example, the fixtures may have reflective and anti-reflective materials which enable the device to optically distinguish between a mounting to the torso and/or to the foot. Notably, the optical module in the portable monitoring device may incorporate an array of emitters (e.g., LEDs) and/or an array of detectors (e.g., photodiodes, photodetectors, photoreceptors) wherein the emitters/detectors have different locations relative to the body and may be used to find the best signal locations while reducing power consumption (by, for instance, dimming or turning off some emitters/detectors).

Other embodiments may employ fixtures and devices which have magnets and/or magnetic sensors (e.g., Hall effect sensors), RF beacons and transmitters, buttons, electrical contacts, proximity sensors, etc. The portable monitoring device may also be equipped with a magnetic field sensor which is used to recognize the magnetic signature of fixtures and other devices.

Note that an optical system for heart rate sensing may also be used to sense respiratory rate. The two signals are modulated into a single photoplethysmography (PPG) signal. When applied to stress biofeedback, the PPG sensor may provide information on heart rate, heart rate variability, and respiratory rate. This may be supplemented or supplanted with information from a GSR sensor in the device. The same information may be used with or without the motion sensor to assist in sleep tracking, specifically as they relate to sleep onset and sleep stages. In other embodiments of the invention, the device may also include ambient light sensing, noise sensing, as well as all possible combinations of the previously mentioned sensors. When mounted to the arm and used in ambulatory activity monitoring, the PPG-derived information may be displayed to the user on a secondary device such as a wrist-mounted watch.

Notably, when the portable monitoring device is mounted to the torso, a combination of motion sensing and altitude sensing may be used to detect periods in which the user is sitting, standing, and lying down.

The portable monitoring device may also include one or more environmental sensors to detect, measure and/or sense ambient environmental conditions. For example, the one or more environmental sensors may detect, measure and/or sense ambient pressure, temperature, sound, light, humidity, location and/or atmosphere. In this manner, the portable monitoring device may monitor, in addition to user activity, other metrics related to noise pollution/levels, weather, UV exposure, lighting conditions, and/or air quality.

In another embodiment, the portable monitoring device may monitor the RF signature of nearby devices in order to determine its location. For instance, a home may have a set of Bluetooth or ANT devices that are beaconing to form a signature for the home. Indeed, the portable monitoring device may monitor the signature in order to determine its location in the home. The portable monitoring device may also determine its location directly from a GPS-enabled device that has a compatible communication protocol with the invention (e.g., a Bluetooth enabled smart phone). The portable monitoring device may also use a barometric pressure sensor to determine the user's altitude. (Obviously, other communication protocols can be used too, like RFID, WiFi, NFC, etc).

The portable monitoring device may include a rechargeable battery or ultracapacitor to provide electrical power to the circuitry and other elements of the portable monitoring device. In one embodiment, the energy storage element (for example, battery or ultracapacitor) may obtain energy from, for example, a charger.

In one embodiment, the portable monitoring device includes an active or passive energy harvesting circuitry wherein the energy acquired, obtained and/or generated by the circuitry is employed to immediately power the device or stored in, for example a rechargeable battery or ultracapacitor for later use by the a rechargeable battery or ultracapacitor.

Figure 15A:
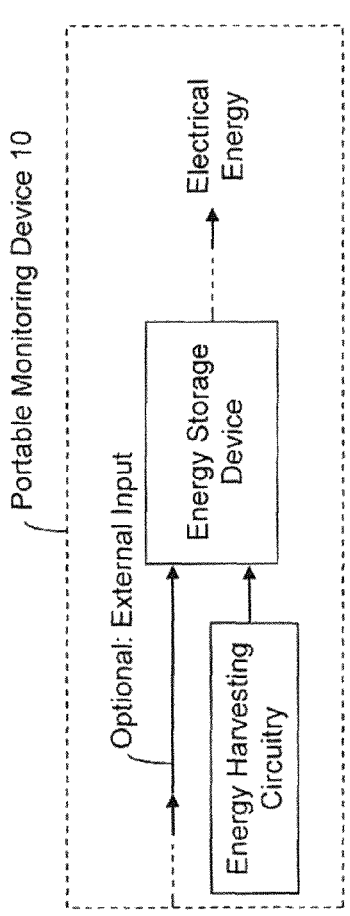
FIGS. 15A-15C are block diagram representations of exemplary portable monitoring devices including energy storage device (for example, a battery and/or ultracapacitor(s)) and/or energy harvesting circuitry wherein energy acquired, obtained and/or generated by the energy harvesting circuitry is employed to immediately power the device or stored in energy storage device; according to at least certain embodiments of the present inventions.
Figure 15B:
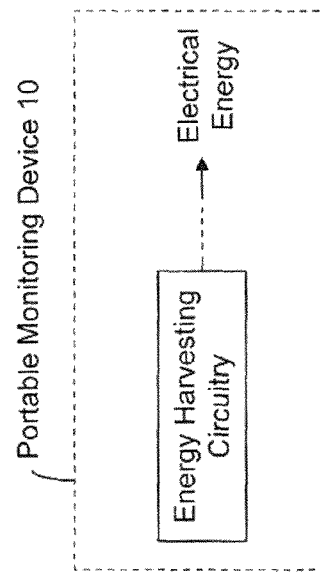
Figure 15C:
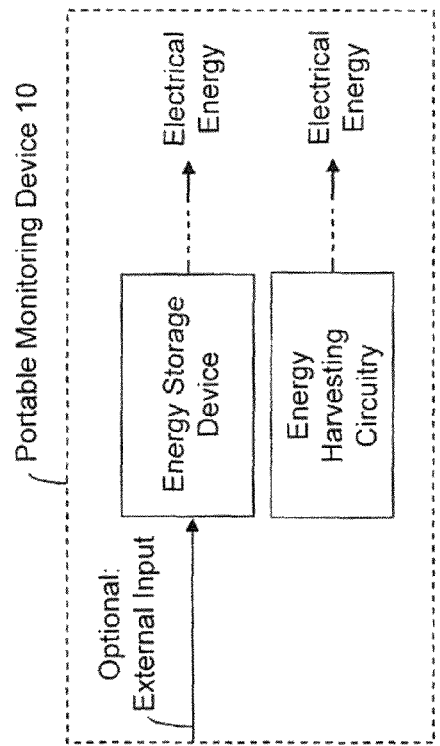
Figure 17:
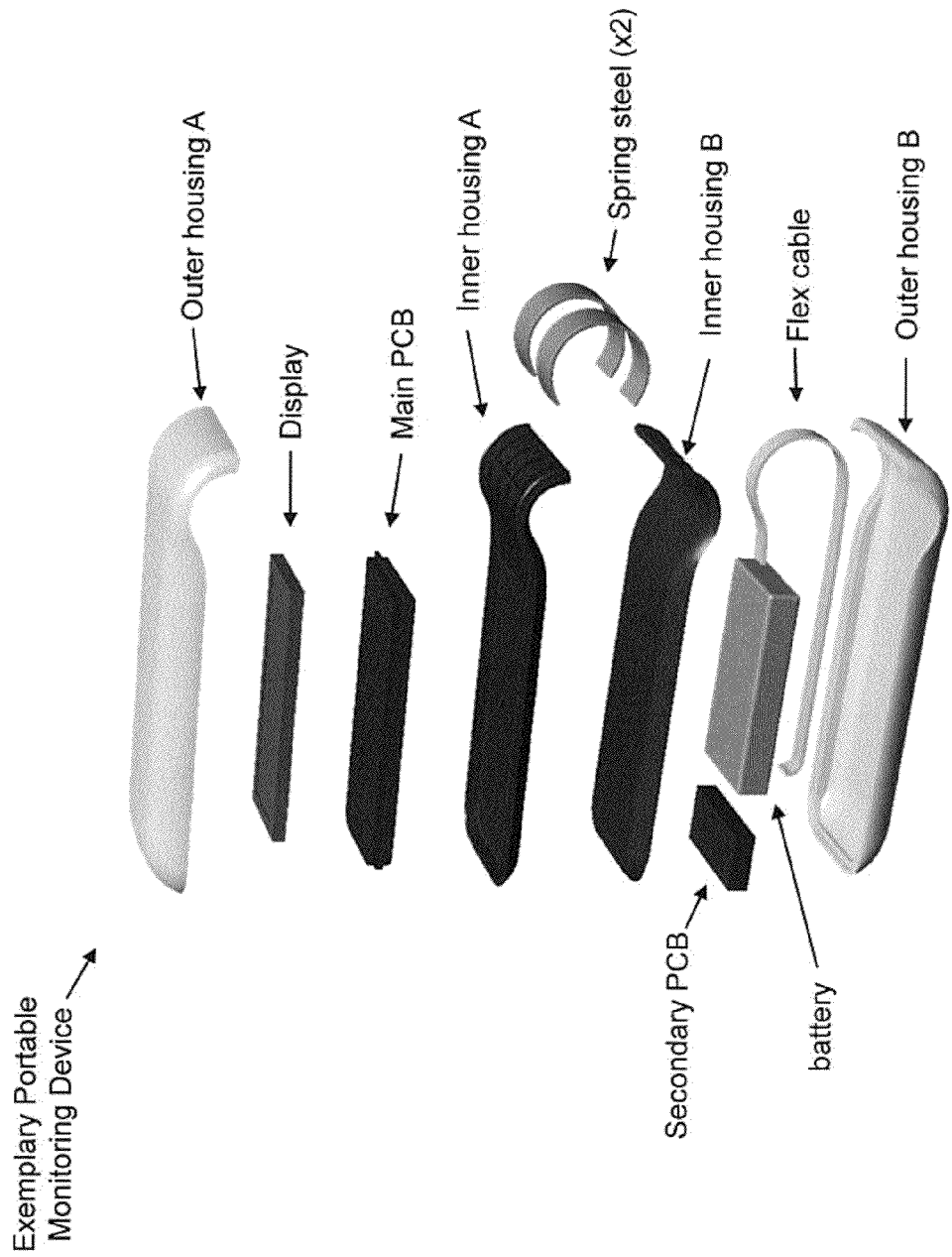
FIG. 17 illustrates, in exploded view form, an exemplary embodiment of the portable monitoring device of FIGS. 16A and 16B, according to certain aspects of the present inventions; notably, the sensors (for example, motion, altitude and/or physiological sensors) may be disposed on the main PCB.

With references to FIGS. 15A-15C, the energy harvesting circuitry portable monitoring device may convert the movement of the user to energy, using, for example, elements, circuitry and/or techniques which generate energy in response to the movement of the user (for example, moving magnets and/or piezoelectric elements). In this regard, the portable monitoring device passively "harvests" or converts the kinetic energy supplied by the user (for example, via movement) to charge the battery or ultracapacitor, supplement such charge, and/or immediately power the device. For example, the device may incorporate piezoelectric elements that generate current in response to user motion and associated circuitry to rectify and store said current. In lieu of or in combination, the device may incorporate a magnet that may move within an inductive coil such that motion of the device induces a current through the coil. The coil may be shaped as a cylinder, for example, to capture the motion shocks during user movement or ambulation, or it may be shaped as a toroid so that the magnet may move easily under other conditions.

In another embodiment, the portable monitoring device includes circuitry to "harvest" or acquire the energy from signals in the surrounding atmosphere. In this embodiment, the energy harvesting circuitry converts the energy of or in those signals to charge the battery or ultracapacitor, supplement such charge, and/or immediately power the device.

As mentioned above, at least a portion of the portable monitoring device (including the one or more altitude sensors and/or motion sensors) may be affixed to the user during operation wherein the portable monitoring device includes a physical size and/or shape that facilitates coupling to the user, for example, the body of the user (such as, for example, arm, wrist, angle, waist and/or foot) and allows the user to perform normal or typical user activities (including, for example, exercise of all kinds and type) without hindering the user from performing such activities. (See, for example, FIGS. 16A-16D and 17). The portable monitoring device may include a mechanism (for example, a clip, strap and/or tie) that facilitates coupling or affixing the device to the user during such normal or typical user activities. A base station may facilitate interface to a second device (for example, computer) and/or recharging of the battery. (See, for example, FIG. 16D).

It should be noted that the term "circuit" may mean, among other things, a single component or a multiplicity of components (whether in integrated circuit form or otherwise), which are active and/or passive, and which are coupled together to provide or perform a desired function. The term "circuitry" may mean, among other things, a circuit (whether integrated or otherwise), a group of such circuits, one or more processors, one or more state machines, one or more processors implementing software, one or more gate arrays, programmable gate arrays and/or field programmable gate arrays, or a combination of one or more circuits (whether integrated or otherwise), one or more state machines, one or more processors, one or more processors implementing software, one or more gate arrays, programmable gate arrays and/or field programmable gate arrays. The term "data" may mean, among other things, a current or voltage signal(s) whether in an analog or a digital form, which may be a single bit (or the like) or multiple bits (or the like).

It should be further noted that the various circuits and circuitry disclosed herein may be described using computer aided design tools and expressed (or represented), as data and/or instructions embodied in various computer-readable media, for example, in terms of their behavioral, register transfer, logic component, transistor, layout geometries, and/or other characteristics. Formats of files and other objects in which such circuit expressions may be implemented include, but are not limited to, formats supporting behavioral languages such as C, Verilog, and HLDL, formats supporting register level description languages like RTL, and formats supporting geometry description languages such as GDSII, GDSIII, GDSIV, CIF, MEBES and any other suitable formats and languages. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). The present inventions are also directed to such representation of the circuitry described herein, and/or techniques implemented thereby, and, as such, are intended to fall within the scope of the present inventions.

Indeed, when received within a computer system via one or more computer-readable media, such data and/or instruction-based expressions of the above described circuits may be processed by a processing entity (e.g., one or more processors) within the computer system in conjunction with execution of one or more other computer programs including, without limitation, net-list generation programs, place and route programs and the like, to generate a representation or image of a physical manifestation of such circuits. Such representation or image may thereafter be used in device fabrication, for example, by enabling generation of one or more masks that are used to form various components of the circuits in a device fabrication process.

Moreover, the various circuits and circuitry, as well as techniques, disclosed herein may be represented via simulations and simulation instruction-based expressions using computer aided design, simulation and/or testing tools. The simulation of the various sensors, processing circuitry, user interface, transmitter circuitry and/or receiver circuitry of the present inventions (regardless of combination or permutation of sensors, processing circuitry, transmitter circuitry and/or receiver circuitry), including the processes or techniques implemented thereby, may be implemented by a computer system wherein characteristics and operations of such circuitry, and techniques implemented thereby, are simulated, imitated, replicated, analyzed and/or predicted via a computer system. The present inventions are also directed to such simulations and testing of the inventive portable monitoring device (or portions thereof including, for example, the various sensors, processing circuitry, user interface, input/output circuitry (although not illustrated—the input/output circuitry may be discrete circuitry or circuitry which is integrated into the processing circuitry), transmitter circuitry and/or receiver circuitry), and/or techniques implemented thereby, and, as such, are intended to fall within the scope of the present inventions. The computer-readable media and data corresponding to such simulations and/or testing tools are also intended to fall within the scope of the present inventions.

The term "calculate" and other forms (i.e., calculating, calculated and calculation) in the claims means, among other things, calculate, assesses, determine and/or estimate and other forms thereof. In addition, the term "calorie burn" in the claims means, among other things, calorie burn or calorie expenditure and/or energy burn or energy expenditure—or the like.

Further, in the claims, the phrase "data which is representative of a change in altitude" means data which is representative of an altitude of the user (absolute altitude) and data which is representative of a change in altitude (relative altitude). Further, in the claims, the phrase "a change in altitude" means a change in altitude or height. Moreover, for the avoidance of doubt, in the claims, the term "flights of stairs" means "flights of stairs", "floors" and the like.

Notably, the terms "first," "second," and the like, herein do not denote any order, quantity, or importance, but rather are used to distinguish one element from another. Moreover, in the claims, the terms "a" and "an" herein do not denote a limitation of quantity, but rather denote the presence of at least one of the referenced item.

What is claimed is:

1. A portable monitoring device adapted to couple to a body of a user, the portable monitoring device comprising:
   a housing having a physical size and shape that is adapted to couple to the body of the user;
   a motion sensor, disposed in the housing, to detect motion of a user and, in response thereto, to generate data which is representative of motion of the user;
   an altitude sensor, disposed in the housing, to detect a change in altitude of the user and, in response thereto, to generate data which is representative of the change in altitude of the user;
   processing circuitry, disposed in the housing and coupled to the motion sensor and the altitude sensor, to calculate:
      a change in elevation of the user using the data which is representative of motion of the user and the data which is representative of a change in altitude of the user, and
      a state of an avatar using the data which is representative of motion of the user and/or the data which is representative of a change in altitude of the user; and
   a display, coupled to the processing circuitry, to output data which is representative of the state of the avatar, wherein the avatar is a graphical representation of the user.

2. The portable monitoring device of claim 1 wherein the display further outputs data of a number of stairs or flights of stairs traversed by the user.

3. The portable monitoring device of claim 1 wherein the state of the avatar is representative of a change in a physical appearance of the avatar on the display.

4. The portable monitoring device of claim 1 wherein the processing circuitry correlates data which is representative of the change in elevation of the user to a number of stairs or flights of stairs traversed by the user.

5. The portable monitoring device of claim 1 wherein the processing circuitry calculates the user traverses one or more stairs or flights of stairs using (i) data which is representative of a change in altitude per step and (ii) data which is representative of a change in altitude for a given time period.

6. The portable monitoring device of claim 1 wherein the processing circuitry determines the user traverses one or more stairs or flights of stairs by calculating a change in altitude over one or more steps of the user using (i) data which is representative of motion of the user and (ii) data which is representative of a change in altitude of the user.

7. The portable monitoring device of claim 1 wherein the processing circuitry determines the user traverses one or more stairs or flights of stairs based on (i) a change in altitude of the user per step being within or exceeding a first threshold range and (ii) a change in altitude of the user over a given time period being within or exceeding a second threshold range.

8. The portable monitoring device of claim 1 wherein the processing circuitry determines the user traverses one or more stairs or flights of stairs based on evaluating (i) a change in altitude in relation to a first threshold, and (ii) a change in altitude of the user per step in relation to a second threshold range and (iii) a change in altitude of the user over a given time period in relation to a third threshold range.

9. A portable monitoring device adapted to couple to a body of a user, the portable monitoring device comprising:
   a housing having a physical size and shape that is adapted to couple to the body of the user;
   a motion sensor, disposed in the housing, to detect motion of a user and, in response thereto, to generate data which is representative of motion of the user;
   an altitude sensor, disposed in the housing, to sample an altitude of the user in response to an altitude sample signal, wherein, in response to sampling the altitude of the user, the altitude sensor generates data which is representative of a change in altitude of the user; and
   processing circuitry, disposed in the housing and coupled to the motion sensor and the altitude sensor, to:
      generate the altitude sample signal using the data which is representative of motion of the user,
      calculate a change in elevation of the user using the data which is representative of a change in altitude of the user, and
      calculate a state of an avatar using the data which is representative of a change in altitude of the user; and a display, coupled to the processing circuitry, to output data which is representative of the state of the avatar, wherein the avatar is a graphical representation of the user.

10. The portable monitoring device of claim 9 wherein the processing circuitry:
   calculates a step frequency of the user using the data which is representative of motion of the user, and
   generates the altitude sample signal based on the step frequency of the user.

11. The portable monitoring device of claim 9 wherein the motion sensor samples motion of the user at a predetermined rate, wherein, in response to sampling the motion of the user, the motion sensor generates the data which is representative of motion of the user.

12. The portable monitoring device of claim 9 wherein the processing circuitry generates the altitude sample signal in response to determining a step by the user and/or after a predetermined period of time.

13. The portable monitoring device of claim 9 wherein the processing circuitry correlates data which is representative of the change in elevation of the user to a number of stairs or flights of stairs traversed by the user.

14. The portable monitoring device of claim 9 wherein the processing circuitry calculates the user traverses one or more stairs or flights of stairs using (i) data which is representative of a change in altitude per step and (ii) data which is representative of a change in height for a given time period.

15. The portable monitoring device of claim 9 wherein the processing circuitry determines the user traverses one or more stairs or flights of stairs by calculating a change in altitude over one or more steps of the user using (i) data which is representative of motion of the user and (ii) data which is representative of a change in altitude of the user.

16. The portable monitoring device of claim 9 wherein the processing circuitry determines the user traverses one or more stairs or flights of stairs based on (i) a change in altitude of the user per step exceeding a first threshold and (ii) a change in altitude of the user over a given time period exceeding a second threshold.

17. The portable monitoring device of claim 9 wherein the processing circuitry determines the user traverses one or more stairs or flights of stairs based on (i) a change in altitude of the user per step being within a first threshold range and (ii) a change in altitude of the user over a given time period being within a second threshold range.

18. The portable monitoring device of claim 9 wherein the processing circuitry determines the user traverses one or more stairs or flights of stairs based on evaluating (i) a change in altitude in relation to a threshold, and (ii) a change in altitude of the user per step in relation to a first threshold range and (iii) a change in altitude of the user over a given time period in relation to a second threshold range.

19. A portable monitoring device adapted to couple to a body of a user, the portable monitoring device comprising:
   a housing having a physical size and shape that is adapted to couple to the body of the user;
   a motion sensor, disposed in the housing, to detect motion of a user and, in response thereto, to generate data which is representative of motion of the user;
   an altitude sensor, disposed in the housing, to detect a change in altitude of the user and, in response thereto, to generate data which is representative of the change in altitude of the user;
   processing circuitry, disposed in the housing and coupled to the motion sensor and the altitude sensor, to calculate:
      a change in elevation of the user using the data which is representative of motion of the user and the data which is representative of a change in altitude of the user,
      a number of steps taken by the user using the data which is representative of motion of the user, and
      a state of an avatar using the data which is representative of the change in elevation of the user and data which is representative of the number of steps taken by the user; and
   a display, coupled to the processing circuitry, to output data which is representative of the state of the avatar, wherein the avatar is a graphical representation of the user.

20. The portable monitoring device of claim 19 wherein the state of the avatar is representative of a change in a physical appearance of the avatar.

21. The portable monitoring device of claim 19 wherein the processing circuitry calculates the user traverses one or more stairs or flights of stairs using (i) data which is representative of a change in altitude per step and (ii) data which is representative of a change in height for a given time period.

22. The portable monitoring device of claim 19 wherein the processing circuitry determines the user traverses one or more stairs or flights of stairs by calculating a change in altitude over one or more steps of the user using (i) data which is representative of motion of the user and (ii) data which is representative of a change in altitude of the user.

23. The portable monitoring device of claim 19 wherein the processing circuitry determines the user traverses one or more stairs or flights of stairs based on (i) a change in altitude of the user per step exceeding a first threshold and (ii) a change in altitude of the user over a given time period exceeding a second threshold.

24. The portable monitoring device of claim 19 wherein the processing circuitry determines the user traverses one or more stairs or flights of stairs based on (i) a change in altitude of the user per step being within a first threshold range and (ii) a change in altitude of the user over a given time period being within a second threshold range.

25. The portable monitoring device of claim 19 wherein the processing circuitry determines the user traverses one or more stairs or flights of stairs based on evaluating (i) a change in altitude in relation to a threshold, and (ii) a change in altitude of the user per step in relation to a first threshold range and (iii) a change in altitude of the user over a given time period in relation to a second threshold range.

26. The portable monitoring device of claim 19 wherein the processing circuitry correlates data which is representative of the change in elevation of the user to a number of stairs or flights of stairs traversed by the user.

27. The portable monitoring device of claim 19 wherein:
   the altitude sensor samples an altitude of the user in response to an altitude sample signal, wherein, in response to sampling the altitude of the user, the altitude sensor generates the data which is representative of a change in altitude of the user, and
   the processing circuitry generates the sample signal using the data which is representative of motion of the user.

28. A portable monitoring device adapted to couple to a body of a user, the portable monitoring device comprising:
   a housing having a physical size and shape that is adapted to couple to the body of the user;
   a motion sensor, disposed in the housing, to detect motion of a user and, in response thereto, to generate data which is representative of motion of the user;

an altitude sensor, disposed in the housing, to detect a change in altitude of the user and, in response thereto, to generate data which is representative of the change in altitude of the user;

processing circuitry, disposed in the housing and coupled to the motion sensor and the altitude sensor, to calculate:
- a change in elevation of the user using the data which is representative of motion of the user and the data which is representative of a change in altitude of the user,
- a calorie burn of the user using (i) the data which is representative of motion of the user and (ii) the data which is representative of a change in altitude of the user, and
- a state of an avatar using the data which is representative of the calorie burn of the user; and a display, coupled to the processing circuitry, to output data which is representative of the state of the avatar, wherein the avatar is a graphical representation of the user.

29. The portable monitoring device of claim 28 wherein the state of the avatar is representative of a change in a physical appearance of the avatar.

\* \* \* \* \*